US009125931B2

(12) United States Patent
Belmont et al.

(10) Patent No.: US 9,125,931 B2
(45) Date of Patent: Sep. 8, 2015

(54) POST-TRANSCRIPTIONAL REGULATION OF RNA-RELATED PROCESSES USING ENCODED PROTEIN-BINDING RNA APTAMERS

(75) Inventors: Brian J. Belmont, Cambridge, MA (US); Stephen J. Goldfless, Cambridge, MA (US); Michael A. Marletta, Berkeley, CA (US); Jacquin C. Niles, Arlington, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 669 days.

(21) Appl. No.: 12/755,121

(22) Filed: Apr. 6, 2010

(65) Prior Publication Data
US 2011/0245326 A1 Oct. 6, 2011

(51) Int. Cl.
| | | |
|---|---|---|
| C07H 21/04 | (2006.01) |
| C12N 15/63 | (2006.01) |
| A61K 31/713 | (2006.01) |
| C12N 15/115 | (2010.01) |
| A61K 31/70 | (2006.01) |

(52) U.S. Cl.
CPC ............ *A61K 31/713* (2013.01); *C12N 15/115* (2013.01); *C12N 2310/16* (2013.01)

(58) Field of Classification Search
CPC ............................ A61K 31/713; C12N 15/115
USPC ........................................... 536/24.1; 435/455
See application file for complete search history.

(56) References Cited

U.S. PATENT DOCUMENTS

| | | | |
|---|---|---|---|
| 3,817,837 A | 6/1974 | Rubenstein | 195/103.5 |
| 3,850,752 A | 11/1974 | Schuur et al. | 195/103.5 |
| 3,939,350 A | 2/1976 | Kronick et al. | 250/365 |
| 3,996,345 A | 12/1976 | Ullman et al. | 424/12 |
| 4,275,149 A | 6/1981 | Litman et al. | 435/7 |
| 4,277,437 A | 7/1981 | Maggio | 422/61 |
| 4,366,241 A | 12/1982 | Tom et al. | 435/7 |
| 4,683,195 A | 6/1987 | Mullis et al. | 435/6 |
| 4,683,202 A | 6/1987 | Mullis | 435/91 |
| 4,981,785 A | 1/1991 | Nayak | 435/7 |
| 5,358,691 A | 10/1994 | Clark et al. | 422/64 |
| 5,538,848 A | 7/1996 | Livak et al. | 435/5 |
| 5,599,677 A | 2/1997 | Dowell et al. | 435/7 |
| 5,639,606 A | 6/1997 | Willey | 435/6 |
| 5,643,765 A | 7/1997 | Willey | 435/91.2 |
| 5,672,480 A | 9/1997 | Dowell et al. | 435/7.4 |
| 5,705,188 A | 1/1998 | Junichi et al. | 424/450 |
| 5,846,717 A | 12/1998 | Brow et al. | 435/6 |
| 5,876,978 A | 3/1999 | Willey et al. | 435/91.2 |
| 5,885,530 A | 3/1999 | Babson et al. | 422/65 |
| 5,985,557 A | 11/1999 | Prudent et al. | 435/6 |
| 5,994,069 A | 11/1999 | Hall et al. | 435/6 |
| 6,001,567 A | 12/1999 | Brow et al. | 435/6 |
| 6,090,543 A | 7/2000 | Prudent et al. | 435/6 |
| 6,159,750 A | 12/2000 | Edmonds et al. | 436/537 |
| 6,635,440 B1 * | 10/2003 | Hentze et al. | 435/29 |
| 2005/0053951 A1 | 3/2005 | Breaker et al. | 435/6 |
| 2006/0128649 A1 | 6/2006 | Ramachandra | 514/44 |
| 2007/0136827 A1 | 6/2007 | Collins et al. | 800/14 |

FOREIGN PATENT DOCUMENTS

| | | |
|---|---|---|
| WO | WO 8909283 | 10/1989 |
| WO | WO 9323564 | 11/1993 |
| WO | WO 9730731 | 8/1997 |
| WO | WO 9813523 | 4/1998 |
| WO | WO 9828440 | 7/1998 |
| WO | WO 0043540 | 7/2000 |

OTHER PUBLICATIONS

Chen et al. Dietary iron intake modulates the activity of iron-regulatory proteins and the abundance of ferritin and mitochondrial aconitase in rat liver. J. Nutr. 127:236-246, 1997.*
Hunsicker et al. An RNA aptamer that induces transcription. Chemistry & Biology 16:173-180, 2009.*
Suess et al. Conditional gene expression by controlling translation with tetracycline-binding aptamers. Nucleic Acids Research 31:1853-1858, 2003.*
Belmont et al. Engineering a direct and inducible protein-RNA interaction to regulate RNA biology. ACS Chemical Biology 5:851-861, 2010.*
Abad et al., "Requirements for gene silencing mediated by U1 snRNA binding to a target sequence" *Nucl. Acid Res.* 36-2338-2352 (2008).
Ashizuka et al., "Novel Translation Control through an Iron-Responsive Element by Interaction of Multifunctional Protein YB-1 and IRP2" *Mol. Cell. Biol.* 22:6375-6383 (2002).
Babendure et al, "Control of mammalian translation by mRNA structure near caps" *RNA* 12:851-861 (2006).
Babianian et al., "Mechanism of selective translation of vaccinia virus mRNAs: differential role of poly(A) and initiation factors in the translation of viral and cellular mRNAs" *J. Virol* 65:4449-4460 (1991).
Bailey et al., "MEME: discovering and analyzing DNA and protein sequence motifs" *Nucleic Acids Res* 34: W369-373 (2006).
Bailey et al., "The value of prior knowledge in discovering motifs with MEME" *Proc Intl Conf Intell Syst Mol Biol* 3:21-29 (1995).
Baron-Benhamou et al., "Using the lambdaN peptide to tether proteins to RNAs" *Methods Mol. Biol* 257:135-154 (2004).
Bashirullah et al., "RNA localization in development". *Annu. Rev. Biochem* 67:335-394 (1998).
Baumeister et al., "Contacts between Tet repressor and tet operator revealed by new recognition specificities of single amino acid replacement mutants" *J Mol Biol* 226: 1257-1270 (1992).
Beach et al, "ASH1 mRNA localization in three acts" *Mol Biol Cell* 12, 2567-2577 (2001).

(Continued)

*Primary Examiner* — Quang Nguyen

(74) *Attorney, Agent, or Firm* — Medlen & Carroll, LLP

(57) ABSTRACT

In vitro SELEX has been used to discover high affinity RNA aptamers interacting with the tetracycline repressor protein in a tetracycline-dependent manner. Using in silico RNA folding predictions to guide the design of both aptamer truncations and mutants, minimized tetracycline repressor protein high affinity binding aptamers have been defined. Using one such aptamer, inducible post-transcriptional regulation in vivo has been demonstrated that is predicated on a direct interaction between a tetracycline repressor protein and a RNA aptamer element. These aptamer components can be integrated in any organism to inducibly regulate RNA translation of a gene of interest.

9 Claims, 20 Drawing Sheets

(56) References Cited

OTHER PUBLICATIONS

Belli et al., "An activator/repressor dual system allows tight tetracycline regulated gene expression in budding yeast" *Nucleic Acids Res* 26:942-947 (1998).
Bochkov et al., "Translational efficiency of EMCV IRES in bioistronic vectors is dependent upon IRES sequence and gene location." *BioTechniques* 41:283-288 (2006).
Borneman et al., "Divergence of transcription factor binding sites across related yeast species" *Science* 317:815-819 (2007).
Brodsky et al, "A microbead-based system for identifying and characterizing RNA-protein interactions by flow cytometry" *Mol Cell Proteomics* 1:922-929 (2002).
Bruell et al., "Conservation of bacterial protein synthesis machinery: initiation and clogation in *Mycobacterium smegmatis*" *Biochemistry* 47:8828-8839 (2008).
Casey et al., "Iron regulation of transferrin receptor mRNA levels requires iron-responsive elements and a rapid turnover determinant in the 3' untranslated region of the mRNA" *EMBO J* 8:3693-3699 (1989).
Chiaruttini et al., "Dendritie trafficking of BDNF mRNA is mediated by translin and blocked by the G196A (Val66Met) mutation" *Proce Natl Acad Sci USA* 106 16481-16486 (2009).
Cogoui et al., "Post-transcripitional gene sileacing across kingdoms" *Current Opinion in Genetics & Development* 10:638-643 (2000).
Coller et al., "Tethered function assays using 3' untranslated regions" *Methods* 26;142-150 (2002).
Dreyfus et al., "The Poly(A) Tail of mRNAs Bodyguard in Eukaryotes, Scavenger in Bacteria" *Cell* 111:611-613 (2002).
Duszenko et al., In vitro translation in a cell-free system from Trypanosoma brucei yields glycosylated and glycosy[phosphatidy]inositol-anchored proteins *Eur. J. Biochem* 266:789-797 (1999).
Ellington et al., "In vitro selection of RNA molecules that bind specific ligands" *Nature* 346:818-822 (1996).
Ettner et al., "Fast large-scale purification of tetracycline repressor variants from overproducing *Escherichia coli* strains" *J Chromatogr* 4 742.
Evdokimova et al., "The Major Core Protein of Messenger Ribonucleoprotein Particles (p. 50) Promotes Initiation of Protein Biosynthesis in Vitro"*J Biol Chem* 273:3574-3581 (1998).
Gebauer et al., "Molecular mechanisms of translation control" *Nat Rev Mol Cell Biol* 5;827-835 (2004).
Gingras et al., "eIF4 initiation factors: effectors of mRNA recruitment to ribosomes and regulators of translation" *Annu. Rev. Biochem* 68:913-963 (1999).
Good L., "Translation repression by antisense sequences"*Cell Mol Life Sci* 60:854-861 (2003).
Goossen et al., "Position is the critical determinant for function of iron-responsive elements as translational regulators" *Mol Cell Biol* 12:1959-66 (1992).
Goraczniak et al., "Gene silencing by synthetic U1 Adaptors" *Nat Biotech* 27:257-263 (2009).
Grskovic et al., "A co-repressor assembly nucleated by Sex-lethal in the 3[prime]UTR mediates translational control of *Drosophils* msl-2 mRNA" *EMBO J* 22:5571-5581 (2003).
Gunderson et al., "U1 snRNP inhibits pre-mRNA polyadenylation through a direct interaction between U1 70K and poly(A) polymerase" *Mol Cell* 1:255-264 (1998).
Gunnewiek et al., "Fourteen Residues of the U1 snRNP-Specific U1A Protein Are Required for Homodimerization, Cooperative RNA Binding, and Inhibition of Polyadenylation" *Mol. Cell. Biol.* 20:2209-2217 (2000).
Hammond S.M., "Dicing and slicing: the core machinery of the RNA interference pathway" *FEBS Lett* 579:5822-5829 (2005).
Hanson et al., "Tetracycline-aptamer mediated translation regulation in yeast" *Mol. Microbiol* 49:1627-1637 (2003).
Hentze et al., "Balancing Acts: Molecular Control of Mammalian Iron Metabolisn" *Cell* 117:285-297 (2004).

Heo et al., "P1(3,4,5)P3 and P1(4,5)P2 lipids target proteins with polybasic clusters to the plasma membrane" *Science* 314:1458-1461 (2006).
Hillen et al., "Mechanisms underlying expression of Tn10 encoded tetracycline resistance" *Annu Rev Microbiol* 48:345-369 (1994).
Hinton et al., "Functional Analysis of Individual Binding Activites of the Scaffold Protein dF4G" *J Biol Chem* 282:1695-1708 (2007).
Hirekawa, N., "mRNA Transport in Dendrites: RNA Granules, Motors, and Tracks" *J. Neurosci.* 26:7139-7142 (2006).
Huang et al., "Facilitation of dendritic mRNA transport by CPEB" *Genes Dev* 17:638-653 (2003).
Hunsicker et al, "An RNA aptamer that induces transcription" *Chem & Biol* 16:173-180 (2009).
Hussain et al., "Translation of homologous and herterologous messenger RNAs in a yeast cell-free system"*Gene* 46:13-23 (1986).
Hwang et al., "Inhibition of gene expresssion in human cells through small molecule-RNA interactions" *Proc. Natl. Acad. Sci. U.S.A.* 96:12997-13002 (1999.
Isaacs et al., "RNA synthetic biology" *Nat Biotechnol* 24:545-554 (2006).
Jenner et al., "Translational operator of mRNA on the ribosome: how repressor proteins exclude ribosome binding" *Science* 308:120-123 (2005).
Kamionka et al., "Two mutations in the tetracycline repressor change the inducer anhydrotetracycline to a corepressor" *Nucleic Acids Res* 32:842-847 (2004).
Kapp et al., "The molecular mechanies of eukaryotic translation" *Annu Rev Biochem* 73:657-704 (2004).
Kataoka et al., "Pre-mRNA Splicing Imprint mRNA in the Nucleus with a Novel RNA binding Protein that Persists in the Cytoplasm" *Molecular Cell* 6:673-682 (2000).
Kato et al., "Iron/IRP-1-dependent regulation of mRNA expression for transferrin receptor, DMTI and ferritin during human erythroid differentiation" *Expertmental Hematology* 35:879-887 (2007).
Keryer-Bibens et al., Tethering of proteins to RNAs by bacteriophage proteins. Biol. Cell 100, 125 (2008).
Kim et al., "Translation Repressor Activity is Equivalent and is Quantititively Predicted by in Vitro RNA Binding for Two Iron-responsive Element binding Proteins. IRP1 and IRP2" *J Biol Chem* 270:4983-4986 (1995).
Ko et al., "Identification of new poly(A) polymerase-inhibitory proteins capable of regulating pre-mRNA polyadenylation" *J Mol. Biol* 318:1189-1206 (2002).
Koloteva et al., "The position dependence of translation regulation via RNA-RNA and RNA-protein interactions in the 5'-untranslated region of eukaryotic mRNA is a function of the thermodynamic competence of 40S ribosomes in translation initiation" *J Biol Chem* 272:16531-16539 (1997).
Kolter et al., "Attenuation in amino acid biosynthetic operons" *Annu Rev Genet* 16:113-134 (1982).
Kotter et al., "A fast and efficient translational control system for conditional expression of yeast genes" *Nucleic Acids Res* :37(18):e120 (2009).
Krueger et al., "Single-chain Tet transregulators" *Nucleic Acids Res* 31:3050-3056 (2003).
Lécuyer et al., "Global Analysis of mRNA Localization Reveals a Prominent Role in Organizing Cellular Architecture and Function" *Cell* 131:174-187 (2007).
Lécuyer, et al., "Fluorescent in situ hybridization protocols in Drosophila embryos and tissues" *Methods Mol Biol* 420:289-302 (2008).
Lee et al., "Directed evolution of *AraC* for improved compatibility of arabinose-and lactose-inducible promoters" *Appl Environ Microbiol* 73:5711-5715 (2007).
Leonard et al., "Complex Formation between Potyvirus VPg and Translation Eukaryotic Inititation Factor 4E Correlates with Virus Infectivity" *J. Virol.* 74:7730-7737 (2000).
Link et al., "Engineering high-speed allosteric hammerhead ribozymes" *Biol Chem* 388:779-786 (2007).
Mader et al., "The translation initiation factor eIF-4E binds to a common motif shared by the translation factor eIF-4 gamma and the translational repressors 4E-binding proteing" *Mol. Cell Biol* 15:4990-4997 (1995).

(56) References Cited

OTHER PUBLICATIONS

Maniatis, T. et al., "Regulation of inducible and tissue-specific gene expression," *Science* 236;1237 (1987).
Mansfield et al., "The ribonome: a dominant force in co-ordinating gene expression"*Biol. Cell* 101:169-181 (2009).
Marcotrigiano et al., Cap-Dependent Translation Initiation in Eukaryotes is Regulated by a Molecular Mimic of eIF4G. *Molecular Cell* 3:707-716 (1999).
Marion et al., "The N-terminal half of the influenza virus NS1 protein is sufficeint for nuclear retention of mRNA and enhancement of viral mRNA translation" *Nucl. Acids Res*. 25:4271-4277 (1997).
Maris et al., "The RNA recognition motif, a plastic RNA-binding platform to regulate post-transcriptional gene expression" *FEBS J* 272:2118-2131 (2005).
Martin et al., "RNA Trafficking and Local Protein Synthesis in Dendrites: An Overview" *J. Neurosci*. 26:7131-7134 (2006).
Mathews et al., "Expanded sequence dependence of thermodynamic parameters improves prediction of RNA secondary structure" *J Mol Biol* 288:911-940 (1999).
Mazumder et al., "Translational control by the 3'-UTR: the ends specify the means" *Trends in Biochemical Sciences* 28:91-98 (2003).
Mazumder et al., "Translational Silencing of Ceruloplasmin Requires the Essential Elements of mRNA Circularization:Poly(A) Tail, Poly(A)-Binding Protein, and Eukaryotie Translation Initiation Factor 4G" *Mol. Cell. Biol*. 21:6440-6449 (2001).
McCarthy, J.E., "Posttranscriptional Control of Gene Expression in Yeast" *Microbiol. Mol. Biol. Rev*. 62:1492-1553 (1998).
Meissner et al., "Molecular tools for analysis of gene function in parasitic microorganisms" *Appl Microbiol Biotechnol* 75.963-975 (2007).
Mello et al., "Revealing the world of RNA interference" *Nature* 431:338-342 (2004).
Mikami et al., "An efficient mammalian cell-free translation system supplemented with translation factors" *Protein Expresion and Purification* 46:348-357 (2006).
Mowry, K.I., "Complex formation between stage-specific oocyte factors and a Xenopus mRNA localization element" *Proc. Natl. Acad. Set. U.S.A* 93:14608-14613 (1996).
Muckenthaler et al., "IRP-1 Binding to Ferritin mRNA Prevents the Recruitment of the Small Ribosomal Subunit by the Cap-Binding Complex eIF4F" *Molecular Cell* 2:383-388 (1998).
Mureey et al., "Species-independent translational leaders facilitate cell-free expression" *Nat Biotech* 27:747-752 (2009).
Myette et al., "Domain Structure of the Vaccinia Virus mRNA Capping Enzyme" *J Biol Chem* 271:11936-11944 (1996).
Napoli et al., "The Fragile X Syndrome Protein Represses Activity-Dependent Translation through CYFIP1, a New 4E-BP" *Cell* 134:1042-1054 (2008).
Nelson et al., "*Drosophila* Cup is an eIF4E-binding protein that functions in Smaug-mediated translational repression" *EMBO J* 23:150-159 (2004).
Nie et al., "Different modes and potencies of translational repression by sequence-specific RNA-protein interaction at the 5'UTR" *Nucleic Acids Res* 34:5528-5540 (2006).
Odom et al., "Tissue-specific transcriptional regulation has diverged significantly between human and mouse" *Nat Genet* 39:730-732 (2007).
Orth et al., "Structural basis of gene regulation by the tetracycline inducible Tet repressor-operator system" *Nat Struct Biol* 7:215-219 (2000).
Paraskeva et al., "A translational repression assay procedure (TRAP) for RNA-protein interactions in vivo" *Proc Natl Acad Sci USA* 95:951-956 (1998).
Pfaffi M.W., "A new mathematical model for relative quantification in realtime RT-PCR" *Nucleic Acids Res* 29: e45 (2001).
Pokrovskaya et al., "In vitro transcription: preparative RNA yields in analytical scale reactions" *Anal Biochem* 220:420-423 (1994).
Poulin et al., "4E-BP3, a New Member of the Eukaryotic Initiation Factor 4E-binding Protein Family" *J Biol Chem* 273:14002-14007 (1998).

Preiss et al., "Starting the protein synthesis machine: eukaryotic translation initiation" *Bioessays* 25:1201-1211 (2003).
Prevöt et al., "Conducting the initiation of protein synthesis: the role of eIF4G" *Biol. Cell* 95:141-156 (2003).
Proske et al., "Aptamers-basic research, drug development, and clinical applications" *Appl. Microbiol. Biotechnol* 69:367-374 (2005).
Qiu et al., "The influenza virus NS1 protein is a poly(A)-binding protein that inhibits nuclear export of mRNAs containing poly(A)" *J. Virol*. 68:2425-2432 (1994).
Rifo et al., "Back to basics: the untreated rabbit teticulocyte lynate as a competive system to recapitulate cap/poly(A) synergy and the selective advantage of IRES-driven translation" *Nucl. Acids Res*. 35:e121 (2007).
Rouault T.A., "The role of iron regulatory proteins in mammaline iron homeostasis and disease" *Nat Chem Biol* 2:406-414 (2006).
Samaniego et al., "Molecular characteization of a second iron-responsive element binding protein, iron regulatory protein 2 Structure, Function, and post-translation regulation" *J Biol Chem* 269:30904-30910 (1994).
Schuldt et al., "Miranda mediates asymmetric protein and RNA localization in the developing nervous system" *Genes & Development* 12:1847-1857 (1998).
Siomi et al., "RNA-binding proteins as regulators of gene expression" *Curr. Opin. Genet. Dev* 7:345-353 (1997).
Soukup et al., "Engineering precision RNA molecular switches" *Proc Natl Acad Sci USA* 96:3584-3589 (1999).
Stebbins-Boaz et al., "Maskin is a CPEB associated factor that transiently interacts with e1F-1E" *Mol. Cell* 4:1017-1027 (1999).
Stripecke et al., "Proteins binding to 5' untranslated region sites: a general mechanism for translational regulation of mRNAs in human and yeast cells" *Mol. Cell. Biol*. 14:5898-5909 (1994).
Suess et al, "A theophylline responsive riboswitch based on helix slipping controls gene expression in vivo" *Nucleic Acids Res* 32:1610-1614 (2004).
Suess et al., "Conditional gene expression by controlling translation with tetracycline-binding aptamers" *Nucleic Acids Res* 31:1853-1858 (2003).
Surolia et al., "Chloroquine inhibits heme-dependent protein synthesis in *Plasmodium falciparum*" *PNAS* 88:4786-4790 (1991).
Svitkin et al., "General RNA binding proteins render translation cap dependent " *EMBO J* 15:7147-7155 (1996).
Taddei et al., "Separation of silencing from perinuclear anchoring functions in yeast Ku80, Sir4 and Esc1 proteins, " *EMBO J.* 23:1301-1312 (2004).
Tsuboi et al., "Wheat Germ Cell-Free System-Based Production of Malaria Proteins for Discovery of Novel Vaccine Candidates" *Infect. Immun.* 76:1702-1708 (2008).
Tuerk et al., "Systematic evolution of ligands by exponential enrichment: RNA ligands to bacteriophage T4 DNA polymerase" *Science* 249:505-510 (1990).
Valencia et al., "Splicing promotes rapid and efficienct mRNA export in mammalian cells" *Procd Natl Acad Sci USA* 105:3386-3391 (2008).
Walden et al. "Structure of dual function iron regulatory protein 1 complexed with ferritin IRE-RNA" *Science* 314:1903-1908 (2006).
Warren et al., "A novel binding assay to assess specificity of monoclonal antibodies" *J Immunol Methods* 305:33-38 (2005).
Weigand et al., "Aptamers and riboswitches: perspectives in biotechnology" *Appl. Microbiol. Biotechnol* 85:229-236 (2009).
Weigand et al., "Tetracycline aptamer-controlled regulation of pre-mRNA splicing in yeast" *Nucl. Acids Res*. 35:4179-4185 (2007).
Wilkomm D, Hartmann R (2005), eds Hartmann R, Bindereif A, Schon A, Westhof E (WILEY-VCH Verlag GmbH & Co. KGaA, Weinheim), pp.86-94.
Win et al., "A modular and extensible RNA-based gene regulatory platform for engineering cellular function" *Proc Natl Acad Sci USA* 104:14283-14288.
Win et al., "Higher-Order Cellular INformation Processing with Synthetic RNA Devices" *Science* 322:456-460 (2008).
Winkler et al., "Regulation of bacterial gene expression by riboswitches" *Annu Rev Microbiol* 59:487-517 (2005).

(56) References Cited

OTHER PUBLICATIONS

Winkler et al., "Thiamine derivatives bind messenger RNAs directly to regulate bacterial gene expression" *Nature* 419:952-956 (2002).
Yen et al, "Exogenous control of mammalian gene expression through modulation of RNA Self-clevage" *Nature* 431 471-476 (2004).
Zhao et al, "Formation of mRNA 3' Ends in Eukaryotes: Maechanism, Regulation and Interrelationships with Other Steps in mRNA Synthesis" *Microbiol. Mol. Biol. Rev.* 63:405-445 (1999).
Zuker M., "Mfold web server for nucleic acid folding and hybridization prediction" *Nucleic Acids Res* 31:3406-3415 (2003).

\* cited by examiner

|        |          | Motif #2 |              | Motif #1 |         |
|--------|----------|----------|--------------|----------|---------|
| 5-1    | CUCCUCUAGUGAAGG | ACAUUCC | AGGUCGAUACGGA | CAUCGUUC | GAUGGCC |
| mut #1 | CUCCUCUAGUGAAGG | ACAUUCC | AGGUCGAUACGGA | GAUCGUUG | GAUGGCC |
| mut #2 | CUCCUCUAGUGAAGG | CCAUUGG | AGGUCGAUACGGA | CAUCGUUC | GAUGGCC |
| mut #1,2 | CUCCUCUAGUGAAGG | CCAUUGG | AGGUCGAUACGGA | GAUCGUUG | GAUGGCC |

SEQUENCE LISTING

```
<160> NUMBER OF SEQ ID NOS: 36

<210> SEQ ID NO 1
<211> LENGTH: 122
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (49)..(98)
<223> OTHER INFORMATION: where n= a randomized base.

<400> SEQUENCE: 1
ccgaagctta atacgactca ctatagggag ctcagaataa acgctcaann nnnnnnnnnn      60
nnnnnnnnnn nnnnnnnnnn nnnnnnnnnn nnnnnnnntt cgacatgagg cccggatccg     120
gc                                                                    122

<210> SEQ ID NO 2
<211> LENGTH: 48
<212> TYPE: DNA
<213> ORGANISM: Artificial sequence
<220> FEATURE:
<223> OTHER INFORMATION: synthetic

<400> SEQUENCE: 2
ccgaagctta atacgactca ctatagggag ctcagaataa acgctcaa                   48

<210> SEQ ID NO 3
<211> LENGTH: 24
<212> TYPE: DNA
<213> ORGANISM: Artificial sequence
<220> FEATURE:
<223> OTHER INFORMATION: synthetic

<400> SEQUENCE: 3
gccggatccg ggcctcatgt cgaa                                             24

<210> SEQ ID NO 4
<211> LENGTH: 59
<212> TYPE: DNA
<213> ORGANISM: Artificial sequence
<220> FEATURE:
<223> OTHER INFORMATION: synthetic

<400> SEQUENCE: 4
gggctcctct agtgaaggca gagaaaggtc gatacggacg gaatgtgatg gccggatcc       59
```

<210> SEQ ID NO 5
<211> LENGTH: 24
<212> TYPE: DNA
<213> ORGANISM: Artificial sequence
<220> FEATURE:
<223> OTHER INFORMATION: synthetic

<400> SEQUENCE: 5
attcgcaaga tgtggcgtgt tacg                                          24

<210> SEQ ID NO 6
<211> LENGTH: 24
<212> TYPE: DNA
<213> ORGANISM: Artificial sequence
<220> FEATURE:
<223> OTHER INFORMATION: synthetic

<400> SEQUENCE: 6
actggtgaaa ctcacccagg gatt                                          24

<210> SEQ ID NO 7
<211> LENGTH: 24
<212> TYPE: DNA
<213> ORGANISM: Artificial sequence
<220> FEATURE:
<223> OTHER INFORMATION: synthetic

<400> SEQUENCE: 7
tgctgctgaa ggcgaaatga aagg                                          24

<210> SEQ ID NO 8
<211> LENGTH: 24
<212> TYPE: DNA
<213> ORGANISM: Artificial sequence
<220> FEATURE:
<223> OTHER INFORMATION: synthetic

<400> SEQUENCE: 8
agcatcgaac acggaagtgc aaac                                          24

<210> SEQ ID NO 9
<211> LENGTH: 97
<212> TYPE: RNA
<213> ORGANISM: Artificial sequence
<220> FEATURE:
<223> OTHER INFORMATION: synthetic

<400> SEQUENCE: 9
gggagcucag aauaaacgcu caacuccugu agugaaggca gagaaagguc gauacggacg    60
gaaugugaug gccuucgaca ucaggcccgg auccggc                            97

<210> SEQ ID NO 10
<211> LENGTH: 51
<212> TYPE: RNA
<213> ORGANISM: Artificial sequence
<220> FEATURE:
<223> OTHER INFORMATION: synthetic

<400> SEQUENCE: 10
ggauccaggc agagaaaggu cgauacggac ggaaugugau ggccuggauc c             51

<210> SEQ ID NO 11
<211> LENGTH: 51
<212> TYPE: RNA

<213> ORGANISM: Artificial sequence
<220> FEATURE:
<223> OTHER INFORMATION: synthetic

<400> SEQUENCE: 11
ggauccaggc aguguaaggu cgauacggac ggaaugugau ggccuggauc c        51

<210> SEQ ID NO 12
<211> LENGTH: 97
<212> TYPE: RNA
<213> ORGANISM: Artificial sequence
<220> FEATURE:
<223> OTHER INFORMATION: synthetic

<400> SEQUENCE: 12
gggagcucag aauaaacgcu caacuccugu agugaaggca gagaaagguc gauacggacg    60
gaaugugaug gccuucgaca ucaggcccgg auccggc                            97

<210> SEQ ID NO 13
<211> LENGTH: 97
<212> TYPE: RNA
<213> ORGANISM: Artificial sequence
<220> FEATURE:
<223> OTHER INFORMATION: synthetic

<400> SEQUENCE: 13
gggagcugag aauaaacgcu caacaggaaa cagcaagaca aacgaugggg agcguaagac    60
ugcgaguguc ggauucgaca ucaggcccgg auccggc                            97

<210> SEQ ID NO 14
<211> LENGTH: 97
<212> TYPE: RNA
<213> ORGANISM: Artificial sequence
<220> FEATURE:
<223> OTHER INFORMATION: synthetic

<400> SEQUENCE: 14
gggagcugag aauaaacgcu caauaggag agaacugugu cagaauguag ugaaccagac    60
acggagugga guauucgaca ucaggcccgg auccggc                            97

<210> SEQ ID NO 15
<211> LENGTH: 97
<212> TYPE: RNA
<213> ORGANISM: Artificial sequence
<220> FEATURE:
<223> OTHER INFORMATION: synthetic

<400> SEQUENCE: 15
gggagcucag aauaaacgcu caacuugcug cagagggucg agaauaugug ugacacugcg    60
ucgacggguu aaguucgaca ucaggcccgg auccggc                            97

<210> SEQ ID NO 16
<211> LENGTH: 29
<212> TYPE: RNA
<213> ORGANISM: Artificial sequence
<220> FEATURE:
<223> OTHER INFORMATION: synthetic

<400> SEQUENCE: 16
cuuaagcuuc aacagugcuu gaacuuaag                                     29

<210> SEQ ID NO 17
<211> LENGTH: 50

```
<212> TYPE: RNA
<213> ORGANISM: Artificial sequence
<220> FEATURE:
<223> OTHER INFORMATION: synthetic

<400> SEQUENCE: 17
cuccucuagu gaaggcagag aaaggucgau acggacggaa ugugauggcc          50

<210> SEQ ID NO 18
<211> LENGTH: 50
<212> TYPE: RNA
<213> ORGANISM: Artificial sequence
<220> FEATURE:
<223> OTHER INFORMATION: synthetic

<400> SEQUENCE: 18
caacuacaug ucgacccuga gaaggcugug gaugugauua ggccaguugc          50

<210> SEQ ID NO 19
<211> LENGTH: 49
<212> TYPE: RNA
<213> ORGANISM: Artificial sequence
<220> FEATURE:
<223> OTHER INFORMATION: synthetic

<400> SEQUENCE: 19
gcagagaaag gguaaguaug augucuaccg gaaugugugg guuggugcg           49

<210> SEQ ID NO 20
<211> LENGTH: 49
<212> TYPE: RNA
<213> ORGANISM: Artificial sequence
<220> FEATURE:
<223> OTHER INFORMATION: synthetic

<400> SEQUENCE: 20
aacuagcagg cagagaagag ugggugcgac cacaggaugu uauggccug           49

<210> SEQ ID NO 21
<211> LENGTH: 50
<212> TYPE: RNA
<213> ORGANISM: Artificial sequence
<220> FEATURE:
<223> OTHER INFORMATION: synthetic

<400> SEQUENCE: 21
caaggcagaa uguaaugcug aauaagagag aaaaguguug gugaguguag          50

<210> SEQ ID NO 22
<211> LENGTH: 50
<212> TYPE: RNA
<213> ORGANISM: Artificial sequence
<220> FEATURE:
<223> OTHER INFORMATION: synthetic

<400> SEQUENCE: 22
caggaaacag caagacaaac gaugggagc guaagacugc gagugucgga           50

<210> SEQ ID NO 23
<211> LENGTH: 50
<212> TYPE: RNA
<213> ORGANISM: Artificial sequence
<220> FEATURE:
<223> OTHER INFORMATION: synthetic

<400> SEQUENCE: 23
```

```
ugguaggacg gcaccggaga aagguagcau gauaagcgag uaccugccgu              50

<210> SEQ ID NO 24
<211> LENGTH: 50
<212> TYPE: RNA
<213> ORGANISM: Artificial sequence
<220> FEATURE:
<223> OTHER INFORMATION: synthetic

<400> SEQUENCE: 24
uagggagaga acugugucag aauguaguga accagacacg gaguggagua              50

<210> SEQ ID NO 25
<211> LENGTH: 50
<212> TYPE: RNA
<213> ORGANISM: Artificial sequence
<220> FEATURE:
<223> OTHER INFORMATION: synthetic

<400> SEQUENCE: 25
agcgcgggau guuauggcac gauguguaga gaauagcgcu gaucgggcaa              50

<210> SEQ ID NO 26
<211> LENGTH: 50
<212> TYPE: RNA
<213> ORGANISM: Artificial sequence
<220> FEATURE:
<223> OTHER INFORMATION: synthetic

<400> SEQUENCE: 26
cuugcugcag aggguccaga auaugguga cacugcgucg acggguuaag               50

<210> SEQ ID NO 27
<211> LENGTH: 50
<212> TYPE: RNA
<213> ORGANISM: Artificial sequence
<220> FEATURE:
<223> OTHER INFORMATION: synthetic

<400> SEQUENCE: 27
gauguuucga auguugcggg ugagacacag caugacaaac uaccguguca              50

<210> SEQ ID NO 28
<211> LENGTH: 42
<212> TYPE: DNA
<213> ORGANISM: Artificial sequence
<220> FEATURE:
<223> OTHER INFORMATION: synthetic

<400> SEQUENCE: 28
ctggactttc acttttctct atcactgata gggagtggta aa                     42

<210> SEQ ID NO 29
<211> LENGTH: 50
<212> TYPE: RNA
<213> ORGANISM: Artificial sequence
<220> FEATURE:
<223> OTHER INFORMATION: synthetic

<400> SEQUENCE: 29
cuccucuagu gaaggcaauu cgaggucgau acggacggaa ugugauggcc              50

<210> SEQ ID NO 30
<211> LENGTH: 50
<212> TYPE: RNA
<213> ORGANISM: Artificial sequence
```

```
<220> FEATURE:
<223> OTHER INFORMATION: synthetic

<400> SEQUENCE: 30
cuccucuagu gaaggcagag aaaggucgau acggagauag gucgauggcc          50

<210> SEQ ID NO 31
<211> LENGTH: 50
<212> TYPE: RNA
<213> ORGANISM: Artificial sequence
<220> FEATURE:
<223> OTHER INFORMATION: synthetic

<400> SEQUENCE: 31
cuccucuagu gaaggccauu cgaggucgau acggagauag gucgauggcc          50

<210> SEQ ID NO 32
<211> LENGTH: 49
<212> TYPE: RNA
<213> ORGANISM: Artificial sequence
<220> FEATURE:
<223> OTHER INFORMATION: synthetic
<220> FEATURE:
<221> NAME/KEY: stem_loop
<222> LOCATION: (1)..(49)

<400> SEQUENCE: 32
gauccaggca gagaaagguc gauacggacg gaaugugaug gccuggauc           49

<210> SEQ ID NO 33
<211> LENGTH: 51
<212> TYPE: RNA
<213> ORGANISM: Artificial sequence
<220> FEATURE:
<223> OTHER INFORMATION: synthetic
<220> FEATURE:
<221> NAME/KEY: stem_loop
<222> LOCATION: (1)..(51)

<400> SEQUENCE: 33
ggauccaggc agagaaaggu cgauacggac ggaaugugau ggccuggauc c        51

<210> SEQ ID NO 34
<211> LENGTH: 49
<212> TYPE: RNA
<213> ORGANISM: Artificial sequence
<220> FEATURE:
<223> OTHER INFORMATION: synthetic
<220> FEATURE:
<221> NAME/KEY: stem_loop
<222> LOCATION: (1)..(47)
<220> FEATURE:
<221> NAME/KEY: stem_loop
<222> LOCATION: (1)..(47)
<223> OTHER INFORMATION: where n= any nucleotide
<220> FEATURE:
<221> NAME/KEY: misc_feature
<222> LOCATION: (8)..(16)
<223> OTHER INFORMATION: n is a, c, g, or u
<220> FEATURE:
<221> NAME/KEY: misc_feature
<222> LOCATION: (20)..(22)
<223> OTHER INFORMATION: n is a, c, g, or u
<220> FEATURE:
<221> NAME/KEY: misc_feature
<222> LOCATION: (24)..(24)
<223> OTHER INFORMATION: n is a, c, g, or u
<220> FEATURE:
<221> NAME/KEY: misc_feature
<222> LOCATION: (26)..(26)
<223> OTHER INFORMATION: n is a, c, g, or u
```

```
<220> FEATURE:
<221> NAME/KEY: misc_feature
<222> LOCATION: (30)..(38)
<223> OTHER INFORMATION: n is a, c, g, or u

<400> SEQUENCE: 34
auccggcnnn nnnnnnucgn nngngncggn nnnnnnnncc cuggauaaa            49

<210> SEQ ID NO 35
<211> LENGTH: 48
<212> TYPE: RNA
<213> ORGANISM: Artificial sequence
<220> FEATURE:
<223> OTHER INFORMATION: synthetic
<220> FEATURE:
<221> NAME/KEY: stem_loop
<222> LOCATION: (1)..(45)

<400> SEQUENCE: 35
uccaggcaga gaaaggucga uacggacgga augugauggc cuggaaaa             48

<210> SEQ ID NO 36
<211> LENGTH: 46
<212> TYPE: RNA
<213> ORGANISM: Artificial sequence
<220> FEATURE:
<223> OTHER INFORMATION: synthetic
<220> FEATURE:
<221> NAME/KEY: stem_loop
<222> LOCATION: (1)..(43)

<400> SEQUENCE: 36
ccaggcagag aaaggucgau acggacggaa ugugauggcc uggaaa               46
```

POST-TRANSCRIPTIONAL REGULATION OF RNA-RELATED PROCESSES USING ENCODED PROTEIN-BINDING RNA APTAMERS

STATEMENT OF GOVERNMENTAL SUPPORT

This invention was made with government support under grant number 5 T32 E507020 awarded by the National Institute Of Environmental Health Sciences. The government has certain rights in the invention.

FIELD OF THE INVENTION

The invention is related to the field of gene expression. In particular, methods and compositions are disclosed for specifically manipulating a mRNA target's translation, processing, splicing, degradation, editing, stabilization or localization in a cell or cell-free biological system by genetically encoding a high affinity regulatory protein binding site into the mRNA, wherein the regulatory protein's affinity to the binding site responds to the presence or absence of exogenous and/or endogenous regulatory ligands. Fusion proteins are also contemplated comprising a ligand inducible RNA-binding protein and a functional protein or protein domain.

BACKGROUND

As genome sequencing becomes increasingly routine, the ability to genetically manipulate organisms of interest has become indispensable in order to rigorously parse gene function. Whereas commonly used model organisms often have robust (although sometimes limited) options for controlling gene expression, these techniques are not always applicable in less commonly studied organisms. Meissner et al., "Molecular tools for analysis of gene function in parasitic microorganisms" *Appl Microbiol Biotechnol* 75:963-975 (2007). For example, RNA interference is only useful in cells possessing the requisite machinery. Hammond S. M., "Dicing and slicing: the core machinery of the RNA interference pathway" *FEBS Lett* 579:5822-5829 (2005); and Hannon G. J., "RNA interference" *Nature* 418:244-251 (2002). Further, transcriptional control requires detailed knowledge of protein components, regulatory sequences, and promoter architecture, which are often evolutionarily divergent. Borneman et al., "Divergence of transcription factor binding sites across related yeast species" *Science* 317:815-819 (2007); and Odom et al., "Tissue-specific transcriptional regulation has diverged significantly between human and mouse" *Nat Genet* 39:730-732 (2007). Techniques to make knockouts are sometimes available but are not always adaptable to studying essential genes. Furthermore, the study of newly discovered organisms would benefit significantly from experimenter-controlled regulatory systems that obviate extensive upfront characterization of their particular genetics. Beyond elucidating basic biology, a larger set of genetic control techniques will be required for building complex intracellular circuits, as is vital to the field of synthetic biology.

Since many mechanistic details of protein translation are highly conserved across different genera, protein translation is an attractive platform for designing modular, inducible gene expression systems. Bruell et al., "Conservation of bacterial protein synthesis machinery: initiation and elongation in *Mycobacterium smegmatis*" *Biochemistry* 47:8828-8839 (2008); and Kapp et al., "The molecular mechanics of eukaryotic translation" *Annu Rev Biochem* 73:657-704 (2004). In principle, these systems can be readily implemented in a wide variety of contexts. Nature provides numerous examples of post-transcriptional regulation, including: i) antisense (Good L., "Translation repression by antisense sequences" *Cell Mol Life Sci* 60:854-861 (2003)); ii) attenuation (Kolter et al., "Attenuation in amino acid biosynthetic operons" *Annu Rev Genet* 16:113-134 (1982); and iii) RNA interference (Mello et al., "Revealing the world of RNA interference" *Nature* 431:338-342 (2004)).

What is needed in the art are broadly-applicable methods to specifically control protein translation in a desired organism or cell-free biological system by the presence or absence of endogenous and/or exogenous ligands.

SUMMARY OF THE INVENTION

The invention is related to the field of gene expression. In particular, methods and compositions are disclosed for specifically manipulating a mRNA target's translation, processing, splicing, degradation, editing, stabilization or localization in a cell or cell-free biological system by genetically encoding a high affinity regulatory protein binding site into the mRNA, wherein the regulatory protein's affinity to the binding site responds to the presence or absence of exogenous and/or endogenous regulatory ligands. Fusion proteins are also contemplated comprising a ligand inducible RNA-binding protein and a functional protein or protein domain.

In one embodiment, the present invention contemplates a composition comprising a ribonucleic acid sequence in operable combination with an aptamer sequence, wherein the aptamer sequence comprises a protein binding site. In one embodiment, the aptamer sequence comprises an RNA aptamer sequence. In one embodiment, the protein binding site comprises a high affinity protein binding site. In one embodiment, the protein binding site comprises a stem loop. In one embodiment, the binding site comprises a Motif #1 nucleic acid sequence. In one embodiment, the binding site comprises a Motif #2 nucleic acid sequence. In one embodiment, the binding site comprises a regulatory protein binding site. In one embodiment, the regulatory protein binding site comprises a repressor protein binding site. In one embodiment, the regulatory binding site comprises an activator protein binding site. In one embodiment, the nucleic acid sequence comprises an open reading frame of a gene of interest.

In one embodiment, the present invention contemplates a complex comprising: a) a ribonucleic acid sequence comprising an untranslated region; b) at least one aptamer sequence comprising a protein binding site, wherein said aptamer sequence is encoded within the untranslated region; and c) a ligand-inducible protein attached to the protein binding site, wherein said protein's affinity to the protein binding site is modulated by a ligand. In one embodiment, the ribonucleic acid sequence comprises an open reading frame of a gene of interest. In one embodiment, the protein binding site is a high affinity binding site. In one embodiment, the ligand-inducible protein comprises a regulatory protein. In one embodiment, the regulatory protein comprises a repressor protein. In one embodiment, the repressor protein comprises a tetracycline-inducible repressor protein. In one embodiment, the untranslated region is a 3' untranslated region. In one embodiment, the untranslated region is a 5' untranslated region. In one embodiment, the open reading frame encodes a protein of interest.

In one embodiment, the present invention contemplates a plasmid comprising a gene of interest, wherein the gene of interest comprises an open reading frame encoding a protein of interest, wherein said open reading frame is in operable combination with a DNA sequence encoding an aptamer, wherein the aptamer comprises a binding site for a ligand inducible regulatory protein. In one embodiment, the protein binding site is a high affinity binding site. In one embodiment, the aptamer comprises an RNA aptamer. In one embodiment, the ligand-inducible protein comprises a regulatory protein. In one embodiment, the regulatory protein comprises a repressor protein. In one embodiment, the repressor protein comprises a tetracycline-inducible repressor protein. In one embodiment, the untranslated region is a 3' untranslated region. In one embodiment, the untranslated region is a 5' untranslated region.

In one embodiment, the present invention contemplates a method comprising: a) providing: i) a biological cell comprising a ribonucleic acid sequence encoding an open reading frame for a protein of interest; ii) an aptamer sequence in operable combination with the ribonucleic acid sequence, wherein the aptamer sequence comprises a protein binding site; iii) a protein comprising an affinity for said protein binding site, wherein the protein further comprises a ligand binding site; and iv) a ligand capable of binding to the ligand binding site, thereby modulating the affinity of said protein to said protein binding site; b) binding the protein to the protein binding site; and c) contacting the ligand binding site with the ligand under conditions that modulate translation of the protein of interest. In one embodiment, the protein binding site comprises a high affinity protein binding site. In one embodiment, the ligand binding site comprises a high affinity ligand binding site. In one embodiment, the ribonucleic acid sequence further comprises a 5' untranslated region. In one embodiment, the ribonucleic acid sequence further comprises a 3' untranslated region. In one embodiment, the aptamer sequence is located within the 5' untranslated region. In one embodiment, the aptamer sequence is located within the 3' untranslated region. In one embodiment, the protein binding site comprises a Motif #1 nucleic acid sequence. In one embodiment, the protein binding site comprises a Motif #2 nucleic acid sequence. In one embodiment, the protein binding site comprises a stem loop. In one embodiment, the ligand activates translation of the protein of interest. In one embodiment, the ligand reduces translation of the protein of interest. In one embodiment, the protein is a regulatory protein. In one embodiment, the regulatory protein is a repressor protein. In one embodiment, the repressor protein is a tetracycline repressor protein. In one embodiment, the regulatory protein is an activator protein. In one embodiment, the ligand is a tetracycline-based compound. In one embodiment, the tetracycline-based compound is tetracycline. In one embodiment, the tetracycline-based compound is anhydrotetracycline. In one embodiment, the biological cell further comprises a plasmid configured to express the protein.

In one embodiment, the present invention contemplates a method comprising: a) providing: i) a cell-free translation system comprising a ribonucleic acid sequence encoding an open reading frame for a protein of interest; ii) an aptamer sequence in operable combination with the ribonucleic acid sequence, wherein the aptamer sequence comprises a protein binding site; iii) a protein comprising a ligand binding site, wherein said protein has an affinity for the protein binding site; and v) a ligand having a high affinity for the ligand binding site thereby modulating the affinity of the protein for the protein binding site; b) binding the protein to the protein binding site; and b) contacting the ligand binding site with the ligand under conditions that modulate translation of the protein of interest. In one embodiment, the protein binding site comprises a high affinity ligand protein binding site. In one embodiment, the ligand binding site comprises a high affinity ligand binding site. In one embodiment, the ribonucleic acid sequence further comprises a 5' untranslated region. In one embodiment, the ribonucleic acid sequence further comprises a 3' untranslated region. In one embodiment, the aptamer sequence is located within the 5' untranslated region. In one embodiment, the aptamer sequence is located within the 3' untranslated region. In one embodiment, the protein binding site comprises a Motif #1 nucleic acid sequence. In one embodiment, the protein binding site comprises a Motif #2 nucleic acid sequence. In one embodiment, the protein binding site comprises a stem loop. In one embodiment, the ligand activates translation of the protein of interest. In one embodiment, the ligand reduces translation of the protein of interest. In one embodiment, the protein is a regulatory protein. In one embodiment, the regulatory protein is a repressor protein. In one embodiment, the repressor protein is a tetracycline repressor protein. In one embodiment, the regulatory protein is an activator protein. In one embodiment, the ligand is a tetracycline-based compound. In one embodiment, the tetracycline-based compound is tetracycline. In one embodiment, the tetracycline-based compound is anhydrotetracycline.

In one embodiment, the present invention contemplates a method comprising; i) a patient comprising a plurality of biological cells, wherein the patient exhibits at least one symptom of a medical condition; ii) a composition comprising a first plasmid encoding a ribonucleic acid sequence in operable combination with an aptamer sequence, wherein the aptamer sequence comprises a protein binding site, a second plasmid encoding a regulatory protein capable of binding to the protein binding site, wherein the regulatory protein comprises a ligand binding site, and a ligand capable of binding to the ligand binding site; and b) administering the composition to the patient under conditions such that at least one symptom is reduced. In one embodiment, the protein binding site comprises a high affinity protein binding site. In one embodiment, the ligand binding site comprises a high affinity ligand binding site. In one embodiment, the ribonucleic acid further comprises an open reading frame encoding a protein of interest. In one embodiment, the ligand modulates translation of the protein of interest. In one embodiment, the translation of the protein of interest is increased. In one embodiment, the translation of the protein of interest is decreased.

In one embodiment, the present invention contemplates a kit comprising: a) a first container comprising a first plasmid encoding a ribonucleic acid sequence in operable combination with an aptamer sequence, wherein the ribonucleic acid sequence comprises a protein binding site; b) a second container comprising a second plasmid encoding a regulatory protein capable of binding to the protein binding site, wherein the regulatory protein comprises a ligand binding site; c) a third container comprising a ligand capable of binding to the ligand binding site; and d) instructions describing how to use the first, second, and third containers. In one embodiment, the protein binding site comprises a high affinity protein binding site. In one embodiment, the ligand binding site comprises a high affinity ligand binding site. In one embodiment, the kit further comprises a fourth container comprising buffers and reagents compatible with the first plasmid, second plasmid, and ligand. In one embodiment, the instructions describe the administration of the first plasmid, second plasmid, and ligand to a patient exhibiting at least one symptom of a medical condition. In one embodiment, the ribonucleic acid further comprises an open reading frame encoding a protein of interest. In one embodiment, the ligand modulates translation of the protein of interest. In one embodiment, the translation of the protein of interest is increased. In one embodiment, the translation of the protein of interest is decreased.

In one embodiment, the present invention contemplates a system comprising: a) an RNA sequence that is capable of binding to a protein target of interest thereby forming an aptamer; b) a repressor protein capable of binding to said aptamer; and c) a regulatory molecule capable of interacting with the repressor protein, thereby altering its interaction with the aptamer. In one embodiment, the RNA sequence binding to the protein target is a high affinity binding. In one embodiment, the repressor protein binding to the aptamer is a high affinity binding. In one embodiment, the RNA comprises noncoding RNA. In one embodiment, the noncoding RNA comprises regulatory RNA. In one embodiment, the RNA binds a specific intracellular target. In one embodiment, the RNA binds a specific extracellular target. In one embodiment, the repressor protein is produced within a cell. In one embodiment, the repressor protein is added to a cell-free biological system. In one embodiment, the repressor protein possesses subcellular localization activity. In one embodiment, the repressor protein comprises mRNA degradation activity. In one embodiment, the repressor protein modulates mRNA expression. In one embodiment, the repressor protein modulates RNA processing. In one embodiment, the repressor protein modulates RNA modification. In one embodiment, the repressor protein modulates RNA nuclear export. In one embodiment, the repressor protein modulates RNA splicing. In one embodiment, the regulatory RNA sequence is added in single copy to a 5' or 3' untranslated region of said gene, thereby forming a simple aptamer. In one embodiment, the regulatory RNA sequence is added in multiple copy to a 5' or 3' untranslated region of said gene, there by forming a complex aptamer. In one embodiment, the regulatory molecule comprises an exogenous compound and/or agent selected from the group including, but not limited to, small molecules, proteins, nucleic acids, lipids, or saccharides. In one embodiment, the regulatory molecule comprises an endogenous compound and/or agent selected from the group including, but not limited to, small molecules, proteins, nucleic acids, lipids, or saccharides. In one embodiment, the aptamer is formed within a cellular environment. In one embodiment, the aptamer is formed within a cell-free system. In one embodiment, the aptamer activates ribosomal translation of the downstream mRNA into protein in the presence of repressor protein binding. In one embodiment, the aptamer permits ribosomal translation of the downstream mRNA into protein in the absence of repressor protein binding. In one embodiment, the aptamer inhibits ribosomal translation of the downstream mRNA into protein in the presence of repressor protein binding. In one embodiment, the aptamer inhibits ribosomal translation of the downstream mRNA into protein in the absence of repressor protein binding. In one embodiment, the ribosomal translation is regulated by the regulatory molecule. In one embodiment, the gene expression is regulated by the regulatory molecule. In one embodiment, the repressor protein is a bacterial tetracycline repressor protein or a variant thereof. In one embodiment, the aptamer is selected from a group of aptamers having high bacterial tetracycline repressor protein binding affinity. In one embodiment, the regulatory molecule is selected from the group comprising a tetracycline derivative (i.e., for example, anhydrotetracycline) and/or a doxycycline derivative. Although it is not necessary to understand the mechanism of an invention, it is believed that addition of a tetracycline derivative relieves binding of the tetracycline repressor protein to the aptamer thereby enhancing translation of the downstream coding sequence. It is further believed that if a tetracycline repressor protein variant (i.e., for example, a reverse tetracycline repressor protein) is used, addition of a tetracycline derivative enhances binding of a reverse tetracycline repressor protein to the aptamer thereby reducing translation of the downstream coding sequence.

DEFINITIONS

The term "aptamer" as used herein, refers to any nucleic acid sequence having at least one binding site for another nucleic acid sequence, protein, peptide, antibody, small organic molecule, or mineral. The aptamer binding site may result from secondary, tertiary, or quaternary conformational structure. For example, an aptamer may be part of a ribonucleic acid sequence, wherein a binding site comprises a stem loop conformation.

The term "high affinity binding site" as used herein, refers to an aptamer binding site that binds another nucleic acid sequence, protein, peptide, antibody, small organic molecule, or mineral with a disassociation constant ($K_d$) of less than $10^{-6}$ M.

The term "stem loop" as used herein, refers to the predicted secondary structure of an aptamer high affinity binding site comprising at least one single stranded region and at least one hybridized duplex region. For example, a stem loop may have multiple single stranded regions either at the distal end of the stem loop or placed within the hybridized duplex region. Further, the single stranded and hybridized duplex regions may be of various sizes within a single stem loop conformation. See FIG. 2C and FIG. 2D for various possible embodiments.

The term "regulatory protein" as used herein, refers to any amino acid sequence comprising a function that modifies the transcription and/or translation rates of deoxyribonucleic and/or ribonucleic acid sequences. For example, a regulatory protein may also be referred to as a transcription factor, usually described as having effects on a gene promoter regions. Regulatory proteins may either increase transcription/ translation rates (i.e., for example, an activator protein) or decrease transcription/translation rates (i.e., for example, a repressor protein).

The term "open reading frame" as used herein, refers to any nucleic acid sequence that can be transcribed and translated. For example, an open reading frame capable of being transcribed may be encoded within a deoxyribonucleic acid sequence, whereas an open reading frame capable of being translated may be encoded within a ribonucleic acid sequence.

The term "gene of interest" as used herein refers to any deoxyribonucleic acid sequence encoding an open reading frame encoding "a protein of interest".

The term "untranslated region" as used herein, refers to a 3' untranslated region (UTR) or a 5' UTR encoded into either a deoxyribonucleic acid sequence or a ribonucleic acid sequence. As the term implies, a UTR would not be expected to encode an open reading frame, but does contain nucleic acid sequences for binding of, for example, regulatory proteins. Further, a UTR may comprise an aptamer that encodes a binding site for a heterologous regulation protein (i.e., for example, a ligand-inducible regulatory protein).

The term "ligand-inducible protein" as used herein, refers to any protein comprising a ligand binding site, wherein the formation of the ligand-protein complex results a change in function of the protein. For example, a ligand-inducible repressor protein may bind tetracycline whereby the ability of the repressor protein to bind to a nucleic acid sequence is decreased. Consequently, the repressive function of the repressor protein is decreased such that the transcription and/or translation of a gene of interest may be increased.

The term "ligand" as used herein, refers to any compound capable of binding to a molecule such that the conformation and/or function of the molecule is changed. For example, a ligand may bind to a nucleic acid sequence or an amino acid sequence under conditions such that the secondary, tertiary, or quaternary structure of the nucleic acid or amino acid sequence is changed. Although it is not necessary to understand the mechanism of an invention, it is believed that where the nucleic acid and/or amino acid sequences comprise active sites, conformation changes induced by ligand binding would be expected to alter the spatial arrangements of the functional groups within these active sites.

The term "ligated", "ligating", or "ligation" as used herein, refers to the formation of a phosphodiester bond between at least two nucleic acids such that they become part of the same molecule. For example, when a nucleic acid aptamer sequence is ligated within a ribonucleic acid sequence, the aptamer sequence is in operable combination with the ribonucleic acid sequence (i.e., for example, the ribonucleic acid sequence "encodes" the aptamer sequence").

The term "in operable combination" as used herein, refers to any linkage of nucleic acid sequences in such a manner that a nucleic acid molecule capable of directing the transcription of a given gene and/or the synthesis of a desired protein molecule is produced. Regulatory sequences may be operably combined to an open reading frame including but not limited to initiation signals such as start (i.e., ATG) and stop codons, promoters which may be constitutive (i.e., continuously active) or inducible, as well as enhancers to increase the efficiency of expression, and transcription termination signals.

The term "encode", "encoding", "encoded" as used herein, refers to any capability of carrying specific information within a nucleic acid sequence for a specific purpose. For example, an aptamer may be encoded to provide a high affinity ligand-inducible repressor protein binding site to regulate translation of a messenger ribonucleic acid sequence. Alternatively, an open reading frame may be encoded within a messenger ribonucleic acid sequence such that the open reading frame may be translated into a protein and released into the intracellular space.

The term "modulate translation" as used herein, refers to any change in translation rate of a messenger ribonucleic acid sequence. For example, translation modulation may result from, for example, steric hindrance of ribosome/mRNA binding, reduced or increased transcription rates resulting in reduced or increased levels of mRNA transcripts.

The term "biological cell" as used herein, refers to any a small, usually microscopic, mass of protoplasm bounded externally by a semipermeable membrane, usually including one or more nuclei and various nonliving products, capable alone or interacting with other cells of performing all the fundamental functions of life, and forming the smallest structural unit of living matter capable of functioning independently.

The term "cell-free translation system" as used herein, refers to any combination of intracellular components capable of generating proteins in an in vitro environment. For example, such systems usually contain ribosomes, ribonucleic acids, amino acids, regulatory proteins, and minerals whose interactions support the ability of the ribonucleic acids to attach to the ribosome and form peptide bonds between amino acids. For example, one cell-free translation system may be created from the lysate of rabbit reticulocyte cells.

The term "at risk for" as used herein, refers to a medical condition or set of medical conditions exhibited by a patient which may predispose the patient to a particular disease or affliction. For example, these conditions may result from influences that include, but are not limited to, behavioral, emotional, chemical, biochemical, or environmental influences.

The term "effective amount" as used herein, refers to a particular amount of a pharmaceutical composition comprising a therapeutic agent that achieves a clinically beneficial result (i.e., for example, a reduction of symptoms). Toxicity and therapeutic efficacy of such compositions can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The term "symptom", as used herein, refers to any subjective or objective evidence of disease or physical disturbance observed by the patient. For example, subjective evidence is usually based upon patient self-reporting and may include, but is not limited to, pain, headache, visual disturbances, nausea and/or vomiting. Alternatively, objective evidence is usually a result of medical testing including, but not limited to, body temperature, complete blood count, lipid panels, thyroid panels, blood pressure, heart rate, electrocardiogram, tissue and/or body imaging scans.

The term "disease" or "medical condition", as used herein, refers to any impairment of the normal state of the living animal or plant body or one of its parts that interrupts or modifies the performance of the vital functions. Typically manifested by distinguishing signs and symptoms, it is usually a response to: i) environmental factors (as malnutrition, industrial hazards, or climate); ii) specific infective agents (as worms, bacteria, or viruses); iii) inherent defects of the organism (as genetic anomalies); and/or iv) combinations of these factors The terms "reduce," "inhibit," "diminish," "suppress," "decrease," "prevent" and grammatical equivalents (including "lower," "smaller," etc.) when in reference to the expression of any symptom in an untreated subject relative to a treated subject, mean that the quantity and/or magnitude of the symptoms in the treated subject is lower than in the untreated subject by any amount that is recognized as clinically relevant by any medically trained personnel. In one embodiment, the quantity and/or magnitude of the symptoms in the treated subject is at least 10% lower than, at least 25% lower than, at least 50% lower than, at least 75% lower than, and/or at least 90% lower than the quantity and/or magnitude of the symptoms in the untreated subject.

The term "inhibitory compound" as used herein, refers to any compound capable of interacting with (i.e., for example, attaching, binding etc) to a binding partner under conditions such that the binding partner becomes unresponsive to its natural ligands Inhibitory compounds may include, but are not limited to, small organic molecules, antibodies, and proteins/peptides.

The term "drug" or "compound" as used herein, refers to any pharmacologically active substance capable of being administered which achieves a desired effect. Drugs or compounds can be synthetic or naturally occurring, non-peptide, proteins or peptides, oligonucleotides or nucleotides, polysaccharides or sugars.

The term "administered" or "administering", as used herein, refers to any method of providing a composition to a patient such that the composition has its intended effect on the patient. For example, one method of administering is by an indirect mechanism using a medical device such as, but not limited to a catheter, applicator gun, syringe etc. A second exemplary method of administering is by a direct mechanism such as, local tissue administration (i.e., for example, extravascular placement), oral ingestion, transdermal patch, topical, inhalation, suppository etc.

The term "patient", as used herein, is a human or animal and need not be hospitalized. For example, out-patients, persons in nursing homes are "patients." A patient may comprise any age of a human or non-human animal and therefore includes both adult and juveniles (i.e., children). It is not intended that the term "patient" connote a need for medical treatment. Therefore, a patient may voluntarily or involuntarily be part of experimentation whether clinical or in support of basic science studies.

The term "affinity" as used herein, refers to any attractive force between substances or particles that causes them to enter into and remain in chemical combination. For example, an inhibitor compound that has a high affinity for a receptor will provide greater efficacy in preventing the receptor from interacting with its natural ligands, than an inhibitor with a low affinity.

The term "derived from" as used herein, refers to the source of a compound or sequence. In one respect, a compound or sequence may be derived from an organism or particular species. In another respect, a compound or sequence may be derived from a larger complex or sequence.

The term "protein" as used herein, refers to any of numerous naturally occurring extremely complex substances (as an enzyme or antibody) that consist of amino acid residues joined by peptide bonds, contain the elements carbon, hydrogen, nitrogen, oxygen, usually sulfur. In general, a protein comprises amino acids having an order of magnitude within the hundreds.

The term "peptide" as used herein, refers to any of various amides that are derived from two or more amino acids by combination of the amino group of one acid with the carboxyl group of another and are usually obtained by partial hydrolysis of proteins. In general, a peptide comprises amino acids having an order of magnitude with the tens.

The term "pharmaceutically" or "pharmacologically acceptable", as used herein, refer to molecular entities and compositions that do not produce adverse, allergic, or other untoward reactions when administered to an animal or a human.

The term, "pharmaceutically acceptable carrier", as used herein, includes any and all solvents, or a dispersion medium including, but not limited to, water, ethanol, polyol (for example, glycerol, propylene glycol, and liquid polyethylene glycol, and the like), suitable mixtures thereof, and vegetable oils, coatings, isotonic and absorption delaying agents, liposome, commercially available cleansers, and the like. Supplementary bioactive ingredients also can be incorporated into such carriers.

The term, "purified" or "isolated", as used herein, may refer to a peptide composition that has been subjected to treatment (i.e., for example, fractionation) to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the composition (i.e., for example, weight/weight and/or weight/volume). The term "purified to homogeneity" is used to include compositions that have been purified to 'apparent homogeneity" such that there is single protein species (i.e., for example, based upon SDS-PAGE or HPLC analysis). A purified composition is not intended to mean that some trace impurities may remain.

As used herein, the term "substantially purified" refers to molecules, either nucleic or amino acid sequences, that are removed from their natural environment, isolated or separated, and are at least 60% free, preferably 75% free, and more preferably 90% free from other components with which they are naturally associated. An "isolated polynucleotide" is therefore a substantially purified polynucleotide.

"Nucleic acid sequence" and "nucleotide sequence" as used herein refer to an oligonucleotide or polynucleotide, and fragments or portions thereof, and to DNA or RNA of genomic or synthetic origin which may be single- or double-stranded, and represent the sense or antisense strand.

The term "an isolated nucleic acid", as used herein, refers to any nucleic acid molecule that has been removed from its natural state (e.g., removed from a cell and is, in a preferred embodiment, free of other genomic nucleic acid).

The terms "amino acid sequence" and "polypeptide sequence" as used herein, are interchangeable and to refer to a sequence of amino acids.

As used herein the term "portion" when in reference to a protein (as in "a portion of a given protein") refers to fragments of that protein. The fragments may range in size from four amino acid residues to the entire amino acid sequence minus one amino acid.

The term "portion" when used in reference to a nucleotide sequence refers to fragments of that nucleotide sequence. The fragments may range in size from 5 nucleotide residues to the entire nucleotide sequence minus one nucleic acid residue.

The term "antibody" refers to immunoglobulin evoked in animals by an immunogen (antigen). It is desired that the antibody demonstrates specificity to epitopes contained in the immunogen. The term "polyclonal antibody" refers to immunoglobulin produced from more than a single clone of plasma cells; in contrast "monoclonal antibody" refers to immunoglobulin produced from a single clone of plasma cells.

The terms "specific binding" or "specifically binding" when used in reference to the interaction of an aptamer and a protein or peptide, or an aptamer and a non-protein ligand means that the interaction is dependent upon the presence of a particular structure (i.e., for example, an antigenic determinant or epitope) on a protein or non-protein ligand; in other words an aptamer is recognizing and binding to a specific protein or small molecule structure rather than to proteins or small molecules in general. For example, if an aptamer is specific for binding to "A", when placed in a mixture of labeled "A" and an excess quantity of unlabeled other proteins or small molecules, the aptamer will deplete the amount of unbound labeled "A".

The term "small organic molecule" as used herein, refers to any molecule of a size comparable to those organic molecules generally used in pharmaceuticals. The term excludes biological macromolecules (e.g., proteins, nucleic acids, etc.). Preferred small organic molecules range in size from approximately 10 Da up to about 5000 Da, more preferably up to 2000 Da, and most preferably up to about 1000 Da.

As used herein, the term "antisense" is used in reference to RNA sequences which are complementary to a specific RNA sequence (e.g., mRNA). Antisense RNA may be produced by any method, including synthesis by splicing the gene(s) of interest in a reverse orientation to a viral promoter which permits the synthesis of a coding strand. Once introduced into a cell, this transcribed strand combines with natural mRNA produced by the cell to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

The term "sample" as used herein is used in its broadest sense and includes environmental and biological samples. Environmental samples include material from the environment such as soil and water. Biological samples may be animal, including, human, fluid (e.g., blood, plasma and serum), solid (e.g., stool), tissue, liquid foods (e.g., milk), and solid foods (e.g., vegetables). For example, a pulmonary sample may be collected by bronchoalveolar lavage (BAL) which comprises fluid and cells derived from lung tissues. A biological sample may comprise a cell, tissue extract, body fluid, chromosomes or extrachromosomal elements isolated from a cell, genomic DNA (in solution or bound to a solid support such as for Southern blot analysis), RNA (in solution or bound to a solid support such as for Northern blot analysis), cDNA (in solution or bound to a solid support) and the like.

The term "functionally equivalent codon", as used herein, refers to different codons that encode the same amino acid. This phenomenon is often referred to as "degeneracy" of the genetic code. For example, six different codons encode the amino acid arginine.

A "variant" of a protein is defined as an amino acid sequence which differs by one or more amino acids from a polypeptide sequence or any homolog of the polypeptide sequence. The variant may have "conservative" changes, wherein a substituted amino acid has similar structural or chemical properties, e.g., replacement of leucine with isoleucine. A variant may have "nonconservative" changes, e.g., replacement of a glycine with a tryptophan. Similar variations may also include amino acid deletions or insertions (i.e., additions), or both. Guidance in determining which and how many amino acid residues may be substituted, inserted or deleted without abolishing biological or immunological activity may be found using computer programs including, but not limited to, DNAStar® software.

A "variant" of a nucleotide is defined as a novel nucleotide sequence which differs from a reference oligonucleotide by having deletions, insertions and substitutions. These may be detected using a variety of methods (e.g., sequencing, hybridization assays etc.).

A "deletion" is defined as a change in either nucleotide or amino acid sequence in which one or more nucleotides or amino acid residues, respectively, are absent.

An "insertion" or "addition" is that change in a nucleotide or amino acid sequence which has resulted in the addition of one or more nucleotides or amino acid residues.

A "substitution" results from the replacement of one or more nucleotides or amino acids by different nucleotides or amino acids, respectively.

The term "derivative" as used herein, refers to any chemical modification of a nucleic acid or an amino acid. Illustrative of such modifications would be replacement of hydrogen by an alkyl, acyl, or amino group. For example, a nucleic acid derivative would encode a polypeptide which retains essential biological characteristics.

The term "biologically active" refers to any molecule having structural, regulatory or biochemical functions. For example, biological activity may be determined, for example, by restoration of wild-type growth in cells lacking protein activity. Cells lacking protein activity may be produced by many methods (i.e., for example, point mutation and frameshift mutation). Complementation is achieved by transfecting cells which lack protein activity with an expression vector which expresses the protein, a derivative thereof, or a portion thereof.

As used herein, the terms "complementary" or "complementarity" are used in reference to "polynucleotides" and "oligonucleotides" (which are interchangeable terms that refer to a sequence of nucleotides) related by the base-pairing rules. For example, the sequence "5'-C-A-G-T," is complementary to the sequence "5'-A-C-T-G" Complementarity can be "partial" or "total." "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands has significant effects on the efficiency and strength of hybridization between nucleic acid strands. This is of particular importance in amplification reactions, as well as detection methods which depend upon binding between nucleic acids.

The terms "homology" and "homologous" as used herein in reference to nucleotide sequences refer to a degree of complementarity with other nucleotide sequences. There may be partial homology or complete homology (i.e., identity). A nucleotide sequence which is partially complementary, i.e., "substantially homologous," to a nucleic acid sequence is one that at least partially inhibits a completely complementary sequence from hybridizing to a target nucleic acid sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding the probe will not hybridize to the second non-complementary target.

The terms "homology" and "homologous" as used herein in reference to amino acid sequences refer to the degree of identity of the primary structure between two amino acid sequences. Such a degree of identity may be directed to a portion of each amino acid sequence, or to the entire length of the amino acid sequence. Two or more amino acid sequences that are "substantially homologous" may have at least 50% identity, preferably at least 75% identity, more preferably at least 85% identity, most preferably at least 95%, or 100% identity.

An oligonucleotide sequence which is a "homolog" is defined herein as an oligonucleotide sequence which exhibits greater than or equal to 50% identity to a sequence, when sequences having a length of 100 by or larger are compared.

Low stringency conditions comprise conditions equivalent to binding or hybridization at 42° C. in a solution consisting of 5×SSPE (43.8 g/l NaCl, 6.9 g/l NaH$_2$PO$_4$.H$_2$O and 1.85 g/l EDTA, pH adjusted to 7.4 with NaOH), 0.1% SDS, 5× Denhardt's reagent {50× Denhardt's contains per 500 ml: 5 g Ficoll (Type 400, Pharmacia), 5 g BSA (Fraction V; Sigma)} and 100 µg/ml denatured salmon sperm DNA followed by washing in a solution comprising 5×SSPE, 0.1% SDS at 42° C. when a probe of about 500 nucleotides in length. is employed. Numerous equivalent conditions may also be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol), as well as components of the hybridization solution may be varied to generate conditions of low stringency hybridization different from, but equivalent to, the above listed conditions. In addition, conditions which promote hybridization under conditions of high stringency (e.g., increasing the temperature of the hybridization and/or wash steps, the use of formamide in the hybridization solution, etc.) may also be used.

As used herein, the term "hybridization" is used in reference to the pairing of complementary nucleic acids using any process by which a strand of nucleic acid joins with a complementary strand through base pairing to form a hybridization complex. Hybridization and the strength of hybridization (i.e., the strength of the association between the nucleic acids) is impacted by such factors as the degree of complementarity between the nucleic acids, stringency of the conditions involved, the $T_m$ of the formed hybrid, and the G:C ratio within the nucleic acids.

As used herein the term "hybridization complex" refers to a complex formed between two nucleic acid sequences by virtue of the formation of hydrogen bounds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0$ t or $R_0$ t analysis) or between one nucleic acid sequence present in solution and another nucleic acid sequence immobilized to a solid support (e.g., a nylon membrane or a nitrocellulose filter as employed in Southern and Northern blotting, dot blotting or a glass slide as employed in in situ hybridization, including FISH (fluorescent in situ hybridization)).

As used herein, the term "$T_mg$" is used in reference to the "melting temperature." The melting temperature is the temperature at which a population of double-stranded nucleic acid molecules becomes half dissociated into single strands. As indicated by standard references, a simple estimate of the $T_m$ value may be calculated by the equation: $T_m=81.5+0.41$ (% G+C), when a nucleic acid is in aqueous solution at 1M NaCl. Anderson et al., "Quantitative Filter Hybridization" In: *Nucleic Acid Hybridization* (1985). More sophisticated computations take structural, as well as sequence characteristics, into account for the calculation of $T_mg$.

As used herein the term "stringency" is used in reference to the conditions of temperature, ionic strength, and the presence of other compounds such as organic solvents, under which nucleic acid hybridizations are conducted. "Stringency" typically occurs in a range from about $T_m$ to about 20° C. to 25° C. below $T_mg$. A "stringent hybridization" can be used to identify or detect identical polynucleotide sequences or to identify or detect similar or related polynucleotide sequences. For example, when fragments are employed in hybridization reactions under stringent conditions the hybridization of fragments which contain unique sequences (i.e., regions which are either non-homologous to or which contain less than about 50% homology or complementarity) are favored. Alternatively, when conditions of "weak" or "low" stringency are used hybridization may occur with nucleic acids that are derived from organisms that are genetically diverse (i.e., for example, the frequency of complementary sequences is usually low between such organisms).

As used herein, the term "amplifiable nucleic acid" is used in reference to nucleic acids which may be amplified by any amplification method. It is contemplated that "amplifiable nucleic acid" will usually comprise "sample template."

As used herein, the term "sample template" refers to nucleic acid originating from a sample which is analyzed for the presence of a target sequence of interest. In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

"Amplification" is defined as the production of additional copies of a nucleic acid sequence and is generally carried out using polymerase chain reaction. Dieffenbachg C. W. and G. S. Dvekslergg (1995) In: *PCR Primer, a Laboratory Manual*, Cold Spring Harbor Press, Plainview, N.Y.

As used herein, the term "polymerase chain reaction" ("PCR") refers to the method of K. B. Mullis U.S. Pat. Nos. 4,683,195 and 4,683,202, herein incorporated by reference, which describe a method for increasing the concentration of a segment of a target sequence in a mixture of genomic DNA without cloning or purification. The length of the amplified segment of the desired target sequence is determined by the relative positions of two oligonucleotide primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified". With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxy-ribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers; to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the terms "restriction endonucleases" and "restriction enzymes" refer to bacterial enzymes, each of which cut double-stranded DNA at or near a specific nucleotide sequence.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the term "an oligonucleotide having a nucleotide sequence encoding a gene" means a nucleic acid sequence comprising the coding region of a gene, i.e. the nucleic acid sequence which encodes a gene product. The coding region may be present in a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "regulatory element" refers to a genetic element which controls some aspect of the expression, for example, editing, splicing, degradation, stabilization, processing or subcellular localization of nucleic acid sequences. For example, a promoter is a regulatory element which facilitates the initiation of transcription of an operably linked coding region. Other regulatory elements are splicing signals, polyadenylation signals, termination signals, etc.

Transcriptional control signals in eukaryotes comprise "promoter" and "enhancer" elements. Promoters and enhancers consist of short arrays of DNA sequences that interact specifically with cellular proteins involved in transcription. Maniatis, T. et al., *Science* 236:1237 (1987). Promoter and enhancer elements have been isolated from a variety of eukaryotic sources including genes in plant, yeast, insect and mammalian cells and viruses (analogous control elements, i.e., promoters, are also found in prokaryotes). The selection of a particular promoter and enhancer depends on what cell type is to be used to express the protein of interest.

The presence of "splicing signals" on an expression vector often results in higher levels of expression of the recombinant transcript. Splicing signals mediate the removal of introns from the primary RNA transcript and consist of a splice donor and acceptor site. Sambrook, J. et al., In: *Molecular Cloning: A Laboratory Manual,* 2nd ed., Cold Spring Harbor laboratory Press, New York (1989) pp. 16.7-16.8. A commonly used splice donor and acceptor site is the splice junction from the 16S RNA of SV40.

The term "poly A site" or "poly A sequence" as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is isolated from one gene and placed 3' of another gene. Efficient expression of recombinant DNA sequences in eukaryotic cells involves expression of signals directing the efficient termination and polyadenylation of the resulting transcript. Transcription termination signals are generally found downstream of the polyadenylation signal and are a few hundred nucleotides in length.

The term "transfection" or "transfected" refers to the introduction of foreign DNA into a cell.

As used herein, the terms "nucleic acid molecule encoding", "DNA sequence encoding," and "DNA encoding" refer to the order or sequence of deoxyribonucleotides along a strand of deoxyribonucleic acid. The order of these deoxyribonucleotides determines the order of ribonucleotides in the mRNA and thus the order of amino acids along the polypeptide (protein) chain. The DNA sequence thus codes for the amino acid sequence.

The term "Southern blot" refers to the analysis of DNA on agarose or acrylamide gels to fractionate the DNA according to size, followed by transfer and immobilization of the DNA from the gel to a solid support, such as nitrocellulose or a nylon membrane. The immobilized DNA is then probed with a labeled oligodeoxyribonucleotide probe or DNA probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists. J. Sambrook et al. (1989) In: *Molecular Cloning: A Laboratory Manual*, Cold Spring Harbor Press, NY, pp 9.31-9.58.

The term "Northern blot" as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled oligodeoxyribonucleotide probe or DNA probe to detect RNA species complementary to the probe used. Northern blots are a standard tool of molecular biologists. J. Sambrook, J. et al. (1989) supra, pp 7.39-7.52.

The term "reverse Northern blot" as used herein refers to the analysis of DNA by electrophoresis of DNA on agarose gels to fractionate the DNA on the basis of size followed by transfer of the fractionated DNA from the gel to a solid support, such as nitrocellulose or a nylon membrane. The immobilized DNA is then probed with a labeled oligoribonuclotide probe or RNA probe to detect DNA species complementary to the ribo probe used.

As used herein the term "coding region" when used in reference to a structural gene refers to the nucleotide sequences which encode the amino acids found in the nascent polypeptide as a result of translation of a mRNA molecule. The coding region is bounded, in eukaryotes, on the 5' side by the nucleotide triplet "ATG" which encodes the initiator methionine and on the 3' side by one of the three triplets which specify stop codons (i.e., TAA, TAG, TGA).

As used herein, the term "structural gene" refers to a DNA sequence coding for RNA or a protein. In contrast, "regulatory genes" are structural genes which encode products which control the expression of other genes (e.g., transcription factors).

As used herein, the term "gene" means the deoxyribonucleotide sequences comprising the coding region of a structural gene and including sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' untranslated (5'UTR) sequences. The sequences which are located 3' or downstream of the coding region and which are present on the mRNA are referred to as 3' untranslated (3'UTR) sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into heterogeneous nuclear RNA (hnRNA); introns may contain regulatory elements such as enhancers. Introns are removed or "spliced out" from the nuclear or primary transcript; introns therefore are absent in the fully processed messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, post transcriptional cleavage and polyadenylation.

The term "label" or "detectable label" are used herein, to refer to any composition detectable by spectroscopic, photochemical, biochemical, immunochemical, electrical, optical or chemical means. Such labels include biotin for staining with labeled streptavidin conjugate, magnetic beads (e.g., Dynabeads®), fluorescent dyes (e.g., fluorescein, texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and labels such as colloidal gold or colored glass or plastic (e.g., polystyrene, polypropylene, latex, etc.) beads. Patents teaching the use of such labels include, but are not limited to, U.S. Pat. Nos. 3,817,837; 3,850,752; 3,939,350; 3,996,345; 4,277,437; 4,275,149; and 4,366,241 (all herein incorporated by reference). The labels contemplated in the present invention may be detected by many methods. For example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

The term "binding" as used herein, refers to any interaction between at least two compositions or compounds. Such binding may be, but is not limited to, non-covalent binding, covalent bonding, ionic bonding, Van de Waal forces or friction, and the like. An infection control composition is bound to a surface if it is impregnated, incorporated, coated, in suspension with, in solution with, mixed with, etc.

BRIEF DESCRIPTION OF THE FIGURES

FIG. 2A: Sequence alignment of the variable regions of tetracycline repressor protein-binding aptamers: 5-1[SEQ ID NO: 17], 5-2 [SEQ ID NO: 18], 5-4 [SEQ ID NO: 19], 5-11 [SEQ ID NO: 20], 5-12 [SEQ ID NO: 21], 5-14 [SEQ ID NO: 22], 5-16[SEQ ID NO: 23], 5-18 [SEQ ID NO: 24], 5-21 [SEQ ID NO: 25], 5-29 [SEQ ID NO: 26], 5-42 [SEQ ID NO: 27], and tetO [SEQ ID NO: 28].

FIG. 2B: Consensus sequences of Motif #1 (SEQ ID NO: 37) and Motif #2(SEQ ID NO: 38) in representative aptamers using the Multiple Expectation-Maximization for Motif Elicitation (MEME) algorithm.

FIG. 2C: Secondary structure prediction of aptamers 5-1 [SEQ ID NO: 17], 5-11 [SEQ ID NO: 20], and 5-12 [SEQ ID NO: 21].

FIG. 2D: Truncated versions [SEQ ID NO: 17, 20-21] with motifs highlighted as in FIG. 2A.

FIG. 3 presents exemplary data showing mutations of conserved sequence motifs that abolish the tetracycline repressor protein-aptamer interaction.

FIG. 3A: Variable region sequences of original [SEQ ID NO: 17] and mutated 5-1 aptamers [SEQ ID NO: 29 30, and 31].

FIG. 4A: A schematic view of one embodiment of a translation control system. For example, a tetracycline repressor protein interaction with an RNA aptamer binding in a 5' UTR gene region controls chloramphenicol acetyl transferase (CAT) translation. The ribosome is shown in yellow.

FIG. 4B: Growth curves for *E. coli* expressing the CAT construct with the indicated 5-1t aptamer or variant in a 5' UTR aptamer. Cells grown in media containing chloramphenicol.

FIG. 4C: Schematic of a 5' UTR of reporter construct with 5-1t and 5-1t/tetO aptamers (*=transcription start site).

FIG. 4D: Growth curves of 5-1t/tetO aptamer-containing *E. coli* cells incubated with chloramphenicol.

FIG. 10A: In the absence of a tetracycline analog (i.e., for example, anhydrotetracycline; brown pentagon), a tetracycline repressor protein (red) binds the aptamer-bearing mRNA (stem loop structure) with high affinity Although it is not necessary to understand the mechanism of an invention, it is believed that this inhibits translation by stabilizing the stem-loop structure of the aptamer and/or sterically blocking assembly of the 43S pre-ribosomal scanning complex (yellow ovals+black T).

FIG. 10B: Addition of anhydrotetracycline switches the tetracycline repressor protein to a low-affinity state thereby dissociating the protein from the mRNA, and relieving translational repression of the open reading frame (ORF–blue).

FIG. 12A: Luciferase signal in yeast relative to the +aTc condition for each construct tested, with both±repressor normalized independently. Error bars represent range of measurement.

FIG. 12B: Phenotypic analysis for 5-1.2 and mutant aptamer control of URA3 expression utilized with URA3 deficient-W303 yeast growth on uracil-deficient plates (−ura). Cells were grown in the absence of anhydrotetracycline (−aTc) or the presence of anhydrotetracycline (+aTc). Each spot is a ten-fold dilution of the previous spot.

FIG. 12C: Phenotypic analysis for 5-1.2 and mutant aptamer control of URA3 expression utilized with URA3 deficient-W303 yeast growth on a 5-fluoroorotic acid (5-FOA) containing plate. Cells were grown in the absence of anhydrotetracycline. Each spot is a ten-fold dilution of the previous spot.

DETAILED DESCRIPTION OF THE INVENTION

Figure 1:
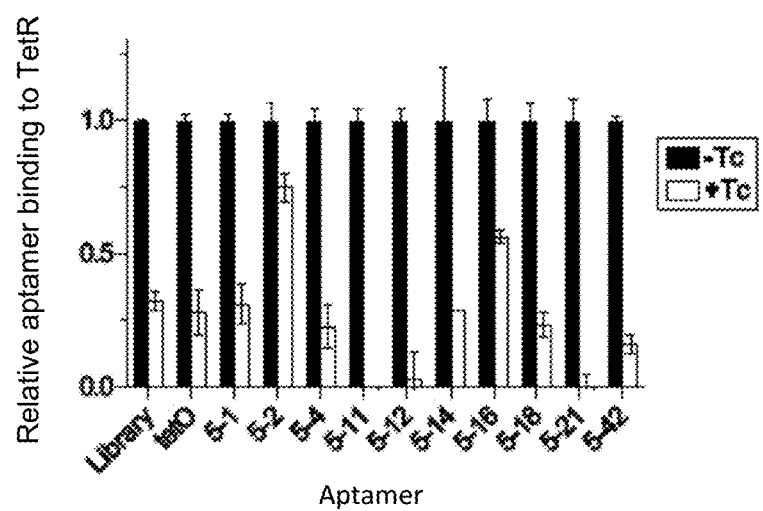
FIG. 1 presents exemplary data of selected aptamers binding to tetracycline repressor proteins in a tetracycline-dependent manner. The Library is a bulk RNA library after Round 5 of SELEX. tetO is dsDNA of the tet Operator sequence. Error bars show standard deviation from three independent experiments.

The invention is related to the field of gene expression. In particular, methods and compositions are disclosed for specifically manipulating a mRNA target's translation, processing, splicing, degradation, editing, stabilization or localization in a cell or cell-free biological system by genetically encoding a high affinity regulatory protein binding site into the mRNA, wherein the regulatory protein's affinity to the binding site responds to the presence or absence of exogenous and/or endogenous regulatory ligands. Fusion proteins are also contemplated comprising a ligand inducible RNA-binding protein and a functional protein or protein domain.

Robust, inducible gene expression systems remain limited for many organisms of biological, medical, and industrial interest. Without such techniques for controlling protein synthesis, it is difficult to elucidate protein function and basic biological mechanisms in these organisms. As many mechanistic details of protein translation are highly conserved, this process is an attractive target for constructing expandable and regulated gene expression systems. In some embodiments, the present invention contemplates methods for identifying metabolically orthogonal ligand-responsive RNA aptamer-protein interactions using the Systematic Evolution of Ligands by Exponential Enrichment (SELEX). Aptamers may be developed either by SELEX or by rational sequence design that selectively interact with the repressor protein in response to the presence or absence of the ligand to be added. This allows a coupling of gene expression within a cell or cell-free system to the level of an exogenous ligand, and gene expression is specifically regulated by the quantity of ligand present.

In some embodiments, the present invention contemplates expanding the scope of available translation regulation techniques by recapitulating pertinent aspects of an extensively characterized, naturally occurring example of protein-based inducible regulation. Jenner et al., "Translational operator of mRNA on the ribosome: how repressor proteins exclude ribosome binding" *Science* 308:120-123 (2005); and Nie et al., "Different modes and potencies of translational repression by sequence-specific RNA-protein interaction at the 5'-UTR" *Nucleic Acids Res* 34:5528-5540 (2006). One such naturally occurring regulatory system underlies mammalian iron storage and metabolism that is based on an interaction between an iron responsive element (IRE) RNA sequence and an IRE-Binding Protein (IRE-BP). Rouault T A., "The role of iron regulatory proteins in mammalian iron homeostasis and disease" *Nat Chem Biol* 2:406-414 (2006). An IRE stem-loop structure is found within the 5'-UTR of ferritin mRNA. Under low intracellular iron conditions, the IRE-BP associates with the IRE and represses translation initiation and, consequently, ferritin protein synthesis. When intracellular iron concentrations increase, the IRE-BP binds iron and undergoes a conformational change, thereby lowering its affinity for the IRE. Walden et al., "Structure of dual function iron regulatory protein 1 complexed with ferritin IRE-RNA" *Science* 314: 1903-1908 (2006). In the absence of the bound IRE-BP, translation initiation can occur efficiently, allowing ferritin protein synthesis to proceed. Adding to the versatility of the system, IREs are also found within the 3'-UTRs of other transcripts, such as that for the transferrin receptor. Casey et al., "Iron regulation of transferrin receptor mRNA levels requires iron-responsive elements and a rapid turnover determinant in the 3' untranslated region of the mRNA" *EMBO J* 8:3693-3699 (1989). In this case, binding of the IRE-BP increases translation by stabilizing the mRNA under iron-deficient conditions.

I. APTAMERS

Nucleic acid aptamers are believed to be nucleic acid species that have the ability to bind to specific molecular targets such as small molecules, proteins, nucleic acids, and even cells, tissues and organisms. These aptamers are often identified through repeated rounds of in vitro selection, or equivalently SELEX. Aptamers are useful in biotechnological and therapeutic applications as they may offer superior molecular recognition properties to that of antibodies in many instances. In addition to their discriminate recognition, aptamers offer advantages over antibodies as they can be engineered completely in vitro, can be produced by chemical synthesis, possess desirable storage properties, and elicit little or no immunogenicity in therapeutic applications.

In the past decade, several groups have sought to synthetically create RNA-based translation control devices using aptamers. Paraskeva et al., "A translational repression assay procedure (TRAP) for RNA-protein interactions in vivo" *Proc Natl Acad Sci USA* 95:951-956 (1998). TRAP is based on the translational repression of a reporter mRNA encoding green fluorescent protein by an RNA-binding protein for which a cognate binding site has been introduced into the 5' untranslated region. Because protein binding to the 5' untranslated region can sterically inhibit ribosome association, expression of the cognate binding protein causes significant reduction in the levels of green fluorescent protein fluorescence. By using RNA-protein interactions with affinities in the micromolar to nanomolar range, the specificity of TRAP as well as its ability to recover the cDNA encoding a specific RNA-binding protein, have been demonstrated. One disadvantage of using a TRAP-model is that this system cannot be modulated with exogenous ligands. For the most part, TRAP can be modulated with endogenous ligands (i.e., for example, Iron Responsive Protein) which is modulated by intracellular iron levels. Although it is not necessary to understand the mechanism of an invention, it is believed that exogenous ligands (i.e., for example, tetracycline) are more easily subjected to experimental control. Aptamers have also been referred to in the context of aptazymes. In general, aptazymes are referred to as RNA components with catalytic function, capable of regulating gene expression in vivo largely in bacteria and yeast. Isaacs et al., "RNA synthetic biology" *Nat Biotechnol* 24:545-554 (2006).

Aptamers that modulate gene expression by directly binding ligands have been referred to as riboswitches. Riboswitches have been reported to be structured domains that usually reside in the noncoding regions of mRNAs, where they directly bind metabolites and control gene expression. Like regulatory proteins, these RNA gene control elements form highly specific binding pockets for the target metabolite and undergo conformational (i.e., for example, structural) changes. Numerous classes of riboswitches are present in bacteria and they comprise a common and robust metabolite-sensing system. Winkler et al., "Regulation of bacterial gene expression by riboswitches" *Annu Rev Microbiol* 59:487-517 (2005); and Breaker et al., "Riboswitches, methods for their use, and compositions for use with riboswitches" United States Patent Application Publication No. 2005/0053951 (herein incorporated by reference). However, ligand-regulated ribozymes have been reported to be unable to control gene expression in particular contexts thereby suggesting that in vitro and in vivo folding pathways of RNA might be different. Link et al., "Engineering high-speed allosteric hammerhead ribozymes" *Biol Chem* 388: 779-786 (2007).

Aptamers that directly bind ligands are believed to induce conformational changes and have been recently reported to promote RNA destruction and/or slippage. Soukup et al., "Engineering precision RNA molecular switches" *Proc Natl Acad Sci USA* 96:3584-3589 (1999). For example, ligand-inducible RNA cleavage has been observed to promote RNA degradation. Win et al., "A modular and extensible RNA-based gene regulatory platform for engineering cellular function" *Proc Natl Acad Sci USA* 104:14283-14288 (2007); and Yen et al., "Exogenous control of mammalian gene expression through modulation of RNA self-cleavage" *Nature* 431 471-476 (2004).

Further, small molecule-RNA aptamer interactions have been reported to promote or repress protein translation. mRNA translation may be repressed upon direct tetracycline binding to an aptamer introduced into an mRNA 5' UTR. This technique exploits a direct RNA-ligand interaction and does not involve any protein factors. Kotter et al., "A fast and efficient translational control system for conditional expression of yeast genes" *Nucleic Acids Res* 37(18):e120 (2009). Translation of mRNAs was reduced upon direct tetracycline binding to the aptamer. This technique exploited a direct RNA-ligand interaction without the presence of other proteins. A similar technique also exploits direct RNA-metabolite interactions as a mechanism of genetic control. Preselected tetracycline binding aptamers were inserted into the 5'-UTR of a GFP encoding mRNA. While aptamer insertion generally reduces GFP expression, one group of aptamers decreased fluorescence an additional 6-fold in the presence of tetracycline. Suess et al., "Conditional gene expression by controlling translation with tetracycline-binding aptamers" Nucleic Acids Res 31:1853-1858 (2003).

Post-transcriptional regulation of gene expression using RNA molecules has also been attempted such that the insertion of an aptamer into the 5' UTR of an mRNA molecule forms a hairpin loop. This alteration in the structure of the mRNA blocks access to the ribosome, thereby preventing translation. Collins et al., "Cis/trans riboregulators" United States Patent Application Publication No. 2007/0136827 (herein incorporated by reference).

Ligand-inducible aptamers have been used to modify the expression of transcriptional regulatory polypeptides, such that the modulation of the intracellular concentration of the transcriptional regulatory polypeptides increase, or decrease, the gene expression of a protein of interest. Ramachandra, M., "Aptamer-mediated regulation of gene expression" United States Patent Application Publication No. 2006/0128649 (herein incorporated by reference).

II. GENE REGULATORY PROTEINS

A. Background

In Nature, binding of protein factors to conserved sequences in the untranslated regions (UTRs) of mRNAs can mediate post-transcriptional gene regulation. Stripecke et al., "Proteins binding to 5' untranslated region sites: a general mechanism for translational regulation of mRNAs in human and yeast cells" Mol. Cell. Biol. 14:5898-5909 (1994); and Gebauer et al., "Molecular mechanisms of translational control" Nat Rev Mol Cell Biol 5:827-835 (2004). Binding of protein factors to a UTR can confer stimulation or repression of translation, and may be regulated by intracellular conditions such as the concentration of labile iron. Rouault T. A., "The role of iron regulatory proteins in mammalian iron homeostasis and disease" Nat Chem Biol 2:406-414 (2006). Although recombinant systems regulating eukaryotic translation via protein-RNA interactions have been constructed, the protein-RNA interaction is either uninducible, or only potentially inducible by ubiquitous factors such as iron or tryptophan. Paraskeva et al., "A translational repression assay procedure (TRAP) for RNA-protein interactions in vivo" PNAS USA 95:951-956 (1998); and Nie et al., "Different modes and potencies of translational repression by sequence specific RNA-protein interaction at the 5'-UTR" Nucl. Acids Res. 34:5528-5540 (2006), respectively.

In some embodiments, the present invention contemplates protein-binding RNA aptamers that interact strongly and specifically with the bacterial tetracycline-responsive repressor protein (TetR), wherein this interaction is rapidly reversible by the addition of tetracycline analogs. Although it is not necessary to understand the mechanism of an invention, it is believed that this specific and ligand-reversible binding of RNA aptamer sequences to their cognate proteins provides an inducible post-transcriptional regulation (i.e., for example, regulation of translation) of a gene of interest (i.e., for example, a eukaryotic gene of interest).

B. Regulatory Protein Functionalization

In one embodiment, the present invention contemplates using protein-based systems for engineering an in vivo RNA control system. For example, it has been reported that tethering proteins and/or protein domains to reporter transcripts may be useful in determining biological function by constructing a fusion protein containing a viral RNA-binding protein (i.e. for example, MS2, or lambdaN), and concurrently inserting its specific binding aptamer into a transcript of interest. Coller et al., "Tethered function assays using 3' untranslated regions" Methods 26;142-150 (2002); Keryer-Bibens et al., "Tethering of proteins to RNAs by bacteriophage proteins. Biol. Cell 100, 125 (2008); and Baron-Benhamou et al., "Using the lambdaN peptide to tether proteins to RNAs" Methods Mol. Biol 257:135-154 (2004). These techniques constitutively target the protein fusion to the RNA, thereby allowing function of the tethered domain to be studied. These tethering techniques have significant downsides in that it does not allow for an active control of the system. Once expressed, the fusion protein will always target the RNA, without any straightforward way to specifically disrupt this interaction. Furthermore, while useful to characterize individual protein components, the techniques have not been used to engineer a new functionality within a cell.

Specific advantages of some embodiments of the present invention overcome these deficiencies by adding functionality to an inducible regulatory protein-aptamer interaction. For example, proteins and/or protein domains may be fused to a TetR which will effect specific RNA processes. Further, upon binding to a genetically-encoded aptamer located within an mRNA transcript of interest, the TetR construct can act locally upon that specific RNA. Another advantage of using this system is that the protein-RNA interaction is inducible, and thus can be modulated by the presence or absence of a ligand. In one embodiment, the present invention contemplates using an isogenic cell line, thereby reducing heterogeneity due to using identical or near-identical cells in order to measure the different phenotypic outcomes related to targeting or not targeting the protein and/or protein domain to a specific transcript. Also, the system can be incorporated into intracellular regulatory circuits, in a similar manner to currently used inducible promoter systems (i.e., for example, Tet or Lac). In addition to inducibility, enhancing regulatory proteins with a desired functionality in a systematic manner will enable a suite of regulated processes, all built upon a single underlying interaction. This ensures consistency in protein expression within cells and allows for comparing efficacy between specific heterologous protein domains added to a regulatory protein of interest.

A. RNA-Related Effector Protein Domains

One advantage of inducible regulatory protein-aptamer embodiments as disclosed herein, is that functionality in the system may be added by fusing functional protein domains and/or peptides onto the regulatory protein. Other currently used RNA control systems do not allow for protein and/or protein domain targeting and are usually limited to performing one specific function, such as RNA cleavage or base shifting. Isaacs et al., "RNA synthetic biology" Nat Biotech 24:545-554 (2006). Further, these present systems are extensively engineered to regulate each individual RNA process.

In one embodiment, the present invention contemplates a system wherein a regulatory RNA-binding protein (i.e., for example, a TetR protein) provides a platform for easily endowing desired functionality to the base RNA-aptamer interaction. Although it is not necessary to understand the mechanism of an invention, it is believed that since many RNA processes involve effector proteins, targeting these functional proteins and/or protein domains to an RNA with an inducible RNA-binding protein can achieve a similar effect. For example, the inducible nature of the TetR-aptamer systems described herein provides experimenter control of each targeted RNA process. Previously, proteins tethered to non-inducible RNA-binding proteins have been used to study the functional importance of these RNA-related factors. Coller et al., "Tethered function assays using 3' untranslated regions" *Methods* 26:142-150 (2002); Keryer-Bibens et al., "Tethering of proteins to RNAs by bacteriophage proteins" *Biol. Cell* 100:125 (2008); and Baron-Benhamou et al., "Using the lambdaN peptide to tether proteins to RNAs" *Methods Mol. Biol* 257:135-154 (2004). Thus, some embodiments of the present invention represent improvements to these previous methods to diversify the functionality of regulatory protein-aptamer interactions in an inducible manner.

1. Translation Initiation Repression Proteins

In one embodiment, the present invention contemplates a fusion protein comprising a ligand inducible regulatory protein and a protein and/or protein domain capable of preventing 5' cap translation initiation complex assembly. Although it is not necessary to understand the mechanism of an invention, it is believed that some embodiments of the translation repression methods described herein may reduce gene expression roughly 50-80%, as compared to previously reported systems. Nie et al., "Different modes and potencies of translational repression by sequence specific RNA-protein interaction at the 5'-UTR" *Nucl. Acids Res.* 34:5528-5540 (2006). It is further believed that such embodiments can provide a usable range of regulation for controlling cellular phenotypes or influencing intracellular circuits. For comparison, commonly used RNAi-based methods often achieve similar repression levels. Mello et al., "Revealing the world of RNA interference" *Nature* 431: 338-342 (2004). In one embodiment, the present invention contemplates an inducible regulatory protein-aptamer construct capable of repressing translation in human cells, wherein the magnitude of expression reduction is such that protein translation is effectively turned off for a transcript of interest, without being complicated by intermediate expression levels.

In one embodiment, the present invention contemplates a translation regulation system comprising an orthogonal functionality to a ligand inducible regulatory protein (i.e., for example, TetR), wherein the orthogonal functionality further decreases gene expression. In one embodiment, a functional protein is fused to the regulatory protein wherein ribosomal assembly is inhibited at the 5' cap. In one embodiment, the functional protein comprises a eIF4E protein. Although it is not necessary to understand the mechanism of an invention, it is believed that certain proteins and/or protein domains can prevent translation initiation factors from binding to the 5' cap, and thus inhibit the translation initiation process. Hinton et al., "Functional Analysis of Individual Binding Activities of the Scaffold Protein eIF4G" *J Biol Chem* 282:1695-1708 (2007); and Prévôt et al., "Conducting the initiation of protein synthesis: the role of eIF4G" *Biol. Cell* 95:141-156 (2003). One such eukaryotic protein which regulates this complex formation is the eIF4E binding protein (i.e., for example, 4E-BP). It is further believed that the 4E-BP-eIF4E interaction, blocks eIF4G from binding to the cap complex. Without 4E-BP, ribosomal loading onto the mRNA is prevented and the transcript is poorly translated. Gingras et al., "eIF4 initiation factors: effectors of mRNA recruitment to ribosomes and regulators of translation" *Annu. Rev. Biochem* 68:913-963 (1999).

Whereas 4E-BP causes a general decrease in translation among a large class of mRNA, eIF4E interacting proteins have also been shown to be targeted to specific transcripts in both *Drosophila melanogaster* and *Xenopus laevis*. Nelson et al., "*Drosophila* Cup is an eIF4E-binding protein that functions in Smaug-mediated translational repression" *EMBO J* 23:150-159 (2004); Stebbins-Boaz et al., "Maskin is a CPEB associated factor that transiently interacts with eIF-4E" *Mol. Cell* 4:1017-1027 (1999).

Figure 13:
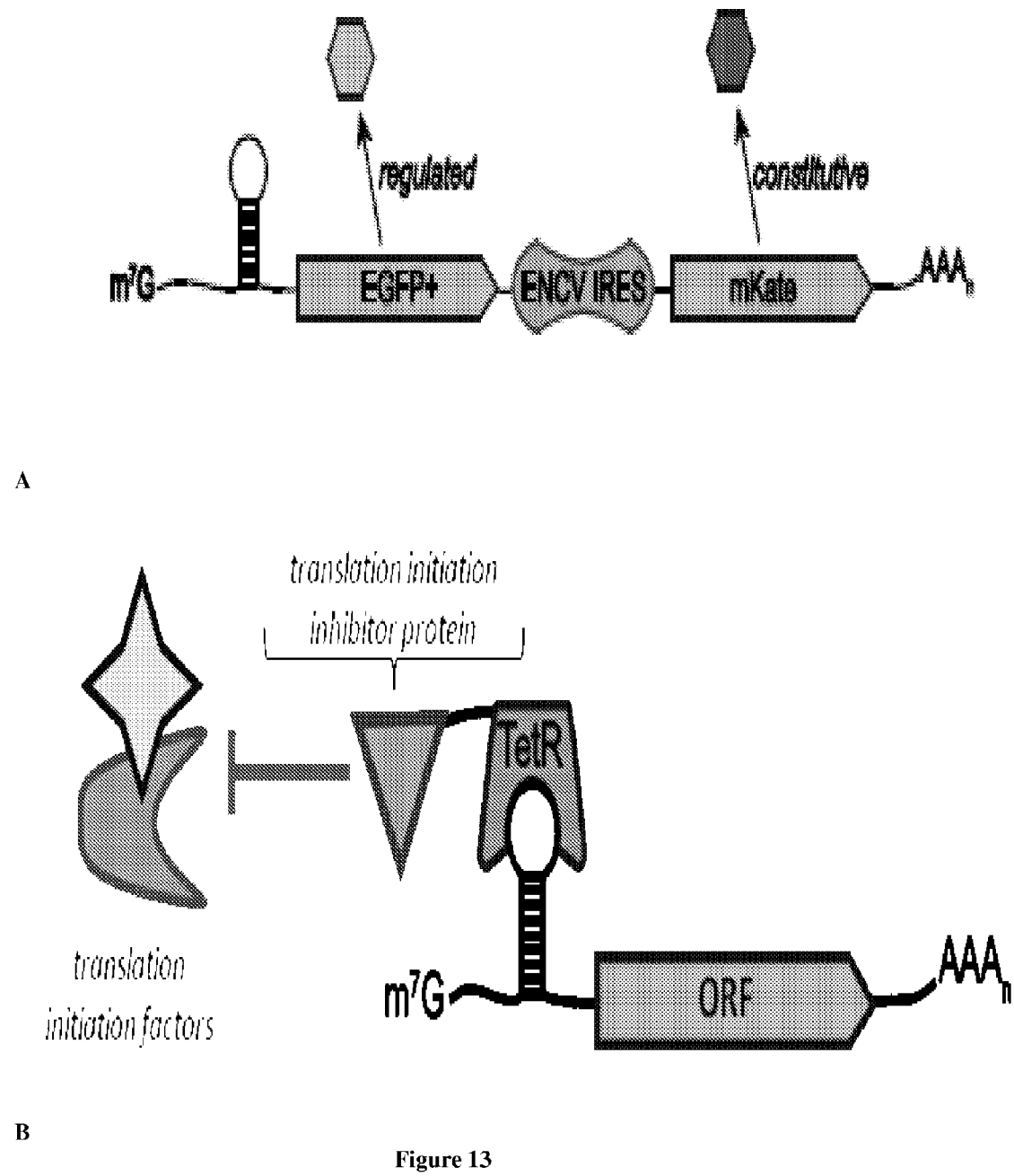
FIG. 13A presents one embodiment of a bicistronic reporter construct for measuring translation repression in human cells.
FIG. 13B presents one embodiment of an inducible TetR-aptamer mRNA functionalized with a translation initiation inhibitor protein.

In one embodiment, the present invention contemplates a method for fusing a translation initiation inhibition protein and/or protein domain to the C-terminus of TetR. In one embodiment, the translation initiation inhibition protein comprises an eIF4E protein. Although it is not necessary to understand the mechanism of an invention, it is believed that the TetR bound to the 5'-UTR aptamer causes the fused protein and/or protein domain to prevent initiation factor assembly on the specific transcript. See, FIG. 13B.

It has been reported that alignment of three human 4E-BP's shows a conserved sequence demonstrated to bind eIF4E. Marcotrigiano et al., "Cap-Dependent Translation Initiation in Eukaryotes Is Regulated by a Molecular Mimic of eIF4G. *Molecular Cell* 3:707-716 (1999); Poulin et al., "4E-BP3, a New Member of the Eukaryotic Initiation Factor 4E-binding Protein Family" *J Biol Chem* 273:14002-14007 (1998). In one embodiment, the present invention contemplates a composition comprising a 4E-BP consensus sequence attached to a ligand inducible regulatory protein (i.e., for example, TetR) wherein translation is further repressed. In one embodiment, the composition further comprises a portion of 4E-BP having specific affinity for eIF4E. Marcotrigiano et al., "Cap-Dependent Translation Initiation in Eukaryotes Is Regulated by a Molecular Mimic of eIF4G" *Molecular Cell* 3:707-716 (1999). In one embodiment, the composition further comprises a fragment of the eIF4G protein. Mader et al., "The translation initiation factor eIF-4E binds to a common motif shared by the translation factor eIF-4 gamma and the translational repressors 4E-binding proteins" *Mol. Cell. Biol* 15:4990-4997 (1995). In one embodiment, the composition further comprises a domain from a heterologous human eIF4E binding protein. Napoli et al., "The Fragile X Syndrome Protein Represses Activity-Dependent Translation through CYFIP1, a New 4E-BP" *Cell* 134:1042-1054 (2008). In one embodiment, the composition comprises at least one mutation in the eIF4E-binding peptide conserved residues, wherein affinity to eIF4E is reduced. Although it is not necessary to understand the mechanism of an invention, it is believed that a mutated conserved residue would increase specificity of the translation repression by relying upon avidity with the base regulatory protein-aptamer interaction. Stebbins-Boaz et al., "Maskin is a CPEB associated factor that transiently interacts with eIF-4E" *Mol. Cell* 4:1017-1027 (1999).

2. RNA Localization Proteins

Once transported to the intracellular space (i.e., for example, cytoplasm), certain mRNAs are believed to be actively transported to specific locations within a cell. This spatial control of mRNA may have functional consequences for processes such as budding in yeast, body segmentation during development, and synaptic stimulation in neuronal dendrites Beach et al., "ASH1 mRNA localization in three acts" *Mol. Biol. Cell* 12, 2567-2577 (2001); Bashirullah et al., "RNA localization in development." *Annu. Rev. Biochem* 67:335-394 (1998); Martin et al., "RNA Trafficking and Local Protein Synthesis in Dendrites: An Overview" *J. Neurosci.* 26:7131-7134 (2006), respectively. Again, one disadvantage of these reported systems is that (as with other conventional RNA-related processes) intracellular RNA localization cannot be inducibly controlled by endogenous and/or exogenous ligands. In one embodiment, the present invention contemplates a method comprising localizing RNA comprising a ligand inducible regulatory protein-aptamer complex in the presence or absence of a ligand having specific affinity for the regulatory protein For example, such a method would be useful in studying the significance of RNA trafficking within neurons on a single cell basis. In one embodiment, the single cell comprises a human single cell.

Figure 14:
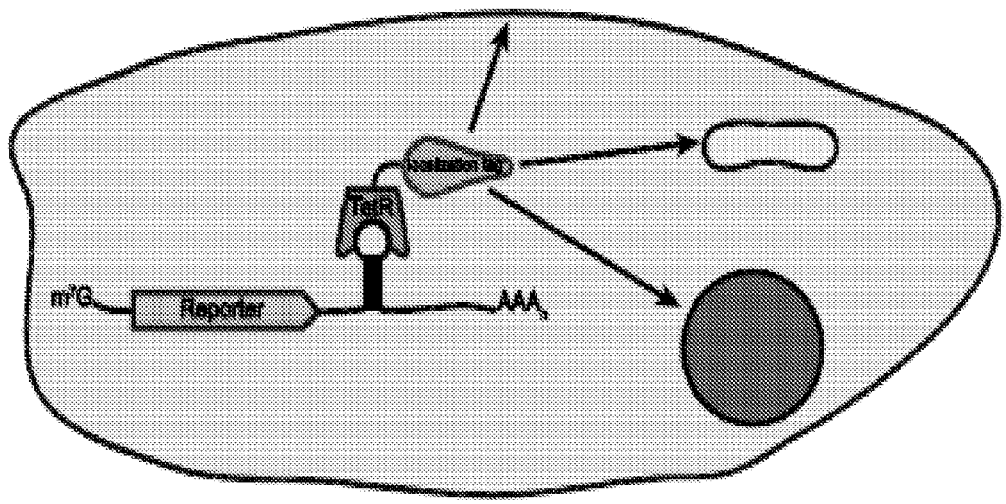
FIG. 14A presents an illustrative embodiment of an inducible TetR-aptamer mRNA functionalized with a localization signal protein.
FIG. 14B presents an illustrative embodiment of an inducible TetR-aptamer mRNA functionalized with a PAP inhibitor protein.
Figure 14:
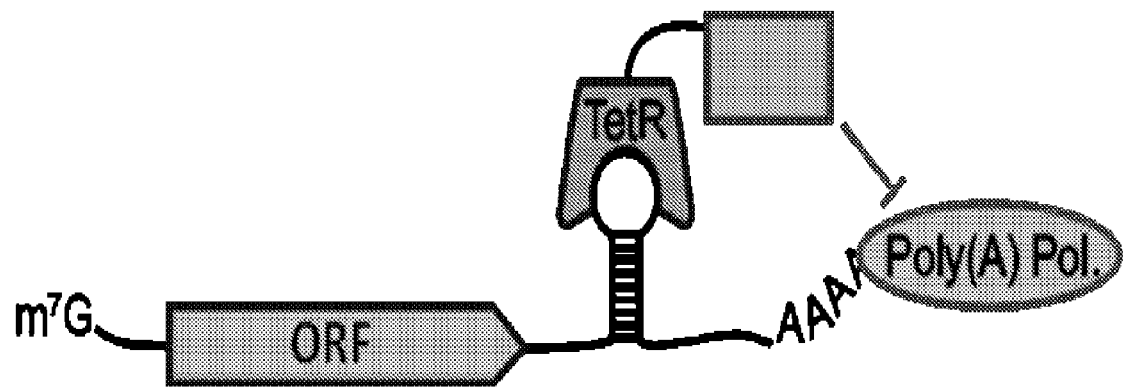

In one embodiment, the present invention contemplates a composition comprising a nucleic acid sequence attached to a ligand inducible regulatory protein, wherein the regulatory protein is fused to a localization domain and/or peptide (i.e., for example, forming a fusion protein). Although it is not necessary to understand the mechanism of an invention, it is believed that a nucleic acid sequence attached to the regulatory-localization fusion protein remains confined to a specific region within the cell (i.e., that region selected by the specific localization domain and/or peptide). In one embodiment, the nucleic acid sequence is further placed in operable combination with a ligand inducible regulatory protein binding aptamer within the 3'-UTR of the mRNA to mark a transcript of interest. See, FIG. 14A. Although it is not necessary to understand the mechanism of an invention, it is believed that in the absence of a ligand having high affinity for the regulatory protein, the nucleic acid will diffuse through the cell and bind the fusion protein either: i) once the fusion protein has already reached its final subcellular location, or ii) while the fusion protein is being actively transported to its destination within the cell. In either case, the eventual result is that the nucleic acid sequence is spatially trapped until the regulatory protein specific ligand is added, thereby releasing the nucleic acid sequence (i.e., for example, losing specific affinity due to ligand binding induced conformational changes).

Signal peptides are also known to target proteins throughout the cell and tethering these signal peptides to inducible regulatory proteins (i.e., for example TetR) may provide a controllable intracellular trafficking model. In one embodiment, the present invention contemplates a method for trafficking control to the plasma membrane using a fusion protein comprising a ligand inducible regulatory protein and a C-terminal polybasic, prenylation signal from Kras4B Heo et al., "PI(3,4,5)P3 and PI(4,5)P2 lipids target proteins with polybasic clusters to the plasma membrane" *Science* 314:1458-1461 (2006); and Levskaya et al., "Spatiotemporal control of cell signaling using a light-switchable protein interaction" *Nature* (2009). Other embodiments may include protein domains trafficking dendritic protein localization. Chiaruttini et al., "Dendritic trafficking of BDNF mRNA is mediated by translin and blocked by the G196A (Va166Met) mutation" *Procd Natl Acad Sci USA* 106:16481-16486 (2009); Huang et al., "Facilitation of dendritic mRNA transport by CPEB" *Genes Dev* 17:638-653 (2003); and Hirokawa, N., "mRNA Transport in Dendrites: RNA Granules, Motors, and Tracks" *J. Neurosci.* 26:7139-7142 (2006). In one embodiment, the present invention contemplates a fusion protein comprising a ligand inducible regulatory protein and a dendritic localization protein domain or peptide.

Although it is not necessary to understand the mechanism of an invention, it is believed that a ligand inducible regulatory protein and the mRNA encoding an aptamer having specific affinity for the regulatory protein spatially overlap in the desired region when no ligand is present, but that after ligand binding to the regulatory protein (i.e., induction), the regulatory protein-ligand complex remains localized whereas the mRNA encoding the aptamer diffuses throughout the intracellular space. Validation studies may be performed wherein the regulatory-localization fusion protein can be visualized by a further fusion with a GFP. It would be expected that the triple fusion regulatory-localization-GFP protein retains all functionality thereby enabling targeting and detection.

Alternatively, many other methods such as immunofluorescence or fluorescence in situ hybridization (FISH) may also be used to detect regulatory protein localization. Lécuyer, et al., "Fluorescent in situ hybridization protocols in Drosophila embryos and tissues" *Methods Mol. Biol* 420: 289-302 (2008); and Lecuyer et al., "Global Analysis of mRNA Localization Reveals a Prominent Role in Organizing Cellular Architecture and Function" *Cell* 131:174-187 (2007). Using fluorescently-labeled probes for RNA, FISH would be expected to show not only the precise location of the transcript, but also the degree of overlap with the regulatory protein anchor. To show the downstream effects of this mRNA positioning, a regulatory protein-binding aptamer can be tagged with a transcript encoding venus YFP.

3 RNA Splicing-Related Proteins

Nascent eukaryotic mRNA generated within the nucleus generally comprise a 3' poly(A) tail. mRNA polyadenylation is generally believed to improve stability, provide localization into the intracellular space, and/or promote protein translation. Dreyfus et al., "The Poly(A) Tail of mRNAs Bodyguard in Eukaryotes, Scavenger in Bacteria" *Cell* 111:611-613 (2002); Zhao et al., "Formation of mRNA 3' Ends in Eukaryotes: Mechanism, Regulation, and Interrelationships with Other Steps in mRNA Synthesis" *Microbiol. Mol. Biol. Rev.* 63:405-445 (1999). It has been reported that polyadenylation may be performed by Poly(A) Polymerase (PAP), wherein inhibition of this enzyme prevents proper RNA maturation and significantly decrease protein expression from a transcript. Ko et al., "Identification of new poly(A) polymerase-inhibitory proteins capable of regulating pre-mRNA polyadenylation" *J. Mol. Biol* 318:1189-1206 (2002). In one embodiment, the present invention contemplates a method for interfering with polyadenylation using a nucleic acid sequence comprising a high affinity binding site for a ligand inducible regulatory protein, wherein the regulatory protein is a fusion protein comprising a functional protein domain that specifically inhibits PAP.

Studies performed in the area of U1 small nuclear (sn)RNA interference (U1i) have established the feasibility of controlling the polyadenylation process. U1i can repress gene expression by targeting specific RNA splicing proteins to the 3'-UTR of a transcript using, for example, short RNA adapters or genetically encoded aptamers Goraczniak et al., "Gene silencing by synthetic U1 Adaptors" *Nat Biotech* 27:257-263 (2009); and Ko et al., "Identification of new poly(A) polymerase-inhibitory proteins capable of regulating pre-mRNA polyadenylation" *J. Mol. Biol* 318:1189-1206 (2002), respectively. Whereas the targeted proteins normally remove introns from nascent RNA, in this case, specific domains within the targeted complex interact with, and inhibit, PAP. PAP inhibition prevents polyadenylation, and therefore protein expression from the specific transcript is repressed.

In one embodiment, the present invention contemplates a composition comprising a nucleic acid sequence encoding a 3' UTR high affinity binding site for a ligand inducible regulatory protein, wherein the regulatory protein is a fusion protein comprising a PAP-inhibiting protein domain to TetR. See, FIG. 14B. Although it is not necessary to understand the mechanism of an invention, it is believed that when bound to the mRNA, the splicing protein domain inhibits PAP and prevents polyadenylation, thereby reducing expression from the transcript. This can be viewed as a gene expression regulation method, orthogonal to the translation repression scheme described herein.

Various reports have suggested that multiple splicing proteins and domains can be tethered to the 3'-UTR of transcripts and exhibit PAP inhibition. Ko et al., "Identification of new poly(A) polymerase-inhibitory proteins capable of regulating pre-mRNA polyadenylation" *J. Mol. Biol* 318:1189-1206 (2002); Abad et al., "Requirements for gene silencing mediated by U1 snRNA binding to a target sequence" *Nucl. Acids Res.* 36:2338-2352 (2008); and Klein et al., "Fourteen Residues of the U1 snRNP-Specific U1A Protein Are Required for Homodimerization, Cooperative RNA Binding, and Inhibition of Polyadenylation" *Mol. Cell. Biol.* 20:2209-2217 (2000). The proteins characterized in these reports, as is otherwise reported in the art, are limited to non-inducible proteins bound to the RNA.

In one embodiment, the present invention contemplates a method for inhibiting polyadenylation comprising a ligand inducible regulatory fusion protein bound to an mRNA of interest. In one embodiment, the method comprises an in vitro assay of nuclear extracts from a human cell line. Gunderson et al., "U1 snRNP inhibits pre-mRNA polyadenylation through a direct interaction between U1 70K and poly(A) polymerase" *Mol. Cell* 1:255-264 (1998). In one embodiment, an in vitro transcribed RNA containing a 3'-UTR aptamer is added to an extract comprising a ligand inducible regulatory-PAP inhibitor fusion protein. After incubation, the RNA may be analyzed on a denaturing PAGE gel, and a decrease in overall transcript length, indicative of shorter poly(A) tail, should be apparent by Northern blotting or radiolabelling. Thus, the polyadenylation inhibition would be expected to correlate with a cellular outcome of decreased gene expression and/or protein translation.

In one embodiment, the PAP inhibitor-ligand inducible regulatory protein fusion protein may be combined with other RNA control mechanisms. For example, if an aptamer is placed within both the 5'- and 3'-UTRs of a transcript, the repressor-fusion protein could be located in each region. In the case with a polyadenylation inhibitor fused to TetR, the inherent TetR-aptamer interaction within the 5'-UTR should repress translation, while the TetR-fusion in the 3'-UTR will prevent polyadenylation and further reduce gene expression. Thus, for independent processes, one could assume that a multiplicative effect could occur yielding a very strong decrease in specific gene expression, and a single chemical cue could simultaneously reverse both effects.

III. MESSENGER RIBONUCLEIC ACID UNTRANSLATED REGION REGULATION

Figure 11:
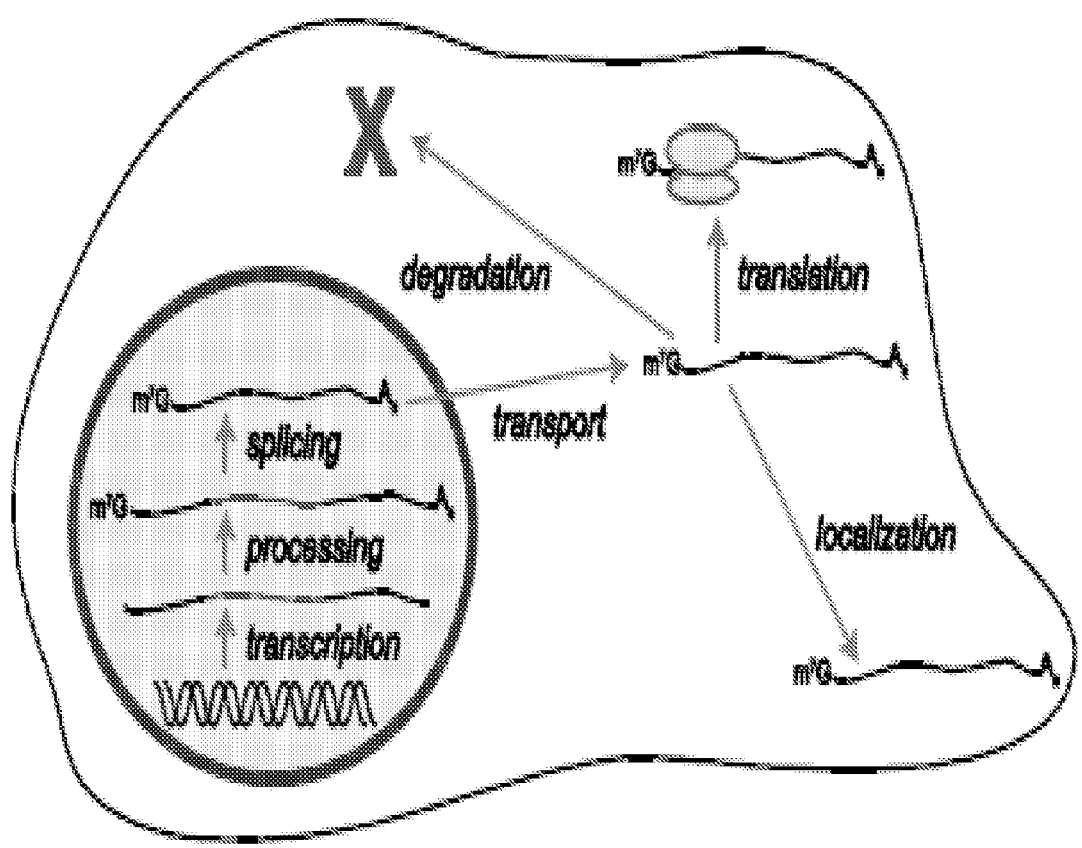
FIG. 11 presents a schematic representation of one embodiment of a generalized lifecycle for messenger ribonucleic acid (mRNA).

The protein-aptamer interacting pairs described herein are contemplated to facilitate inducible control of multiple RNA processes beyond protein translation. The lifetime of a transcript involves multiple steps from transcription to eventual degradation. See, FIG. 11. These processes provide the cell with an array of possible regulatory schemes, many of which have been described. Mazumder et al., "Translational control by the 3'-UTR: the ends specify the means" *Trends in Biochemical Sciences* 28:91-98 (2003); Cogoni et al., "Post-transcriptional gene silencing across kingdoms" *Current Opinion in Genetics & Development* 10:638-643 (2000); and Mansfield et al., "The ribonome: a dominant force in co-ordinating gene expression" *Biol. Cell* 101:169-181 (2009). These include, but are not limited to, RNA modifications within the nucleus, trafficking through the cell, protein translation, and altered transcript stability (infra). Native mechanisms within cells can exert control upon a single process, with specific phenotypic outcomes. This type of regulation can have profound effects such as: i) alteration of metabolism (Hentze et al., "Balancing Acts: Molecular Control of Mammalian Iron Metabolism" *Cell* 117: 285-297 (2004)); ii) defining organismal body development (Bashirullah et al., "RNA localization in development" *Annu. Rev. Biochem* 67:335-394 (1998); and iii) enabling viral invasiveness (Leonard et al., "Complex Formation between Potyvirus VPg and Translation Eukaryotic Initiation Factor 4E Correlates with Virus Infectivity" *J. Virol.* 74:7730-7737 (2000)).

Many of the molecular components underlying post-transcriptional regulation may include components including but not limited to, cis-acting ribozymes and trans-acting micro RNAs. For example, mRNA transcripts have been reported to interact with trans-acting RNA-binding proteins. Siomi et al., "RNA-binding proteins as regulators of gene expression" *Curr. Opin. Genet. Dev* 7:345-353 (1997). This association is enabled by unique oligonucleotide sequences/structures located within the mRNA. Maris et al., "The RNA recognition motif, a plastic RNA-binding platform to regulate post-transcriptional gene expression" *FEBS J* 272: 2118-2131 (2005). Once bound to an RNA, the protein factors either carry out a specific function or recruit other effectors.

A. Sequence-Specific RNA-Protein Interactions

It has been reported that translation in several cellular processes might be regulated by sequence-specific RNA-protein interactions in the 5' and/or 3' untranslated regions (UTRs) of eukaryotic mRNAs including, but not limited to: i) X chromosome dosage compensation (Grskovic et al., "A co-repressor assembly nucleated by Sex-lethal in the 3[prime]UTR mediates translational control of *Drosophila* msl-2 mRNA" *EMBO J* 22:5571-5581 (2003)); ii) embryogenesis (Nelson et al., "*Drosophila* Cup is an eIF4E-binding protein that functions in Smaug-mediated translational repression" *EMBO J* 23:150-159 (2004)); or iii) iron homeostasis Muckenthaler et al., "IRP-1 Binding to Ferritin mRNA Prevents the Recruitment of the Small Ribosomal Subunit by the Cap-Binding Complex eIF4F" *Molecular Cell* 2:383-388 (1998).

Figure 9:
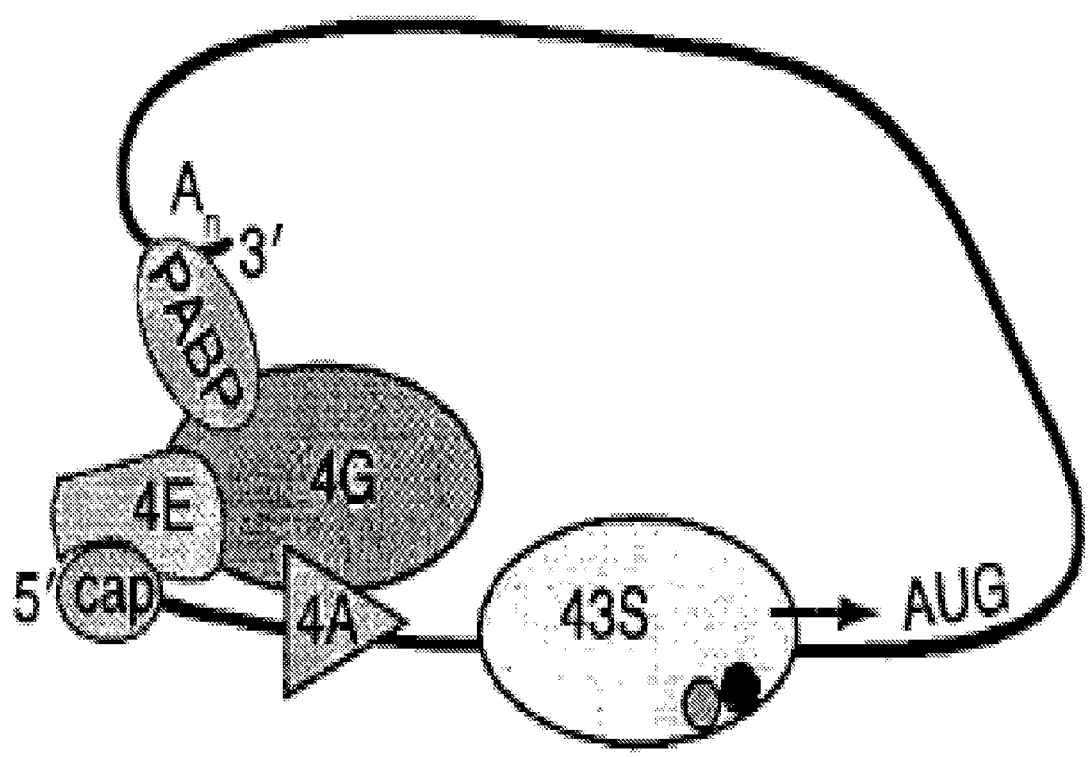
FIG. 9 presents a schematic representation of a canonical initiation of eukaryotic translation by cap-dependent ribosome assembly and scanning. For example, eukaryotic initiation factor 4E (eIF4E) binds the mRNA 5' 7-Me-Gppp cap and recruits the rest of the eIF4F complex (i.e., for example, the scaffold protein eIF4G and the RNA helicase eIF4A). eIF4G recruits polyadenylate-binding protein (PABP), resulting in circularization of the mRNA. The 43S pre-initiation complex, containing the 40S small ribosomal subunit, binds eIF4G and scans the mRNA in the 5'→3' direction until it detects the start codon AUG.

Another example is the iron-responsive element/iron-responsive protein (IRE/IRP) system wherein mRNA codes for the iron storage protein ferritin and contains a 35 nucleic acid stem-loop structure in its 5' UTR. This stem-loop structure, known as the IRE, binds the IRP with sub-nanomolar affinity under conditions of low labile iron concentration. Kim et al., "Translational Repressor Activity Is Equivalent and Is Quantitatively Predicted by in Vitro RNA Binding for Two Iron-responsive Element binding Proteins, TRP1 and IRP2" *J Biol Chem* 270:4983-4986 (1995). The IRE-IRP complex is believed to repress ferritin translation several-fold by inhibiting the assembly of the 43S pre-ribosomal complex. It is further believed that this assembly inhibition might be mediated through steric hindrance of the required interaction between eukaryotic translation initiation factor complex 4F (eIF4F) and the 40S small ribosomal subunit. Preiss et al., "Starting the protein synthesis machine: eukaryotic translation initiation" *Bioessays* 25:1201-1211 (2003), and FIG. 9. When intracellular free iron accumulates, the IRP switches to a low-IRE-affinity state and dissociates from the ferritin mRNA, permitting synthesis of ferritin.

It has been demonstrated that substituting other high affinity RNA-protein interactions at the 5' UTR of a given transcript can yield a similar inhibition of translation. Nie et al., "Different modes and potencies of translational repression by sequence specific RNA-protein interaction at the 5'-UTR" *Nucl. Acids Res.* 34:5528-5540 (2006). Post-transcriptional regulation mediated by sequence-specific RNA-protein interactions can occur via multiple modes, sometimes mediated by a single protein; for example, while the IRP produces a steric blockage of translation initiation by binding to an IRE in the 5' UTR of ferritin mRNA, it also serves to stabilize the transferrin receptor mRNA by binding to multiple IREs in the 3' UTR and blocking endonucleolytic degradation of the transcript. Kato et al., "Iron/MP-1-dependent regulation of mRNA expression for transferrin receptor, DMT1 and ferritin during human erythroid differentiation" *Experimental Hematology* 35:879-887 (2007).

RNA-protein interactions in the 3' UTR can also regulate translation, often through the recruitment of factors that interfere with 5' cap/EIF4E recognition by EIF4G. Gebauer et al., "Molecular mechanisms of translational control" *Nat Rev Mol Cell Biol* 5:827-835 (2004). In fact, sequence-specific RNA binding proteins have been shown in many cases to serve as adaptor proteins that: i) target RNA localization. Mowry, K. L., "Complex formation between stage-specific oocyte factors and a Xenopus mRNA localization element" *Proc. Natl. Acad. Sci. U.S.A* 93:14608-14613 (1996); and Schuldt et al., "Miranda mediates asymmetric protein and RNA localization in the developing nervous system" *Genes & Development* 12:1847-1857 (1998); and enhance/repress translation of specific mRNAs. Grskovic et al., "A co-repressor assembly nucleated by Sex-lethal in the 3[prime]UTR mediates translational control of *Drosophila* msl-2 mRNA" *EMBO J* 22:5571-5581 (2003). Although it is not necessary to understand the mechanism of an invention, it is believed that these natural mechanisms of mRNA-specific post-transcriptional regulation can be engineered into recombinant or in vitro systems and applied to the regulation of target transcripts of choice.

B. Direct Aptamer-Ligand Binding Regulation

An aptamer can be any polynucleotide or polypeptide that has been selected from a large, random library for its ability to bind a desired target ligand, whether the ligand is soluble or attached to a solid surface. Proske et al., "Aptamers-basic research, drug development, and clinical applications" *Appl. Microbiol. Biotechnol* 69:367-374 (2005). In the case of RNA aptamers, SELEX is often used to specifically expand and purify tightly-binding RNA molecules from a large library ($>10^{10}$ sequences) through successive cycles of transcription, positive or negative selection for binding, elution, reverse transcription and amplification by PCR. Ellington et al., "In vitro selection of RNA molecules that bind specific ligands" *Nature* 346:818-822 (1990); and Tuerk et al., "Systematic evolution of ligands by exponential enrichment: RNA ligands to bacteriophage T4 DNA polymerase" *Science* 249:505-510 (1990). Aptamers can then be further optimized for affinity and specificity by directed evolution or rational design. Using such techniques, aptamers have been developed that are capable of binding multiple targets including, but not limited to: i) tetracycline (Suess et al., "Conditional gene expression by controlling translation with tetracycline-binding aptamers" *Nucl. Acids Res.* 31, 1853-1858 (2003); ii) theophylline (Suess et al., "A theophylline responsive riboswitch based on helix slipping controls gene expression in vivo" *Nucl. Acids Res.* 32:1610-1614 (2004); iii) proteins such as bacteriophage T4 DNA polymerase (Tuerk et al., "Systematic evolution of ligands by exponential enrichment: RNA ligands to bacteriophage T4 DNA polymerase" *Science* 249:505-510 (1990); and iv) the outer surface of pathogenic organisms. Fang et al., "Aptamers Generated from Cell-SELEX for Molecular Medicine: A Chemical Biology Approach" *Acc. Chem. Res* (2009).doi:10.1021/ar900101s In one embodiment, the present invention contemplates a method such that once an RNA aptamer comprising a high affinity binding site for a ligand inducible regulatory protein has been identified, tested and verified, standard genetic engineering techniques allow for the insertion of the aptamer nucleic acid sequence into a larger RNA sequence (i.e., for example, into a 5' or 3' UTR of an mRNA), where it may retain its regulatory protein-binding activity.

Aptamer-bearing mRNAs have been used to effect several types of post-transcriptional gene regulation in response to direct ligand binding. Hanson et al., "Tetracycline-aptamer mediated translational regulation in yeast" *Mol. Microbiol* 49:1627-1637 (2003); Hwang et al., "Inhibition of gene expression in human cells through small molecule-RNA interactions" *Proc. Natl. Acad. Sci. U.S.A* 96:12997-13002 (1999); Kotter et al., "A fast and efficient translational control system for conditional expression of yeast genes" *Nucl. Acids Res.* 37:e120 (2009); Win et al., "A modular and extensible RNA-based gene-regulatory platform for engineering cellular function" Procd Natl Acad Sci 104:14283-14288 (2007); Win et al., "Higher-Order Cellular Information Processing with Synthetic RNA Devices" *Science* 322:456-460 (2008); and Weigand et al., "Tetracycline aptamer-controlled regulation of pre-mRNA splicing in yeast" *Nucl. Acids Res.* 35:4179-4185 (2007). One mechanism of such regulation involves the inhibition of translation by an aptamer in the 5' UTR. For example, inducible post-transcriptional regulation of *Saccharomyces cerevisiae* genes was achieved by placing one or more Tc-binding aptamers in the 5' UTR of target transcripts. Kotter et al., "A fast and efficient translational control system for conditional expression of yeast genes" *Nucl. Acids Res.* 37:e120 (2009). It was suggested that direct aptamer ligand binding in the yeast system inhibited translation by stabilizing the stem-loop structure of the aptamer, thereby blocking procession of the 43S scanning complex. This technique, however, did not work in mammalian cells. Although it is not necessary to understand the mechanism of an invention, it is believed that one explanation might be that a mammalian cell possesses a stronger 43S scanning activity capable of efficiently translating mRNAs containing 5' UTR structures that block translation in *S. cerevisiae*. McCarthy, J. E., "Posttranscriptional Control of Gene Expression in Yeast" *Microbiol. Mol. Biol. Rev.* 62:1492-1553 (1998).

C. Indirect Aptamer-Protein-Ligand Binding Regulation

Although many aptamers that directly bind to small molecules have been developed, the demonstrated applicability of these aptamers to post-transcriptional gene regulation is limited. Weigand et al., "Aptamers and riboswitches: perspectives in biotechnology" *Appl. Microbiol. Biotechnol* 85:229-236 (2009). Consequently, the reported aptamers directly binding non-metabolite ligands that can successfully be used to regulate RNA interference, mRNA stability, splicing or translation is therefore somewhat small, consisting of aptamers for theophylline, tetracycline, and biotin. Furthermore, it is only possible to couple aptamer-small molecule direct binding sequences to a downstream function if one can engineer an RNA-based mechanism such as the activation of an autonucleolytic ribozyme. Win et al., "A modular and extensible RNA-based gene-regulatory platform for engineering cellular function" *Procd Natl Acad Sci USA* 104:14283-14288 (2007); and Yen et al., "Exogenous control of mammalian gene expression through modulation of RNA self-cleavage" *Nature* 431:471-476 (2004).

In one embodiment, the present invention contemplates improving the extendibility and modularity of aptamer-based gene regulation by using regulatory proteins that bind small molecule ligands (i.e., for example, a Protein Binding Regulatory Aptamer (PBRA) system). One advantage of a PBRA system is that it allows access to diverse functionalities via protein domains that can be covalently attached or otherwise recruited to an aptamer-binding protein. Until the present invention, aptamer-ligand regulation of gene expression is limited to a direct binding of the ligand to the aptamer. In one embodiment, the present invention contemplates a composition comprising an aptamer, a regulatory protein, and a ligand, wherein the ligand binds to the protein and not the aptamer.

Figure 10:
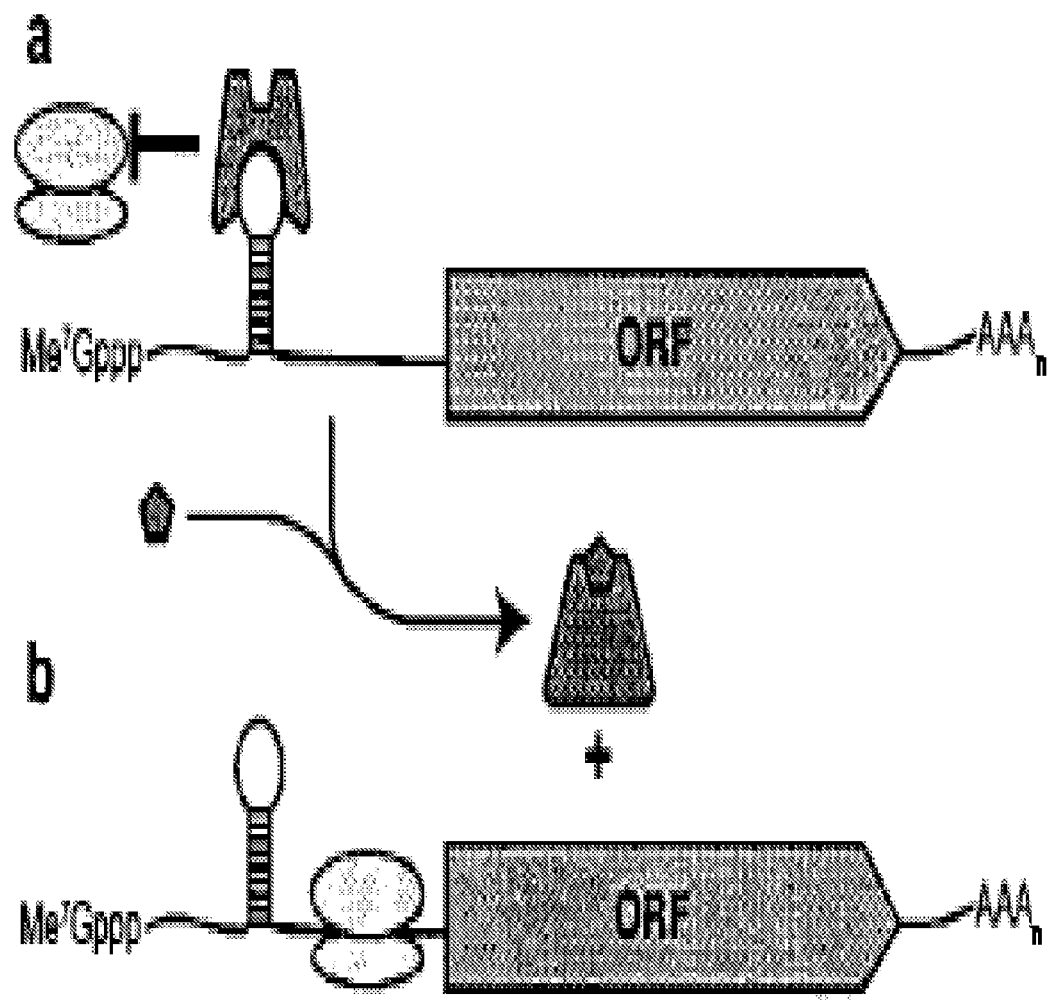
FIG. 10 presents a schematic representation of mechanistic model of embodiments of inducible protein binding RNA aptamer-based translational regulation.

The IRE-IRP system, though a small-molecule-responsive system in nature, is non-ideal for use as a tool for inducible expression due to the ubiquity of its iron ligand. In one embodiment, the present invention is reduced to practice using a bacterial repressor protein (i.e., for example, a tetracycline repressor protein) which is a ligand-inducible, sequence-specific DNA binding protein. Although it is not necessary to understand the mechanism of an invention, it is believed that this approach can develop a PBRA-protein pair possessing specific, ligand-inducible interaction suitable for post-transcriptional eukaryotic gene regulation. See, FIG. 10. A series of RNA aptamers that bind the Tc repressor (TetR) have been identified. High-affinity (i.e., for example, $K_d<1$ nM) binding of the tetracycline repressor protein to the aptamer stem loop binding site was efficiently reversed by the addition of anhydrotetracycline (aTc). See, FIG. 1. Minimization of stem loop stability is believed to be one approach to achieve aptamer optimization. For example, it has been reported that 5'-proximal RNA structures might repress translation of a downstream ORF. Babendure et al., "Control of mammalian translation by mRNA structure near caps" *RNA* 12:851-861 (2006). Although it is not necessary to understand the mechanism of an invention, it is believed that some TetR-binding aptamers might repress basal translation in the absence of TetR when inserted into a 5' UTR due to their high stability (i.e., for example, predicted stem formation $\Delta G$ of approximately −25 kcal/mol). Although it is not necessary to understand the mechanism of an invention, it is believed that this stability is an undesirable property for the optimal use of PBRAs for gene regulation. In an ideal case, one should be able to place an endogenous gene under PBRA control without greatly altering basal expression. In the case of the naturally occurring IRE-IRP system, although it exhibits a sub-nanomolar RNA-protein interaction and subsequent translational repression, the predicted stem formation $\Delta G$ is approximately −9 kcal/mol.

Figure 15A:
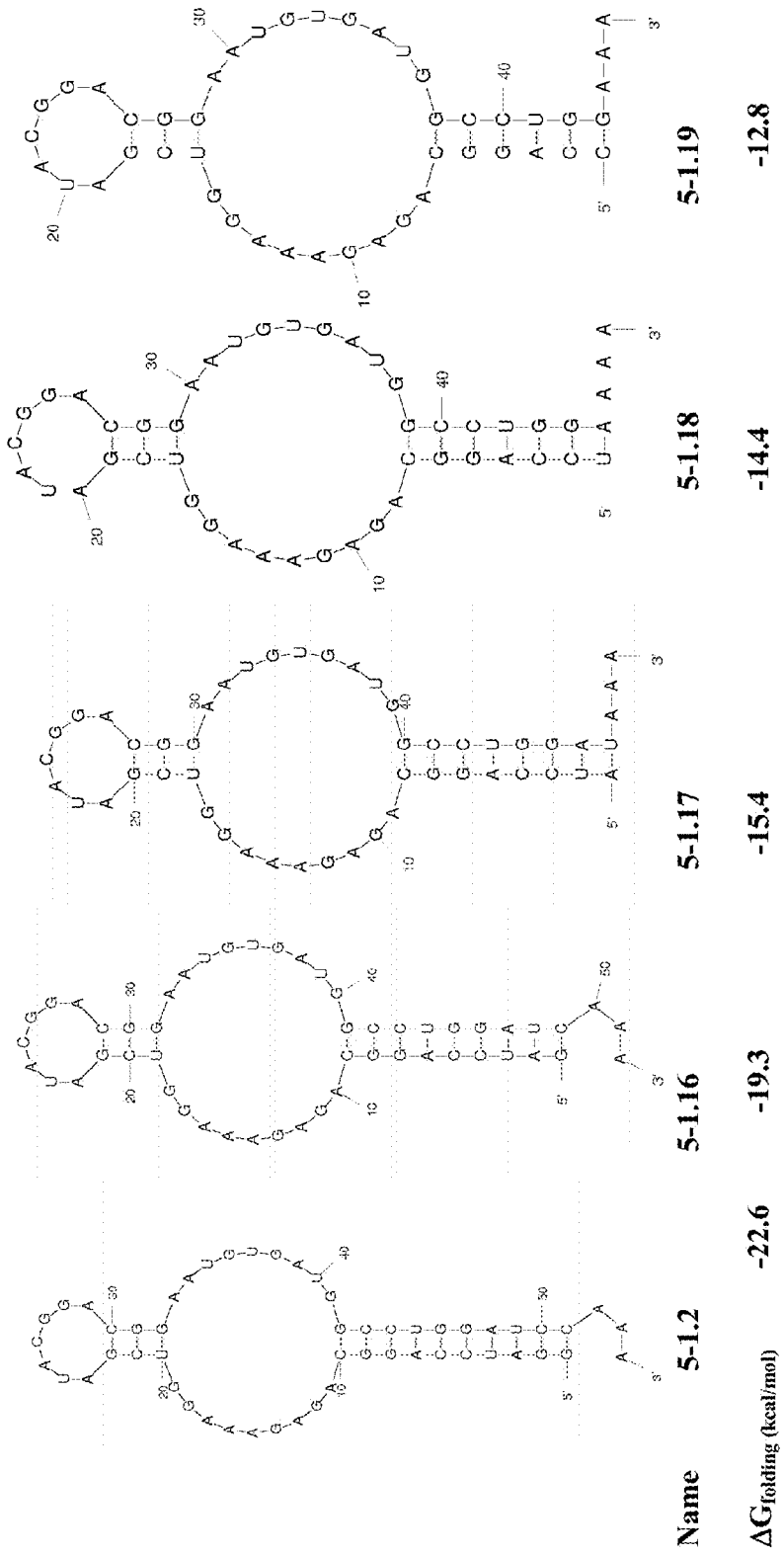
FIG. 15A presents several embodiments of aptamers [SEQ ID NO: 32-36] with decreased base-pairing stability.
Figure 15B:
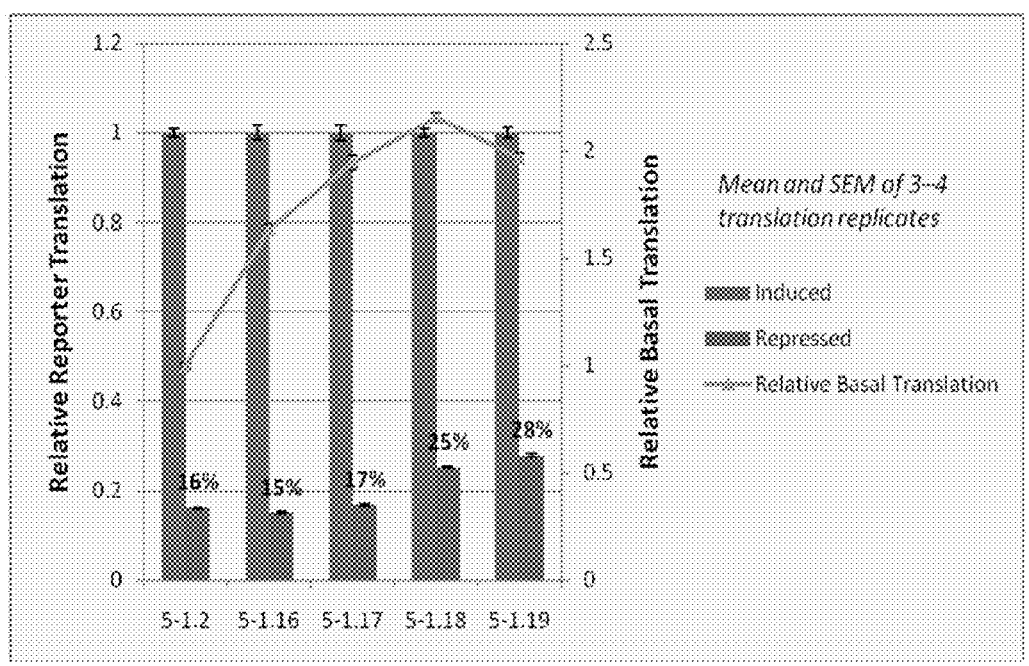
FIG. 15B presents exemplary data of the effect of aptamer modification such that inhibition of basal translation is reduced while regulation of translation by anhydrotetracycline-regulated TetR binding is preserved.

In one embodiment, the present invention contemplates an aptamer comprising a stem loop having a combination of stem truncation and nucleic acid substitutions (i.e., for example, G-C to A-U or G-U base pairs) to reduce stem strength while maintaining TetR binding and repression activity. See, FIG. 15. Such improvements in mRNA-aptamer constructs facilitate the portability of the presently disclosed system to multiple organisms, as it is known that tolerance to secondary structure in the 5' UTR varies greatly across species. McCarthy, J. E., "Posttranscriptional Control of Gene Expression in Yeast" *Microbiol. Mol. Biol. Rev.* 62:1492-1553 (1998).

IV. Ligand-Inducible Protein-Aptamer Regulation of mRNA Expression

Conventional inducible gene expression systems almost exclusively focus on the regulation of DNA transcription by manipulating interactions between RNA polymerases and their DNA template. Other known systems control target mRNA or protein stability through the use of small molecule-responsive autoendonucleases or degradation enhancer domains, respectively. These systems are highly specific in the factors to which they respond, and cannot be infinitely expanded into multiple, orthogonal inducible systems. One inducible mRNA translation system is currently available that involves ligand-binding aptamers (riboswitches) that are capable of affecting local mRNA structure in response to a ligand (supra).

In one embodiment, the present invention contemplates an aptamer in operable combination with (i.e., for example, ligated to) the untranslated region of an RNA sequence of interest, wherein the aptamer comprises a high affinity ligand-inducible regulatory protein binding site. In one embodiment, the RNA sequence of interest comprises a coding RNA (i.e., for example, messenger RNA, mRNA). In other embodiments, the RNA sequence of interest comprises a noncoding RNA (e.g. a regulatory RNA or an RNA that binds a specific target inside or outside a cell). By fusing one or more aptamers to such a noncoding RNA, the localization or activity of the noncoding RNA can be selectively manipulated according to the state of the aptamer, wherein the regulatory protein may either be bound or not bound to the aptamer.

In other embodiments, the regulatory protein comprises a repressor protein. In one embodiment, the repressor protein has specific affinity for an inducing ligand. In one embodiment, the inducing ligand comprises a small molecule, protein, nucleic acid, lipid, or saccharide. In one embodiment, the inducing ligand comprises a pharmaceutically acceptable composition and/or formulation such as a drug, pharmaceutical, or nutraceutical. In one embodiment, the inducing ligand is exogenous to a biological cell system or cell-free system. In one embodiment, the inducing ligand is endogenous to a biological cell system or cell-free system.

The present invention has many advantages over the systems described above. The presently disclosed system is extensible and modular, thereby allowing the combination of any given repressor protein-aptamer pair with a given gene of interest. This is in contrast to the 'riboswitch' technology wherein the ligand binds directly to a nucleic acid aptamer that is highly context-dependent and have only been developed for a limited set of ligands. The presently disclosed system is also functionalizable, since a given repressor protein can be fused with a second protein thereby conveying an additional activity, binding specificity, and/or subcellular localization property. The presently disclosed system is modular, whereby a given aptamer-repressor pair can be utilized in conjunction with any given coding sequence of interest by standard molecular cloning techniques. The presently disclosed system is also expandable; as it has been thoroughly demonstrated that RNA aptamers with high binding affinity and specificity for any given protein molecule can be readily generated using techniques such as SELEX. Further, there exist in nature a large number of potential repressor proteins that have been demonstrated to exhibit conformational changes in response to ligand binding (i.e., for example, but certainly not limited to, bacterial antibiotic response proteins and related DNA-binding proteins). While the presently disclosed system is described for modularity, and a demonstrated ability to regulate recombinant genes of interest using bio-orthogonal ligands, one having ordinary skill in the art would recognize that three-component systems may also be used in the scope of the present invention to regulate translation.

One area in which the presently disclosed system may be particularly advantageous is in the manipulation of evolutionarily divergent organisms whose biology is poorly characterized. The use of existing tools for gene regulation is frequently confounded by the lack of conserved elements such as transcription factors that are required for the proper functioning of such inducible expression systems. In some embodiments, the present invention addresses this problem by utilizing a set of interactions that are independent of divergent host factors, and likely interact primarily with the highly conserved mRNA translation system.

A. Validation of Ligand-Inducible Protein-Aptamer Gene Expression Complexes

In one embodiment, the present invention contemplates a method for regulating mRNA expression (i.e., for example, gene translation) using a ligand-inducible regulatory protein binding aptamer complex inserted into an in vivo prokaryotic gene expression system. For example, E. coli was transfected with a plasmid DNA encoding an RNA aptamer comprising a high affinity tetracycline repressor protein binding site fused to a chloramphenicol acetyltransferase (CAT) enzyme RNA coding sequence. CAT activity and bacterial growth in the transformed strain of E. coli was regulated by the addition of tetracycline to the growth media. The data presented herein demonstrate that the response of the in vivo expression system to tetracycline is independent of transcriptional regulation.

As illustrated herein, the SELEX method identified RNA aptamers that bind the bacterial tetracycline repressor protein (TetR) with low-to sub-nanomolar affinities. Although it is not necessary to understand the mechanism of an invention, it is believed that tetracycline analogs and/or derivatives may regulate this aptamer-TetR interaction in a manner analogous to tetracycline regulation of the naturally occurring tetO-TetR interaction (i.e., tetO is the cognate DNA operator sequence for native TetR). In one embodiment, the RNA aptamers identified using SELEX share two conserved sequence motifs (i.e., for example, Motif #1 and Motif #2) that reside within the single-stranded regions of stem-loop structures as predicted using in silico RNA folding methods. Aptamer truncation and mutational analysis support the functional importance of both motifs in TetR binding (infra). Inserting an aptamer comprising a high affinity TetR binding site into the 5'-UTR of a reporter mRNA confers ligand-inducible regulation of protein synthesis in an E. coli expression platform. The results described herein illustrate the potential for capitalizing on ligand inducible regulatory protein-RNA aptamer interactions to further enable broadly applicable RNA-based regulation.

In one embodiment, the bacterial regulatory system comprises: a) an RNA element "marking" a given transcript for regulation (i.e., for example, a luciferase open reading frame); b) a sensor protein that reversibly interacts with the RNA element above; and c) the presence or absence of an appropriate chemical stimulus (i.e., for example, an inducing ligand). The bacterial transcription factor TetR was selected as a compatible sensor protein for validation purposes. First, TetR has been extensively characterized and is easily expressed and purified using recombinant methods. Baumeister et al., "Contacts between Tet repressor and tet operator revealed by new recognition specificities of single amino acid replacement mutants" *J Mol Biol* 226: 1257-1270 (1992); and Ettner et al., "Fast large-scale purification of tetracycline repressor variants from overproducing *Escherichia coli* strains" *J Chromatogr A* 742: 95-105 (1996). Second, TetR can be expressed at suitable levels with retention of function in a broad variety of prokaryotic and eukaryotic contexts. Belli et al., "An activator/repressor dual system allows tight tetracycline regulated gene expression in budding yeast" *Nucleic Acids Res* 26:942-947 (1998); and Hillen et al., "Mechanisms underlying expression of Tn10 encoded tetracycline resistance" *Annu Rev Microbiol* 48:345-369 (1994); and Krueger et al., "Single-chain Tet transregulators" *Nucleic Acids Res* 31:3050-3056 (2003). Third, TetR binds with high affinity and specificity to several cell-permeable tetracyclines, ensuring that metabolically orthogonal control is retained. Fourth, TetR undergoes a conformational change in response to tetracycline binding, which causes a significant change in its affinity for its cognate DNA operator tetO. Orth et al., "Structural basis of gene regulation by the tetracycline inducible Tet repressor-operator system" *Nat Struct Biol* 7:215-219 (2000). Taken together, RNA aptamers could be expected to reversibly interact with a tetracycline repressor protein (TetR) in a tetracycline-dependent manner, wherein a recapitulation of a system analogous to the IRE/IRE-BP may regulate translational output. For example a sensor-protein/inducer IRE-BP/iron pair can be envisioned to be replaced by a TetR/tetracycline pair, and the IRE can be envisioned to be replaced by a TetR-binding aptamer complex.

The data described herein present an initial isolation and characterization of aptamers that bind TetR in a tetracycline-dependent manner. For example, upon inserting an aptamer comprising a TetR high affinity binding site into a 5'-UTR of a CAT reporter transcript in *E. coli,* both CAT activity and bacterial growth are induced in the presence of a tetracycline-based compound. The data suggest that regulation in this system occurs by a post-transcriptional mechanism predicated on a specific and inducible interaction between the aptamer element and the tetracycline repressor protein.

1. Using SELEX To Identify TetR Aptamers

RNA aptamers capable of interacting with TetR in a tetracycline-dependent manner were identified by selection from an initial library containing ~$10^{13}$ molecules using in vitro SELEX. Tuerk et al., "Systematic evolution of ligands by exponential enrichment: RNA ligands to bacteriophage T4 DNA polymerase" *Science* 249:505-510 (1990). Analysis determined that the smallest active aptamer folded into a stem-loop with an internal loop interrupting the stem. Mutational analysis then identified the aptamer's internal loop as a TetR binding site. RNA aptamers that bind TetR have recently been reported using a SELEX scheme distinct from that used here. Hunsicker et al, "An RNA aptamer that induces transcription" *Chem & Biol* 16:173-180 (2009). One of these aptamers was observed to induce TetR-regulated gene transcription in the absence of tetracycline via the tetO operator in *E. coli*. None of these aptamers were demonstrated to exhibit tetracycline-dependent binding to TetR.

The initial screening library comprised a plurality of RNA molecules with 50 randomized bases, flanked by constant regions. For SELEX, a C-terminal $His_6$-tagged TetR was immobilized on Ni-NTA magnetic beads. During the first four selection rounds imidazole was used to displace $His_6$-tagged TetR from the Ni-NTA beads, thereby indiscriminately eluting all TetR interacting aptamers.

To specifically enrich this eluted pool for aptamers binding TetR in a tetracycline-dependent manner, TetR bound RNA molecules were eluted with a low tetracycline concentration in the fifth round. The bulk Round 5 selected library was assessed for tetracycline-dependent binding to TetR. See, FIG. 1. The data demonstrate that the Round 5 selected library bound TetR in the absence of tetracycline. However, upon tetracycline addition, a significant fraction of the RNA library bound to TetR was released. Although it is not necessary to understand the mechanism of an invention, it is believed that these data are consistent with the selection scheme used, especially when a positive control using tetO DNA also demonstrated tetracycline-dependent binding. As sufficiently high affinity TetR binding aptamers were obtained in the Round 5 library with the desired tetracycline inducibility, individual aptamers from this pool were isolated and characterized.

2. Sequence and Predicted Structure of Aptamers

Figure 2:
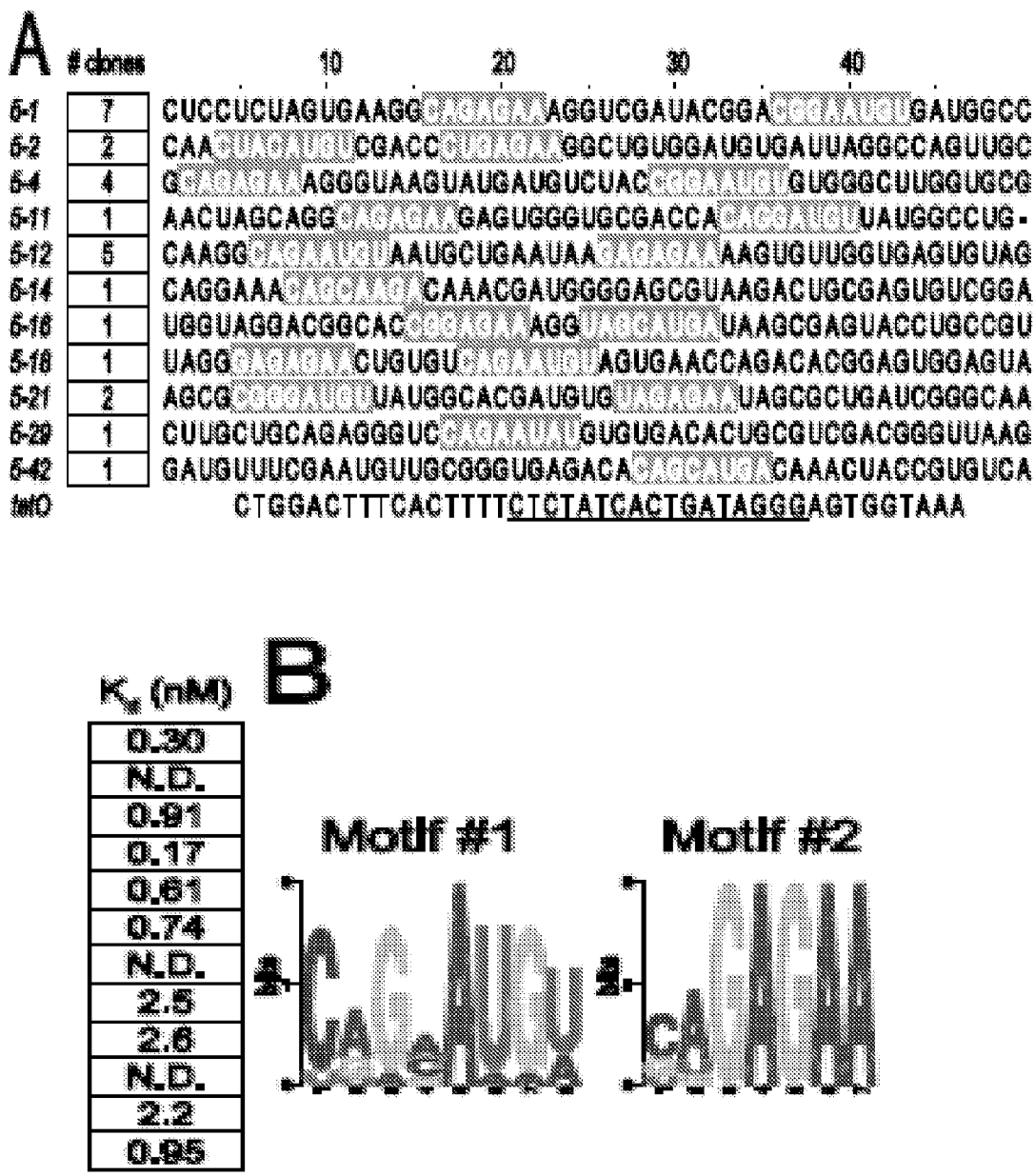
FIG. 2 presents several embodiments of RNA aptamers that share sequence and structural motifs and bind the tetracycline repressor protein with high affinity.
Figure 2:
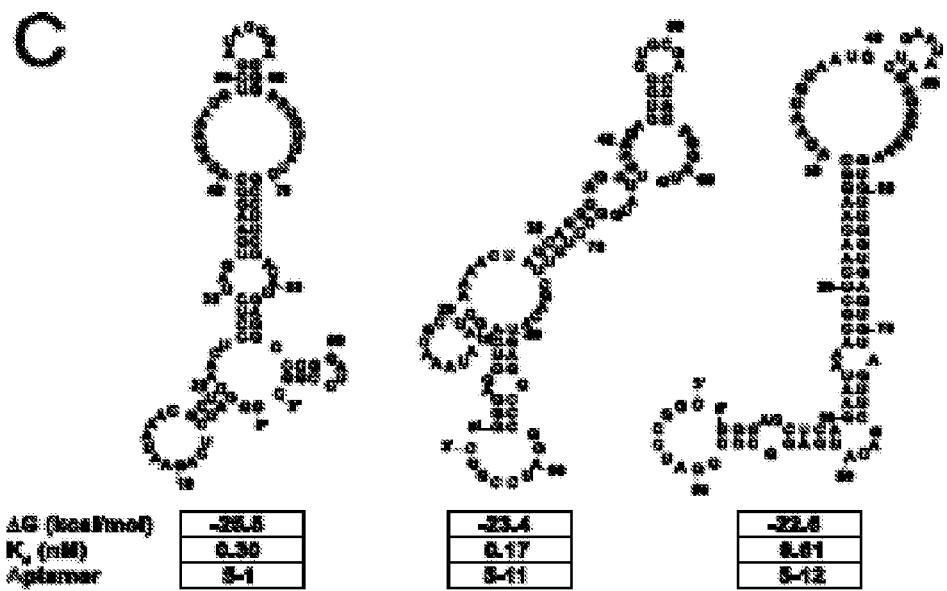
Figure 2:
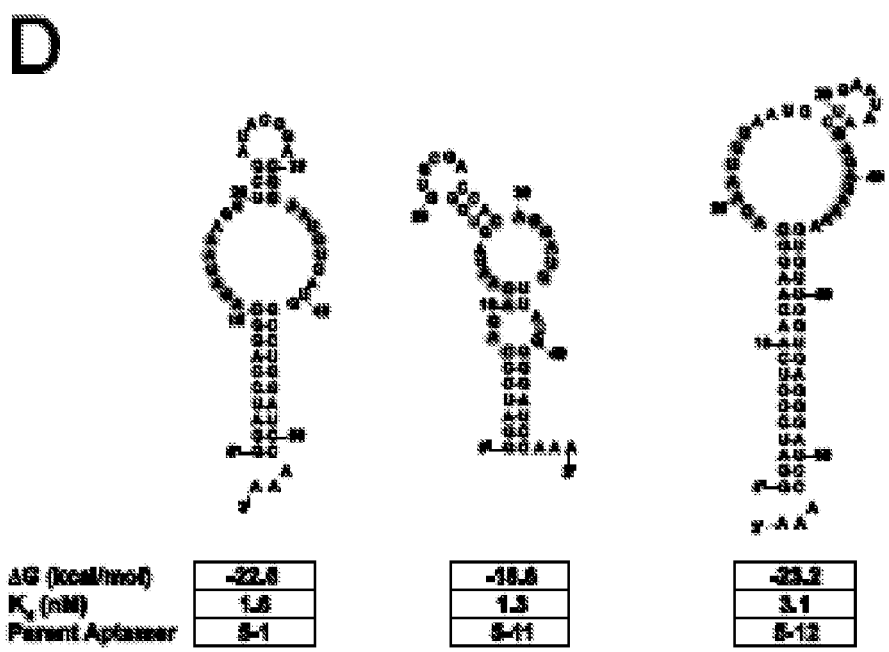

Twenty-six (26) of the isolated aptamer clones from the above screening protocol were selected for sequencing. See, FIG. 2A. Two highly conserved sequence motifs (i.e., for example, Motif #1 and Motif #2) were identified using the MEME algorithm. See, FIG. 2B; Bailey et al., "The value of prior knowledge in discovering motifs with MEME" *Proc Intl Conf Intell Syst Mol Biol* 3:21-29 (1995); and Bailey et al., "MEME: discovering and analyzing DNA and protein sequence motifs" *Nucleic Acids Res* 34: W369-373 (2006). The data show that Motif #1 is present in all of the sequenced aptamers, and is heterogeneous in its base composition. While Motif #2 is also prevalent, it appears to be enriched in purine content. Of note, neither Motif #1 nor Motif #2 share significant MEME-detected sequence homology with tetO, supporting the hypothesis that there may be a different interaction mode of TetR with tetO versus the RNA aptamers. The high frequency of both Motif #1 and Motif #2 in the selected RNA aptamers may signify a single major binding mode between these aptamers and the tetracycline repressor protein. However, the consensus regions do not share common position, order, or spacing within the aptamers, which might suggest a binding dependence that is less reliant on primary sequence than other factors, such as relative positioning of the motifs within the aptamers' secondary and tertiary structures.

To measure the affinity of the interaction between the aptamers and TetR, a cytometric bead-based binding assay was used. The data show that the measured $K_d$ values cluster in the low-to sub-nanomolar range. See, FIG. 2A. For comparison, under the present binding assay conditions, the $K_d$ for the interaction between tetO and TetR was ~0.95 nM. This compares favorably with a previously reported $K_d$ of ~0.17 nM obtained using an untagged TetR measured by surface plasmon resonance. Kamionka et al., "Two mutations in the tetracycline repressor change the inducer anhydrotetracycline to a corepressor" *Nucleic Acids Res* 32:842-847 (2004). Overall, the binding data disclosed herein suggest that the RNA aptamers bind TetR with affinities similar to, or exceeding, that of tetO.

The arrangement of these conserved sequence motifs within the folded aptamer and overall secondary structure of the full length aptamers were evaluated using Mfold. See, FIG. 2C: Mathews et al., "Expanded sequence dependence of thermodynamic parameters improves prediction of RNA secondary structure" *J Mol Biol* 288:911-940 (1999); and Zuker M., "Mfold web server for nucleic acid folding and hybridization prediction" *Nucleic Acids Res* 31:3406-3415 (2003). The data indicated that these aptamers are highly structured, and form stem-loops in the conserved structural elements. Furthermore, in nearly all cases, the conserved MEME motifs lie within the loop portion of these stem-loop elements. From this data, it may be hypothesized that these motifs may be the main determinants in aptamer binding to TetR as evaluated below.

3. Truncation and Mutational Analysis of Selected Aptamers

Three of the RNA aptamers (5-1, 5-11, and 5-12) identified above were selected for further analysis. The aptamers were minimized (i.e., for example, serially truncated) to probe both the dispensability of sequence flanking the conserved regions, and the significance of the predicted secondary structure and motif locations. For example, portions of the 5'-and 3'-termini of 5-1, 5-11, and 5-12 were successively deleted to obtain shortened stem-loop structures within which the motifs were positioned identically to the parent aptamer based on Mfold predictions. See, FIG. 2D. Additionally, a sequence comprising a portion of the stem region was changed while preserving overall stem structure. These minimized aptamers were still capable of binding to the tetracycline repressor protein with low nanomolar affinities, but exhibited a 5-10 fold increase in IQ when compared to the full-length parent aptamer. This slight decrease in affinity could arise due to less favorable folding thermodynamics of the truncated aptamers, as indicated by diminished calculated folding ΔG values for two of the three tested truncations. See, FIGS. 2C & 2D. Alternatively, it is possible that aptamer elements outside the conserved regions also interact with TetR to provide stabilizing interactions, and their removal negatively affects binding. These putative elements may not be sufficiently conserved to be detectable using sequence based methods, but rather would require high-resolution structural analysis of the TetR-aptamer complex.

Figure 3B:
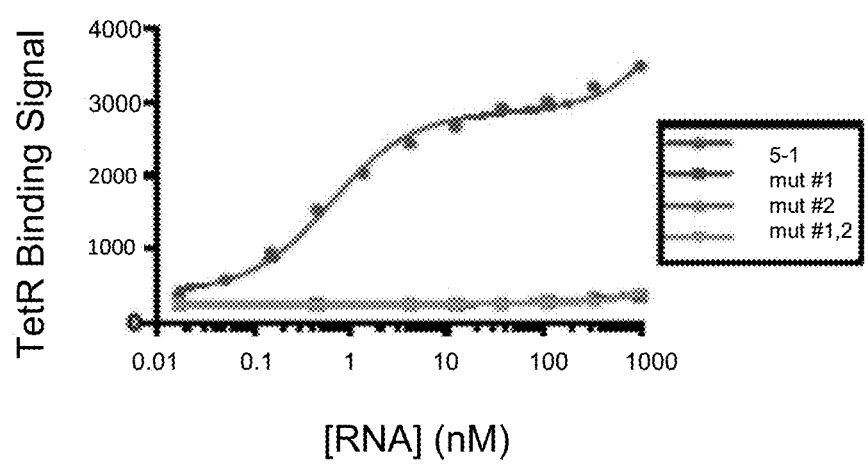
FIG. 3B: Tetracycline repressor protein binding curves with the 5-1 aptamer and variants.

To further assess the contribution of the two conserved motifs to the TetR-aptamer interaction, each motif was mutated both individually and simultaneously within the context of the 5-1 aptamer. See, FIG. 3A. For example, Motif #1 was scrambled, whereas Motif #2 was replaced with a randomly generated sequence of the same length due to its high purine content. Mutating one or both of these conserved motifs completely abolishes aptamer affinity to TetR, suggesting that these regions contribute significantly to the TetR-RNA aptamer interaction. See, FIG. 3B. This contrasts with the minimal impact that swapping the stem sequence within the truncation has on aptamer binding to TetR. Although it is not necessary to understand the mechanism of an invention, it is believed that these data suggest that conserved Motif #1 and Motif #2 in the minimal stem-loop structures physically interact with TetR, and are consistent with saturation mutagenesis studies and in-line probing experiments recently reported for other TetR-binding aptamers also displaying a stem-loop element implicated in binding. Hunsicker et al., "An RNA aptamer that induces transcription" *Chem Biol* 16:173-180 (2009).

4. TetR-Aptamer Mediated Post-Transcriptional Regulation in *E. Coli*

Figure 4:
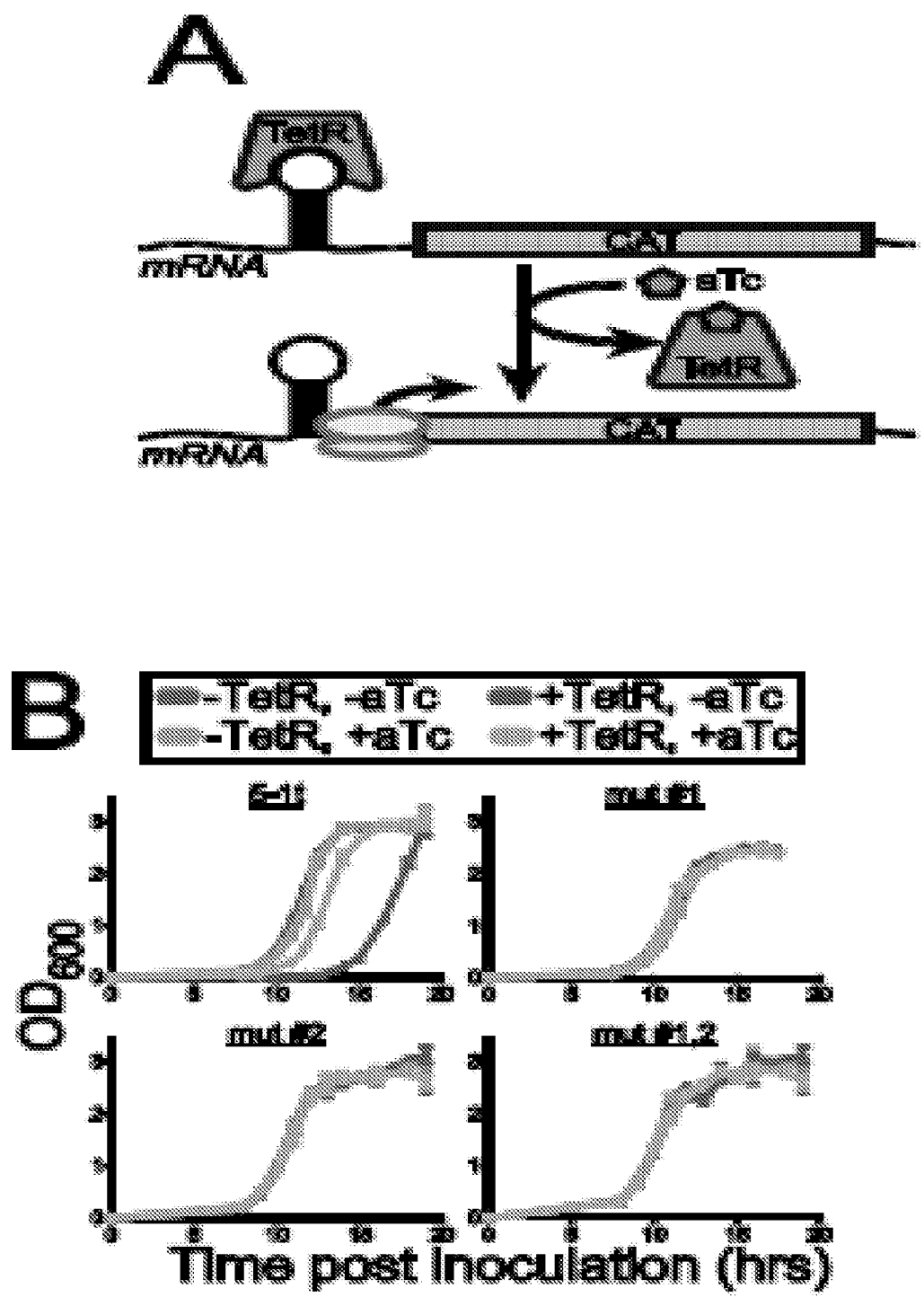
FIG. 4 presents exemplary data showing that a tetracycline repressor protein-aptamer interaction post-transcriptionally controls gene expression.
Figure 4:
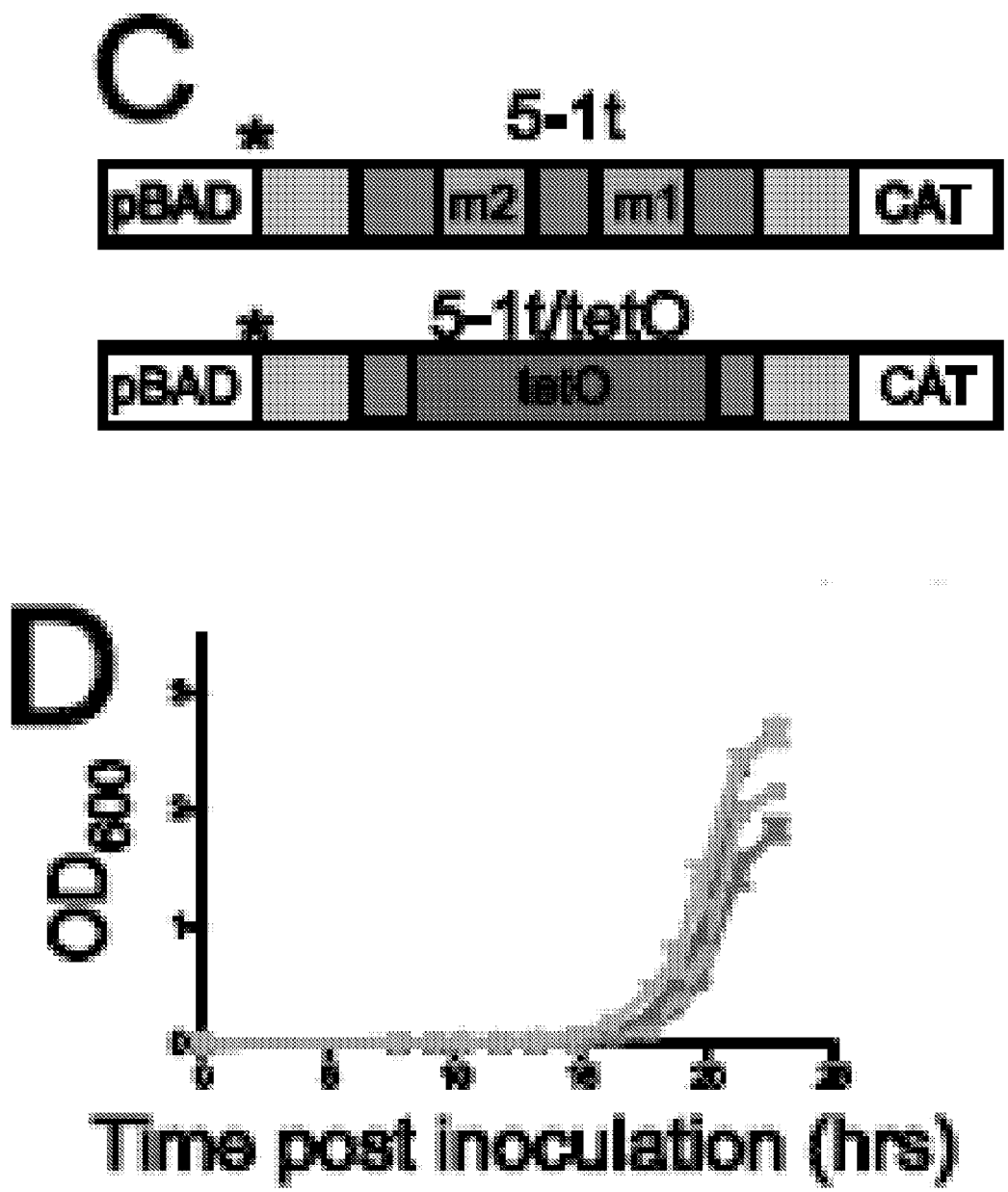

In one embodiment, the present invention contemplates a composition comprising an inducible TetR-binding aptamer capable of regulating in vivo protein synthesis in a bacterial expression platform. For example, *E. coli* HB101 was co-transformed with compatible plasmids from which TetR and a CAT reporter were produced upon isopropylthio-β-D-galactoside (IPTG) and arabinose induction, respectively. In one embodiment, the CAT reporter transcript encodes a TetR-binding aptamer sequence immediately upstream of the Shine-Dalgarno (SD) sequence within the 5'-UTR. See, FIG. 4A. This configuration was selected based on previous studies demonstrating that post-transcriptional regulation using theophylline-and TPP-binding aptamers is possible using this relative positioning of the aptamer and SD sequence. Suess et al, "A theophylline responsive riboswitch based on helix slipping controls gene expression in vivo" *Nucleic Acids Res* 32:1610-1614 (2004); and Winkler et al., "Thiamine derivatives bind messenger RNAs directly to regulate bacterial gene expression" *Nature* 419: 952-956 (2002). One model of a working system is shown wherein expressed TetR binds to an RNA aptamer region encoded within a reporter transcript and prevents efficient CAT synthesis. See, FIG. 4B. Although it is not necessary to understand the mechanism of an invention, it is believed that this reduction in CAT expression could occur because TetR binding to the aptamer element in close proximity to the SD may be interfering with ribosome access to the SD sequence due to steric hindrance and/or altering mRNA stability and turnover kinetics. Since a tetracycline-based compound is capable of disrupting the interaction of TetR with an RNA aptamer, adding a tetracycline-based compound would be expected to restore CAT synthesis and allow cells to grow in media containing chloramphenicol. CAT levels and bacterial growth were measured in the presence of chloramphenicol, both as a function of TetR expression and the presence or absence of a tetracycline-based compound (i.e., for example, anhydrotetracycline, aTc).

Initial screens identified a truncated version of the 5-1 aptamer (i.e., for example, 5-1t) as capable of repressing CAT expression in *E. coli*. During growth experiments in chloramphenicol-containing media, cells co-expressing TetR and a CAT reporter construct (i.e., for example, +TetR/–aTc) grow significantly more slowly, and exhibit a lag time ~5 hours longer than that for control cells (i.e., for example, –TetR/ ±aTc). See, FIG. 4B. When aTc was added to TetR-expressing cells (+TetR/+aTc) a significantly reduced lag time of ~1 hour relative to the controls was observed. Further, aTc has no effect on cell growth in the absence of TetR, indicating that there is no significant regulatory outcome mediated by a direct interaction of aTc with the TetR aptamer element. Also, no direct aTc-induced toxicity was observed at the concentration used.

Figure 5:
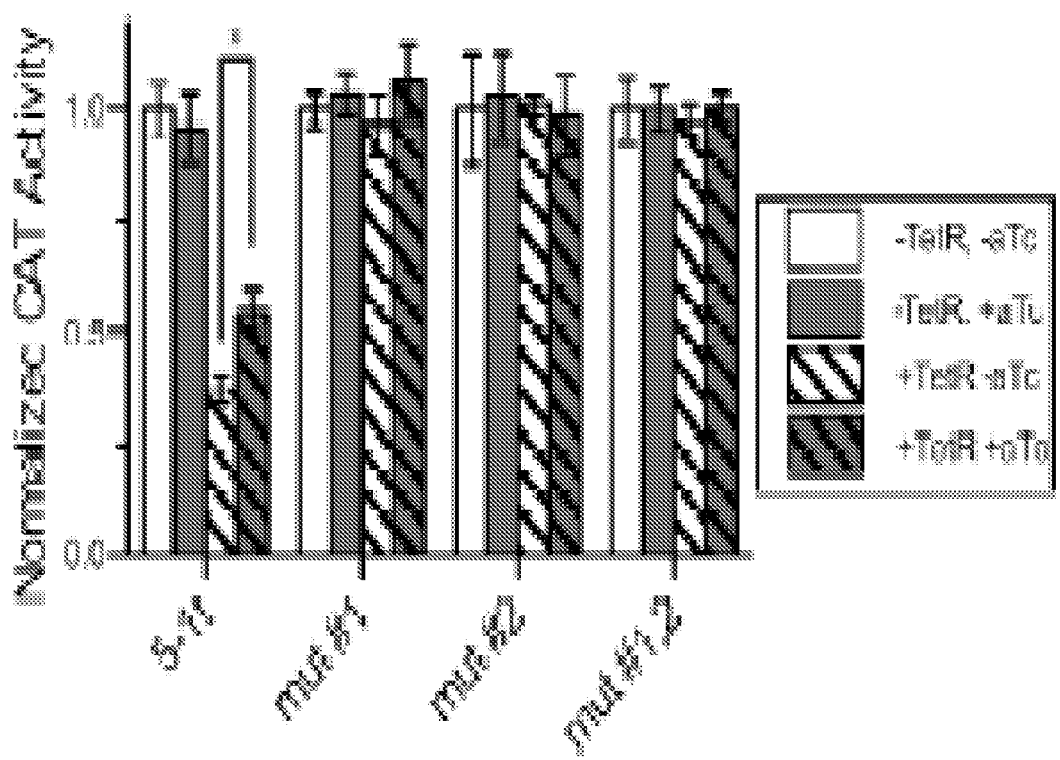
FIG. 5 presents exemplary data showing in vitro CAT activity in cell lysates from *E. coli*. Data is relative to the −TetR/−aTc condition for each construct tested. Error bars represent standard deviation of three independent experimental replicates. *p-value=0.006.

Mutating conserved Motif #1 or Motif #2, either individually or simultaneously, restored *E. coli* growth to wild-type levels, independent of TetR co-expression and presence/absence of aTc. CAT activity measurements in cell lysates follows the trend predicted from the growth assay results. Specifically, TetR expression in the absence of aTc decreases CAT activity levels to ~37% of that measured in the –TetR/ ±aTc control cells. See, FIG. 5. While aTc induction does not fully restore CAT activity to control levels, there is a reproducible and statistically significant (p=0.006) increase in CAT activity to ~55% that of the control cells. Similar to the results of the growth experiments, all three aptamer mutants exhibit similar relative CAT activity profiles independent of the presence or absence of TetR and/or aTc. Thus, the interaction between TetR and aptamer 5-1t appears to modulate CAT activity level in response to aTc, and the ~20% difference in CAT activity between the repressed and aTc-induced condition is sufficient to directly mediate a significant change in growth phenotype.

Furthermore, it was established that the measured changes in CAT activity and growth phenotype were not arising at the transcriptional level. TetR function as a transcriptional regulator has been reported, making it possible that tetracycline might simply be interacting with the DNA encoding an aptamer to mediate the observed changes at the transcriptional level. To exclude this possibility, it was determined that TetR does not specifically interact with the DNA encoding an aptamer sequence. Additionally, a hybrid 5-1t/tetO reporter construct was created by replacing the RNA aptamer's conserved Motif #1 and Motif #2 and intervening sequence with the tetO DNA sequence. See, FIG. 4C. The tetO DNA sequence, unlike DNA encoding the aptamer, is known to bind TetR with high affinity. Co-expressing this hybrid construct with another plasmid encoding TetR revealed no changes in growth phenotype. See, FIG. 4D. These results support a model whereby TetR interacts specifically with the 5-1t RNA aptamer encoded within CAT reporter mRNA in such a manner that translation is regulated.

Consequently, transcriptional regulation can be excluded as an operative mechanism for explaining the data presented herein. Although it is not necessary to understand the mechanism of an invention, it is believed that a role for transcriptional regulation may effectively be ruled out as even a high affinity tetracycline repressor protein-interacting tetO DNA operator placed within the same region as a RNA aptamer coding sequence does not modulate a TetR and/or aTc-dependent growth phenotype. These data, together with the fact that TetR does not bind 5-1t DNA with high affinity but binds 5-1t RNA with high affinity ($K_d$=18 nM), strongly favors a post-transcriptional regulation mechanism.

Figure 6:
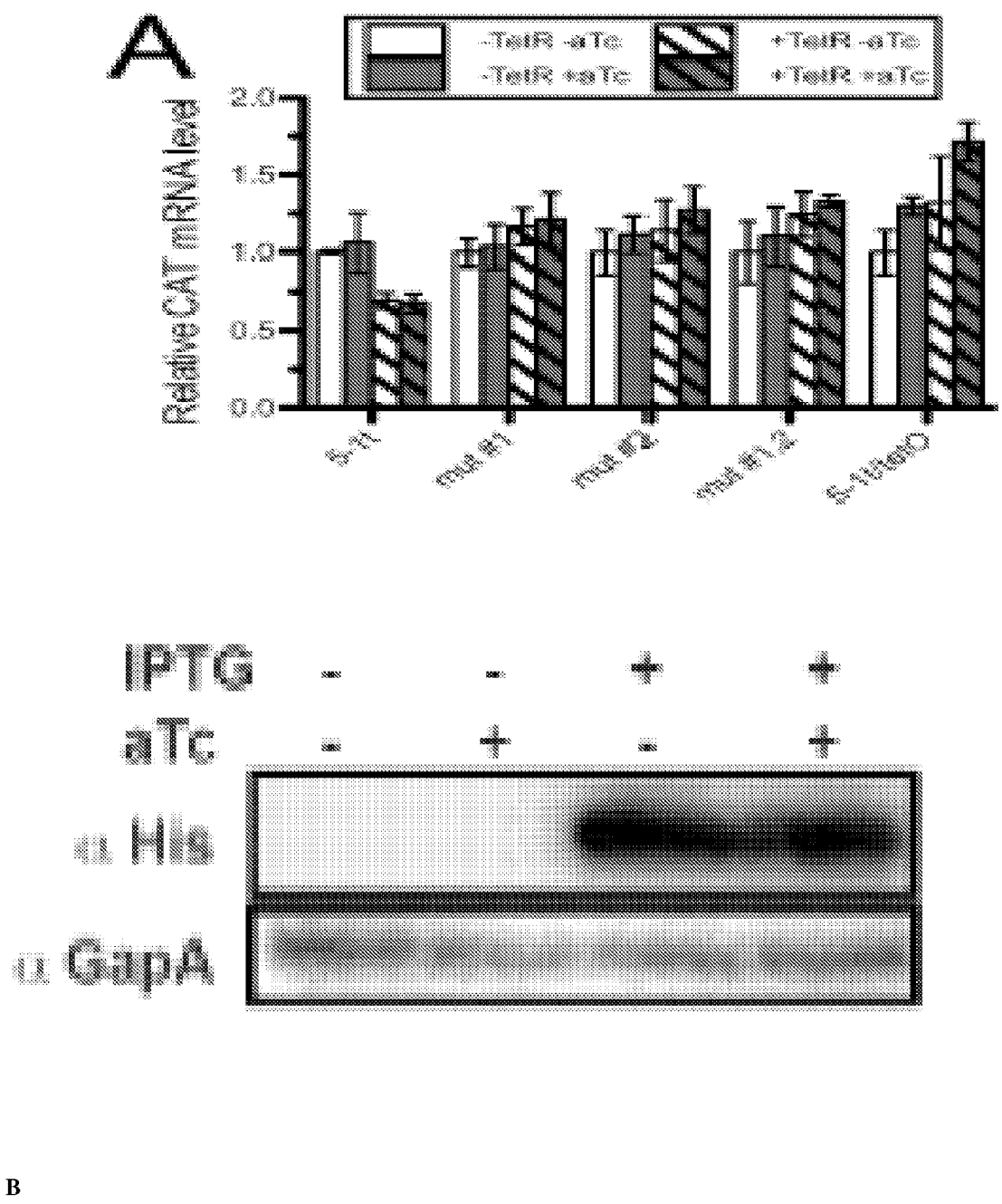
FIG. 6A presents exemplary quantitative PCR data showing relative CAT mRNA levels under indicated growth conditions. Data is relative to the −TetR/−aTc condition for each construct tested. Error bars represent standard deviation of three independent experimental replicates.
FIG. 6B presents exemplary Western blot data showing tetracycline repressor protein (α-His) levels and a loading control (α-GapA) levels under assay conditions.

To obtain insight into this post-transcriptional regulation mechanism, quantitative RT-PCR was used to measure expressed CAT transcript levels relative to a housekeeping gene (i.e., for example, gapA). Measurements were made using *E. coli* grown with and without TetR expression and in the presence or absence of aTc. See, FIG. 6A. In cells harboring a 5-1t construct, adding aTc does not lead to a significant difference in CAT transcript levels, regardless of TetR expression status. However, TetR expression results in a significant reduction in CAT transcript levels relative to cells that do not express TetR. Conversely, using a 5-1t motif mutant reporter construct, CAT transcript levels appear unchanged, or even increased in the presence of TetR and aTc. See, FIG. 6A. Additionally, cells expressing a hybrid 5-1t/tetO CAT construct have a relative CAT transcript level profile similar to those seen with Motif #1 and Motif #2 mutants. This latter observation further confirms that transcriptional regulation is not the predominant mechanism mediating phenotypic changes. Lastly, Western blotting analysis was used to exclude significant differences in TetR expression levels as a contributing factor to the observed growth phenotypes, CAT activity, and transcript level measurements. See, FIG. 6B. Overall, these data indicate that only when an intact 5-1t aptamer that is competent for interacting with TetR is present in a CAT reporter construct do CAT mRNA levels decrease when TetR is co-expressed. These data show that an aTc-inducible interaction between TetR and a TetR-binding aptamer inserted into the 5' UTR of a bacterial mRNA is useful to regulate gene expression post-transcriptionally in *Escherichia coli*. Although it is not necessary to understand the mechanism of an invention, it is believed that the demonstrated success in the bacterial model predicts similar success in eukaryotic models as well.

B. Regulation of Protein Translation in a Mammalian Cell-Free System

It has been reported that soluble extracts capable of performing translation in vitro have been prepared from sources including, but not limited to: i) human cell lines (Mikami et al., "An efficient mammalian cell-free translation system supplemented with translation factors" *Protein Expression and Purification* 46:348-357 (2006); ii) wheat germ (Tsuboi et al., "Wheat Germ Cell-Free System-Based Production of Malaria Proteins for Discovery of Novel Vaccine Candidates" *Infect. Immun.* 76:1702-1708 (2008); iii) budding yeast (Hussain et al., "Translation of homologous and heterologous messenger RNAs in a yeast cell-free system" *Gene* 46:13-23 (1986).; and iv) protozoa (Duszenko et al., In vitro translation in a cell-free system from *Trypanosoma brucei* yields glycosylated and glycosylphosphatidylinositol-anchored proteins" *Eur. J. Biochem* 266:789-797 (1999); Mureev et al., "Species-independent translational leaders facilitate cell-free expression" *Nat Biotech* 27:747-752 (2009); and Surolia et al., "Chloroquine inhibits heme-dependent protein synthesis in *Plasmodium falciparum*" pnas.org/content/88/11/4786). These cell-free translation systems vary greatly in their activity and requirements for particular features in the mRNA to be translated (such as a 5' cap or suitable UTR sequences). Mikami et al., "An efficient mammalian cell-free translation system supplemented with translation factors" *Protein Expression and Purification* 46:348-357 (2006). For example, the rabbit reticulocyte lysate (RRL) system is frequently used for in vitro studies because it is highly permissive, translating with high efficiency even minimal mRNAs consisting of only an uncapped coding sequence. However, RRL can be made fairly cap-dependent by using small amounts of mRNA and through the addition of sequence-nonspecific RNA-binding proteins that are thought to block EIF4E independent ribosome assembly at unstructured regions within the 5' UTR. Svitkin et al., "General RNA binding proteins render translation cap dependent" *EMBO J* 15:7147-7155 (1996); and Bablanian et al., "Mechanism of selective translation of vaccinia virus mRNAs: differential role of poly(A) and initiation factors in the translation of viral and cellular mRNAs" *J Virol* 65:4449-4460 (1991). Using an in vitro system to study translation may be particularly useful because known quantities of exogenous mRNAs or proteins can be added. Even endogenous proteins of interest can be controlled by immunodepletion and replacement with a known quantity. Evdokimova et al., "The Major Core Protein of Messenger Ribonucleoprotein Particles (p50) Promotes Initiation of Protein Biosynthesis in Vitro" *J Biol Chem* 273: 3574-3581 (1998). It is well established that RRL can be used to reproduce in vitro and characterize translational regulation mediated by sequence specific RNA-protein interactions in the UTRs of natural or reporter mRNAs. Samaniego et al., "Molecular characterization of a second iron-responsive element binding protein, iron regulatory protein 2. Structure, function, and post-translational regulation" *J Biol Chem* 269: 30904-30910 (1994); and Mazumder et al., "Translational Silencing of Ceruloplasmin Requires the Essential Elements of mRNA Circularization:Poly(A) Tail, Poly(A)-Binding Protein, and Eukaryotic Translation Initiation Factor 4G" *Mol. Cell. Biol.* 21:6440-6449 (2001).

Figure 7:
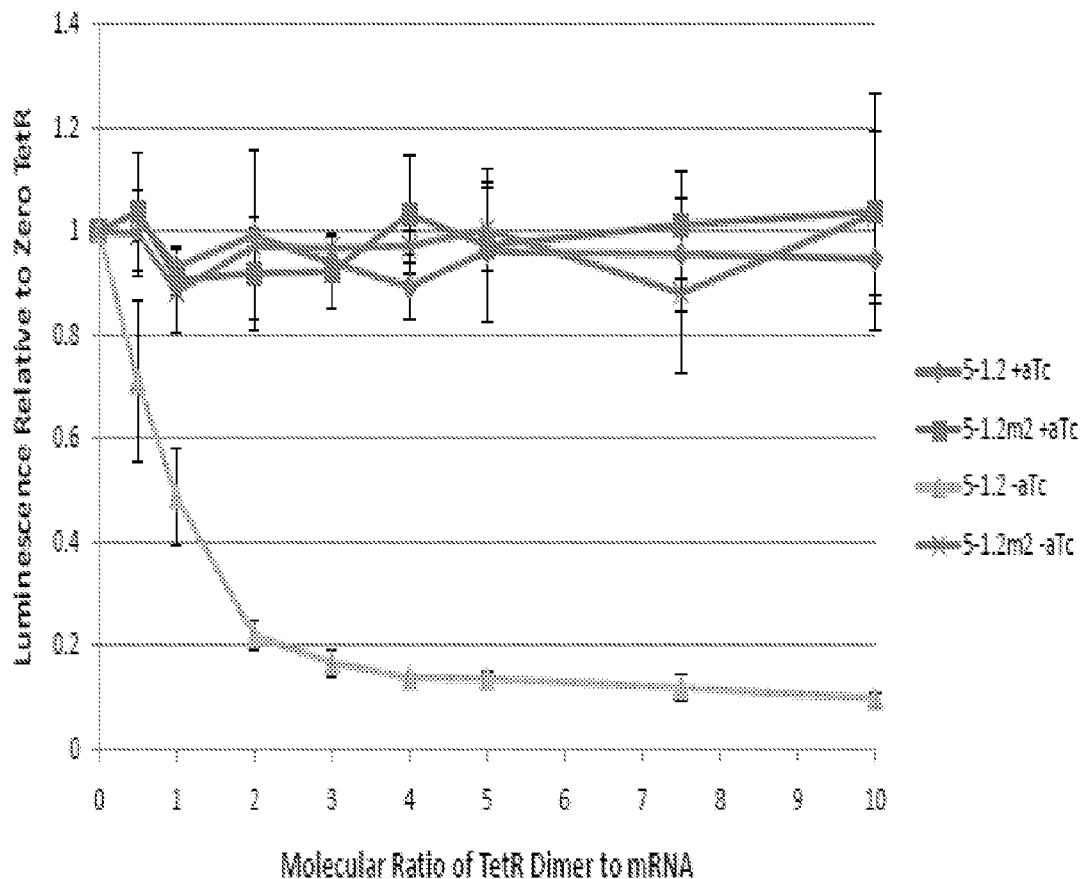
FIG. 7 presents exemplary data of a cell-free translation system demonstrating translational repression of tetracycline repressor protein from mRNA comprising a tetracycline repressor protein binding aptamer. Data represent the mean and standard deviation of at least three experiments. Effects of anhydrotetracycline (aTc) are shown using either a mutant tetracycline repressor binding aptamer (5-1.2m2) or a biologically active tetracycline repressor protein binding aptamer (5-1.2) on the translation of firefly luciferase mRNA. Avg±SEM.

In one embodiment, the present invention contemplates an in vitro method for creating an mRNA sequence encoding an aptamer comprising a high affinity TetR binding site in a rabbit reticulocyte cell-free translation system. An RNA sequence may further encode a firefly luciferase protein (FLuc), wherein the translation of FLuc from this mRNA can be specifically regulated in a dose-dependent manner by the addition of the mRNA and/or purified tetracycline repressor protein. See, FIG. 7.

The data presented herein demonstrates a TetR dose-dependent reduction of luminescence reporter signal when the mRNA comprises a TetR binding site aptamer (5-1.2) versus a mutant aptamer (5-1.2m2). See, FIG. 7. Further studies show that this decreased translation is not observed in the presence of a tetracycline-based compound (i.e., for example, anhydrotetracycline) and/or in the presence of a mutant TetR aptamer (i.e., for example, 5-1.2m2). See, FIG. 7. Specifically, increasing concentrations of TetR were added to mRNA encoding the luminescent reporter firefly luciferase. Cell-free translation with the rabbit reticulocyte system was then carried out in the presence or absence of 1 µM anhydrotetracycline. mRNA containing the TetR-binding aptamer 5-1.2 exhibited dose-dependent repression, whereas translation of mRNA containing the binding-defective mutant 5-1.2m2 is unaffected by TetR. The data also demonstrate that Fluc translation is increased after addition of tetracycline. See, FIG. 7B. Although it is not necessary to understand the mechanism of an invention, it is believed that the tetracycline reduces TetR-aptamer binding stability and thereby permits an increased rate of downstream translation.

It should be noted that TetR-binding activity of an isolated aptamer does not imply binding or repression activity in the mRNA context. For example, 5-1.2 and 5-11.2 both bound TetR with dissociation constants between 1 and 5 nM, but 5-11.2 displayed no repression activity See, Table 1 (infra).

Although it is not necessary to understand the mechanism of an invention, it is believed that the maximum dynamic range achieved using this system is at least 10, which is very similar to that of the IRE/IRP interaction in vivo, but several-fold less than what has been reported for the IRE/IRP interaction in a cell-free system. Paraskeva et al., "A translational repression assay procedure (TRAP) for RNA-protein interactions in vivo" *Proc Natl Acad Sci USA* 95:951-956 (1998); and Kim et al., "Translational repressor activity is equivalent and is quantitatively predicted by in vitro RNA binding for two iron-responsive element binding proteins, IRP1 and IRP2" *J Biol Chem* 270:4983-4986 (1995), respectively.

1. Parameter Optimization a The AUG Codon

The data presented herein suggest that TetR binding aptamers selected thus far conferring significant repressor activity contain at least one AUG codon. Although TetR binding aptamers may contain one or more AUG codons and still function to enable ligand-regulated TetR-RNA binding, one may eventually wish to eliminate all AUG codons from an aptamer so that protein translation may be initiated outside of the aptamer sequence. While a set of aptamers having no AUG codons retain affinity for TetR, little or no translation repression was observed when using these particular mutants. See, Table I, Example XI.

b. Folding Stability

In certain embodiments, the present invention contemplates placing a ligand inducible regulatory protein binding aptamer within the endogenous 5'-UTR of a gene of interest while retaining the gene's native promoter region. Although it is not necessary to understand the mechanism of an invention, it is believed that this construct likely retains wild-type transcript levels and regulation. It is generally believed that when inserting structured RNA into a 5'-UTR of a transcript, protein translation levels may be reduced. Babendure et al, "Control of mammalian translation by mRNA structure near caps" *RNA* 12:851-861 (2006). Additionally, it has been shown with non-inducible aptamer-protein pairs that increasing the RNA folding stability reduces basal gene expression levels, while retaining modest regulation of expression when the protein partner is bound. Koloteva et al., "The position dependence of translational regulation via RNA-RNA and RNA-protein interactions in the 5'-untranslated region of eukaryotic mRNA is a function of the thermodynamic competence of 40S ribosomes in translational initiation" *J Biol Chem* 272: 16531-16539 (1997). This decrease in the regulated protein level could adversely affect any related cellular phenotypes, and would preferably be avoided.

In some embodiments, the present invention contemplates methods to identify aptamer structures that undergo proper folding and controllable gene expression regulation by ligand inducible protein binding aptamers. Further, when inserted into an mRNA, the mRNA-aptamer construction retains endogenous levels of protein translation in vivo. By systematically altering the aptamer stem, the folding energy can be increased or decreased thereby deriving relationships between ΔG of folding, basal expression and regulation by TetR. See, FIG. 15. Sequence-specific correlations may be ruled out by creating aptamers with similar folding stabilities but different sequences. For example, the ΔG could be reduced by changing a G-C stem pair to an A-U, and also by merely shortening the stem. Another approach would be to retain folding stability, but alter the sequence (i.e., for example, G-C to C-G stem substitutions) in a manner expected to have no effect on folding energy. Another option for stem optimization is to insert the loop region of a TetR-binding aptamer onto natural RNA stems (i.e. IRE stem) that appear to have negligible impact on expression.

c. Aptamer Placement

Position of an aptamer within the 5'-UTR, relative to both the 5' cap and the downstream start codon, can influence the functionality of a protein-aptamer translation regulation system. Goossen et al., "Position is the critical determinant for function of iron-responsive elements as translational regulators" *Mol Cell Biol* 12:1959-66 (1992). Although it is not necessary to understand the mechanism of an invention, it is believed that aptamer position dependence may play a role in optimizing higher eukaryote gene expression platforms. In some embodiments, the present invention contemplates optimizing aptamer placement with respect to both the magnitude of regulation and basal expression level. For example, reporter constructs may be built which contain an aptamer at various locations within the 5'-UTR, between 0 to 100 bases from the cap or start codon. While non-AUG aptamers are preferable, the downstream region after the aptamer can be retained in order to preserve the peptide leader sequence, thereby limiting alteration to the upstream sequence relative to the aptamer.

d. Aptamer Copy Number

Another system parameter amenable to optimization is the copy number of aptamers placed in the 5'-UTR of a transcript. Previous reports show that using a single small-molecule binding aptamer in the 5'-UTR enables 8-fold repression upon ligand addition, but using three aptamers causes a 37-fold repression Kotter et al., "A fast and efficient translational control system for conditional expression of yeast genes" Nucleic Acids Res;37(18):e120 (2009). Analogously, increasing the number of TetR-binding aptamers in the mRNA could also impact system functionality. Consequently, optimizing reporter construct vectors should contain one, two, or three aptamers. These constructs will be used to measure both basal level of expression and regulatory range in the presence of TetR.

e. Mutagenesis of the 5'-UTR

In some embodiments, methods for aptamer optimization comprises investigating sequence diversity, for example, in the aptamer loop region (putative TetR binding site), aptamer flanking sequences (to promote proper folding), and the region corresponding to the N-terminal leader peptide. For example, the 5'-UTR area may be targeted in an unbiased manner by performing random mutagenesis and/or DNA shuffling, optionally coupled with an in vivo selection. Although it is not necessary to understand the mechanism of an invention, it is believed that multiple rounds of mutagenesis can be performed, wherein each round starts with the previous round's optimal candidate in order to direct the evolution of an aptamer with the desired parameters. For example, screening of a library of yeast can be conducted with URA3 as the reporter and a positive/negative dual selection scheme. This approach may allow titration of both uracil and 5-FOA to isolate aptamers with desired characteristics.

C. Regulation of an In Vivo Eukaryotic Single Gene-Mediated Phenotype

Figure 8:
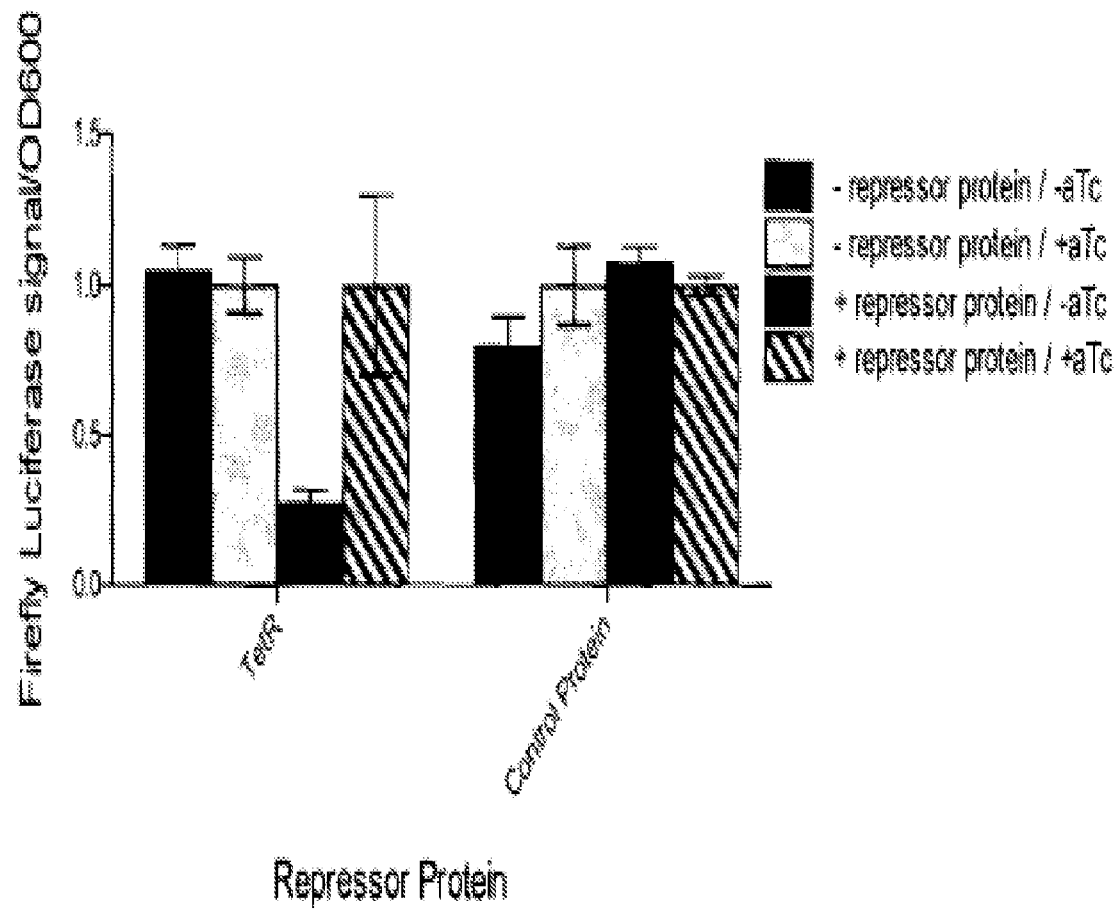
FIG. 8 presents exemplary data showing in vivo translation repression in a eukaryotic protein expression system (i.e., for example, *S. cerevisiae*) with a tetracycline repressor protein and a TetR-binding aptamer. Bar 1: −TetR/−aTc; Bar 2: −TetR/+ aTc; Bar 3: +TetR/−aTc; Bar 4: +TetR/+aTc.

In one embodiment, the present invention contemplates an in vivo method for expressing plasmid DNA encoding an mRNA sequence (i.e., for example, an aptamer) comprising a high affinity TetR binding site fused to an open reading frame for a protein of interest in a yeast platform (i.e., for example, *Saccharomyces cerevisiae*). The data presented herein show that the expression of firefly luciferase is specifically regulated by the addition of a tetracycline-based compound to the growth media. See, FIG. 8. Specifically, the data show that only the combination of TetR and the absence of anhydrotetracycline resulted in a reduction of firefly luciferase protein.

This preliminary data in yeast suggested that ligand-inducible protein-aptamer complexes can have wide ranging scientific and industrial applicability involving organisms including but not limited to fungi, mammals, plants, and parasites. For example, it has been reported that a functional yeast system comprising a protein effector and a 5'-UTR located aptamer is operable in mammalian cells. Stripecke et al., "Protein binding to 5' untranslated region sites: a general mechanism for translational regulation of mRNAs in human and yeast cells" *Mol. Cell. Biol.* 14: 5898-5909 (1994).

Figure 12:
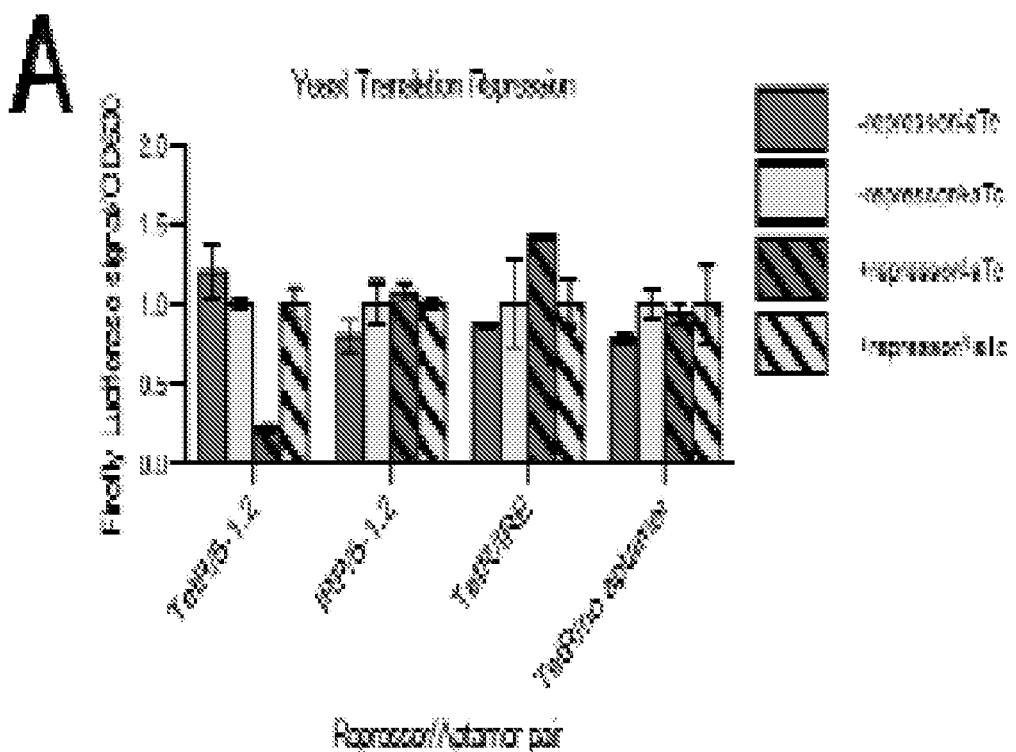
FIG. 12 presents exemplary data of anhydrotetracycline effects on luciferase expression using various embodiments of TetR-aptamer constructs.
Figure 12:
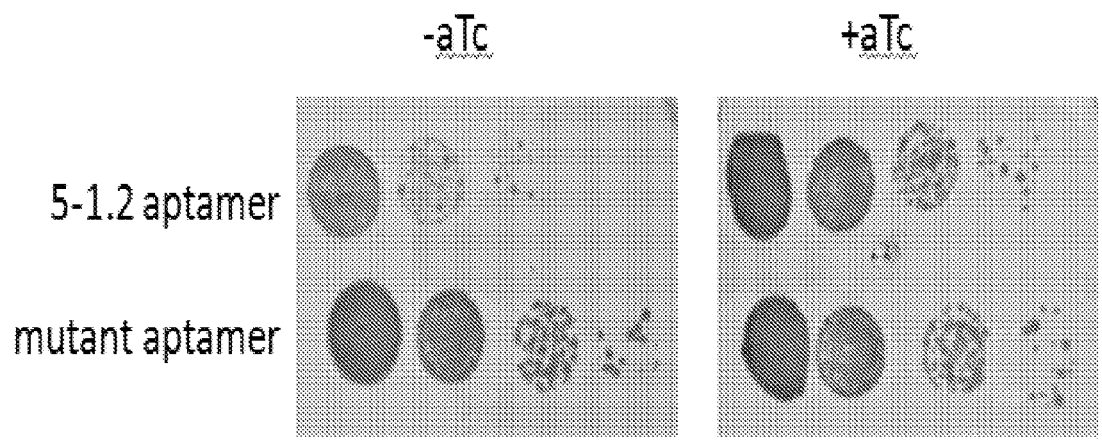
Figure 12:
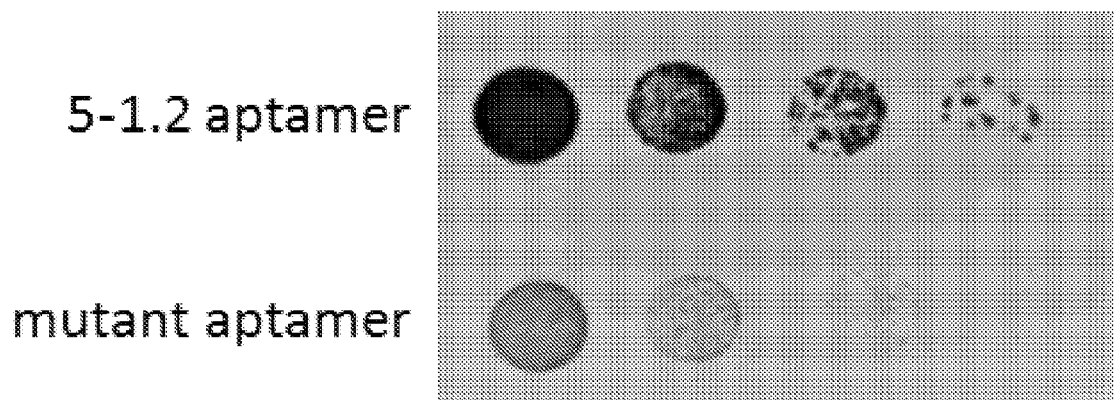

To further develop a eukaryotic system, a single TetR-binding aptamer was genetically encoded (i.e., for example, ligated) within a 5' UTR of a reporter gene (i.e., for example, firefly luciferase). The 5-1.2 truncated aptamer was tested wherein a W303 yeast strain was co-transformed with: i) a vector containing the aptamer-reporter coding region under the control of the strong constitutive TEF1 promoter; and ii) a vector containing the TetR protein under control of a galactose inducible promoter. As a control, the IRE-BP was used in place of TetR, as it was expected that IRE-BP protein would have no effect on reporter expression. Cells were grown in the presence or absence of galactose to control repressor protein expression and 1 μM aTc to reverse the TetR-aptamer interaction. When the 5-1.2 aptamer was used in the absence of TetR, luciferase signal was largely invariant with respect to aTc. But under conditions of TetR expression, reporter signal was repressed 78%. ATc addition reversed this repression. See, FIG. 12A. Aptamers 5-1 and 5-11 were also tested, and similar repression as that seen with 5-1.2 was observed (data not shown).

As the aptamers 5-1 and 5-11 were derived from two distinct parent TetR-binding aptamers, these data suggest that the concept of ligand modulation of regulatory protein-aptamers within mRNA sequences should be adaptable to a wide range of aptamers. It should be noted that TetR expression does not affect general reporter expression, as replacement of the TetR-binding aptamer with an IRE failed to repress luciferase activity. See, FIG. 12A. Furthermore, IRP expression exerts no regulation on an mRNA containing a TetR-binding aptamer, suggesting that TetR directly mediates the observed regulation by specifically interacting with its cognate aptamer (data not shown). To show that this regulation is independent of reporter gene, a URA3 ORF was placed downstream of the aptamer. Since W303 cells carry a mutated URA3 gene, complementation by a wild-type gene should allow for growth on media lacking uracil (-ura). Indeed, when grown on uracil dropout media, cells harboring the 5-1.2 aptamer/URA3 construct grow in an aTc-dependent manner. See, FIG. 12B. This dependence is not observed when the aptamer is mutated to prevent TetR binding. Furthermore, this system can be used in a counter-selection scheme in which the cells harboring the 5-1.2 aptamer/URA3 construct are grown on media containing the antimetabolite, 5-fluoroorotic acid (FOA). Cells with repressed URA3 gene expression grow at a faster rate than those with higher URA3 gene expression as expected. See, FIG. 12C. Thus, these data support inducible translation regulation within a eukaryotic context.

D. Regulation of Multiple Targets in a Simultaneous, Orthogonal Manner

In one embodiment, the present invention contemplates a method for creating a plurality of mRNA sequences wherein each mRNA sequence encodes an open reading frame from a different gene of interest and a different RNA aptamer, wherein each aptamer comprises a high affinity binding site for a different repressor protein. In one embodiment, the method is performed in a single cell system. In one embodiment, the method is performed in a cell-free system. In such a method, the present invention contemplates performing simultaneous orthogonal regulation of multiple gene products by adding multiple regulatory compounds. Although it is not necessary to understand the mechanism of an invention, it is believed that as long as these regulatory compounds have little effect on endogenous biology (i.e., for example, antiprokaryotic antibiotics such as tetracycline and/or erythromycin; or a biologically inert signaling molecule such as ecdysone) the cell system will remain largely independent of endogenous gene regulation.

E. Biosensor Systems

In one embodiment, the present invention contemplates a method for utilizing a composition comprising a nucleic acid sequence encoding an aptamer attached to a repressor protein that responds to an endogenously-produced factor, such that a reporter gene and/or desired metabolic activity can be regulated in response to the state of a particular aspect of a cellular or cell-free system.

F. Metabolic Engineering Systems

In one embodiment, the present invention contemplates a method for utilizing a composition comprising a nucleic acid sequence encoding an aptamer attached to a repressor protein that responds to an endogenously-produced factor, wherein a desired metabolic activity can be regulated in response to the state of a particular aspect of a cellular or cell-free system. For example, the method can dynamically regulate the levels of particular enzymatic activities in a system in response to the concentration of a particular reactant or intermediate in order to maximize the yield and/or productivity of a desired target compound. Although it is not necessary to understand the mechanism of an invention, it is believed that the method can create a self-optimizing system of metabolic processes that enables the optimal production of a desired target compound.

G. Subcellular RNA Localization Regulation

In one embodiment, the present invention contemplates a method for utilizing a repressor protein and/or a repressor protein fusion protein comprising subcellular localization activity wherein a ligand inducible regulatory protein binding aptamer comprising an mRNA sequence of interest can be localized to a specific intracellular location and/or compartment. In one embodiment, the intracellular location comprises the nuclear region. In one embodiment, the intracellular location comprises the plasma membrane. In one embodiment, the intracellular location comprises the endoplasmic reticulum. In one embodiment, the intracellular location comprises the mitochondria. In one embodiment, a diffusive distribution of a target mRNA-aptamer is localized to an intracellular compartment by the addition and/or removal of a regulatory compound. In one embodiment, the localized distribution of a target mRNA-aptamer is diffusively distributed into the intracellular space by the addition and/or removal of a regulatory compound.

Another strategy involves the use of a multifunctional repressor protein capable of both binding the aptamer and effecting some additional function. For example, an aptamer-binding protein fusion bearing a functional nuclear localization signal (NLS) may be used. A particular example involves TetR fused to a functional NLS. By expressing such a protein in a yeast strain or other cell line that also expresses a gene of interest under the control of a TetR-binding aptamer (either in the 5' or 3' UTR), an inducible targeting of the aptamer-containing mRNA to the nucleus may occur, thereby decreasing the mRNA's steady-state cytoplasmic concentration and concomitantly decreasing translation. This system would recapitulate one aspect of a natural mechanism whereby the influenza virus protein NS1 binds polyadenylated host mRNAs and retains them in the nucleus. Marion et al., "The N-terminal half of the influenza virus NS1 protein is sufficient for nuclear retention of mRNA and enhancement of viral mRNA translation" Nucl. Acids Res. 25:4271-4277 (1997); and Qiu et al., "The influenza virus NS1 protein is a poly(A)-binding protein that inhibits nuclear export of mRNAs containing poly(A)" J. Virol. 68:2425-2432 (1994). Such a decrease in translation would be reversed by the addition of an inducer (for example, a tetracycline) thereby causing the aptamer-containing mRNA to dissociate from the nuclear localized protein and move throughout the cell.

In another example, an aptamer-binding protein bearing a functional nuclear anchoring domain may be used. A particular example involves TetR fused to a C-terminal fragment of the S. cerevisiae Esc1p protein. EMBO J. 23:1301-1312 (2004). By expressing such a protein in a yeast strain or other cell line that also expresses a gene of interest under the control of a TetR-binding aptamer (either in the 5' or 3' UTR), an inducible targeting of the aptamer-containing mRNA to inner face of the nuclear membrane may occur, thereby decreasing the mRNA's steady-state cytoplasmic concentration and concomitantly decreasing translation. Such a decrease in translation would be reversed by the addition of an inducer (for example, a tetracycline) thereby causing the aptamer-containing mRNA to dissociate from the nuclear anchored protein and move throughout the cell.

Once localization of a fusion construct is confirmed, transient transfection experiments can be performed as described herein in order to determine if repression of a target mRNA has been alleviated. Although this system might be expected to impart minimal repression of basal (i.e., for example, fully induced) gene expression, the fate of a nuclear-retained mRNA is unknown when released from TetR as well as the relative kinetics. It has been reported that, in mammalian cells, splicing greatly stimulates export of mRNAs from the nucleus, but it is unclear whether retaining a spliced transcript in the nucleus for a period of minutes or hours would diminish or eliminate this effect, resulting in delayed export after release from TetR. Kataoka et al., "Pre-mRNA Splicing Imprints mRNA in the Nucleus with a Novel RNA Binding Protein that Persists in the Cytoplasm" Molecular Cell 6:673-682 (2000); and Valencia et al., "Splicing promotes rapid and efficient mRNA export in mammalian cells" Procd Natl Acad Sci USA 105: 3386-3391 (2008). Nevertheless, inducible sequestration of mRNA may be a valuable mechanism for PBRA-based gene regulation that decouples inducible expression from the process of translation initiation.

H. Cellular RNA Metabolism Targeting

In one embodiment, the present invention contemplates a method for utilizing a repressor protein and/or repressor protein fusion protein that interact with RNA metabolism genes. In one embodiment, the RNA metabolism genes may be selected from the group including, but not limited to, ribonuclease, RNA-dependent RNA polymerase, reverse transcriptase, polyadenylyl polymerase (PAP). In one embodiment, the RNA metabolism genes comprise inhibitors of genes selected from the group including, but not limited to, ribonuclease, RNA-dependent RNA polymerase, reverse transcriptase, polyadenylyl polymerase (PAP). In one embodiment, the RNA metabolism genes are targeted specifically by aptamer-containing mRNA of interest in a manner that is regulated by the addition or removal of a regulatory substance. In one embodiment, a repressor protein is fused to a RNase A protein, wherein the degradation rate of a target mRNA is greatly increased, thereby yielding low steady state levels of the target mRNA and, therefore, low protein expression levels. In one embodiment, the repressor protein is fused to a protein (i.e., for example, the 70K protein) of a U1 small nuclear ribonucleoprotein complex (snRNP). In another embodiment, the repressor protein is fused to a non-U1 snRNP-derived protein or protein fragment (for example, U2AF65). Although it is not necessary to understand the mechanism of an invention, it is believed that by generating target mRNA containing the repressor protein-binding aptamer in the 3' UTR, the repressor protein-70K fusion protein binds the 3' end of the mRNA, thereby allowing the 70K protein to inhibit PAP activity at the 3' end of the mRNA. *Nucl. Acids Res.* 36:2338-2352 (2008). This specific inhibition would be regulated by the addition or removal of a regulatory substance.

I. Intracellular Non-Coding RNA Molecule Activity

In one embodiment, the present invention contemplates a method for fusing a repressor protein-binding aptamer to a noncoding RNA comprising an intracellular activity. In one embodiment, the intracellular activity comprises gene expression. In one embodiment, the noncoding RNA intracellular activity is selectively activated or deactivated by permitting or blocking repressor protein-aptamer binding using a regulatory compound.

J. Extracellular Noncoding RNA Molecule Activity

In one embodiment, the present invention contemplates a method for fusing a repressor protein-binding aptamer to a noncoding RNA region comprising an extracellular activity. In one embodiment, the extracellular activity comprises binding to a second aptamer. In one embodiment, the second aptamer comprises a therapeutic agent binding site. Although it is not necessary to understand the mechanism of an invention, it is believed that a noncoding RNA sequence comprising a repressor protein-binding aptamer can be regulated by, for example, blocking a regulatory compound binding site and/or inhibiting a regulatory compound-induced secondary structure conformational change in the presence or absence of repressor protein binding. In one embodiment, the aptamer-based therapeutic agent is regulated by a repressor protein-aptamer pair.

V. Inducible Protein-Aptamer Complexes in Human Cells

In one embodiment, the present invention contemplates compositions and methods for translation control using a ligand inducible regulatory protein binding aptamer system in human cells. Gene expression in human cells has been reported using non-inducible protein-RNA interactions. Nie et al., "Different modes and potencies of translational repression by sequence specific RNA-protein interaction at the 5'-UTR" *Nucl. Acids Res.* 34:5528-5540 (2006). For example, the endogenous IRE/IRP iron regulatory system, which is based upon protein-RNA interactions, occurs in humans. Rouault, T. A., "The role of iron regulatory proteins in mammalian iron homeostasis and disease" *Nat. Chem. Biol* 2:406-414 (2006).

In one embodiment, a human mRNA aptamer complex comprises a bicistronic reporter encoding an internal ribosome entry site (TRES). In one embodiment, the IRES is derived from the encephalomyocarditis virus (EMCV). See, FIG. 13A; Bochkov et al., "Translational efficiency of EMCV IRES in bicistronic vectors is dependent upon IRES sequence and gene location" *BioTechniques* 41:283-288 (2006). Although it is not necessary to understand the mechanism of an invention, it is believed that an IRES can promote translation of a coding sequence that is located downstream of another ORF within a single mRNA. In one embodiment, an aptamer contemplated herein regulates translation of the first reporter, thereby leaving the second reporter constitutively expressed. This configuration provides an internal control for transcript levels.

In one embodiment, the present invention contemplates a composition comprising an HEK-293 cell transfected with a plasmid comprising an mRNA sequence in operable combination with an aptamer sequence, wherein the aptamer sequence comprises a high affinity regulatory protein binding site. In one embodiment, the HEK-293 cell is transfected with a second plasmid comprising a constitutively expressed reporter. In one embodiment, the first plasmid and second plasmid are transfected simultaneously. In one embodiment, the first plasmid and second plasmid are transfected serially. The efficiency of translation repression and the optimal TetR concentration required for achieving this can be determined using established methods. Nie et al., "Different modes and potencies of translational repression by sequence specific RNA-protein interaction at the 5'-UTR" *Nucl. Acids Res.* 34:5528-5540 (2006). In one embodiment, the present invention contemplates a composition and method for integrating a functional regulatory protein-aptamer expression cassette into genomic DNA. In one embodiment, the expression cassette is integrated using a lentiviral system. Although it is not necessary to understand the mechanism of an invention, it is believed that construction of a transfected human cell line reduces TetR expression heterogeneity that will facilitate system optimization.

VI. Industrial Applicability

In some embodiments, the present invention can be used as a biosensor for exogenous or endogenous compounds. Environmental safety monitoring and medical diagnostic devices are two applications in which such a biosensor, sensitive to a compound of particular interest, would be highly useful.

In some embodiments, the present invention can be used advantageously as a research tool, especially in manipulating poorly characterized organisms or those lacking robust gene regulation technology.

In some embodiments, the present invention can be used in metabolic engineering, particularly in applications relating to bioprocess regulation. For example, it is frequently desirable to modulate certain biological functions of an organism during industrial fermentation or cell culture, in response to the accumulation of a intermediary metabolite and/or product. By using the present invention to construct a system containing a repressor protein sensitive to such compounds, and an aptamer that binds the repressor protein, one could construct one or more auto-regulatory circuits within the production organism that allows autonomous process optimization.

In some embodiments, the present invention can be used to regulate the activity of RNA aptamer-based therapeutics. Aptamer-based therapeutics are in commercial development (Archemix) that could be potentially improved using the presently disclosed regulatable aptamer-protein interaction system. In some embodiments, the presently disclosed system can be used to enhance the potency and specificity of aptamer-based therapeutics.

Metabolic engineering methodologies are routinely used in the development of improved bioproduction strains (Amyris, LS9, and Metabolix). In some embodiments, the presently disclosed system would facilitate this research and development process, as well as improve the efficiency of small-scale bioproduction of target materials.

The precise, repeatable control of bioproduction organisms is necessary for the fermentation-derived bulk chemicals and/or manufacture of pharmaceutical biologics (Cargill, ADM, Genzyme, Biogen, and Merck). In some embodiments, the presently disclosed system would improve the controllability of such bioproduction techniques.

VII. Detection Methodologies

A. Detection of Nucleic Acids mRNA expression may be measured by any suitable method, including but not limited to, those disclosed below.

In some embodiments, RNA is detected by Northern blot analysis. Northern blot analysis involves the separation of RNA and hybridization of a complementary labeled probe.

In other embodiments, RNA expression is detected by enzymatic cleavage of specific structures (INVADER assay, Third Wave Technologies; See e.g., U.S. Pat. Nos. 5,846,717, 6,090,543; 6,001,567; 5,985,557; and 5,994,069; each of which is herein incorporated by reference). The INVADER assay detects specific nucleic acid (e.g., RNA) sequences by using structure-specific enzymes to cleave a complex formed by the hybridization of overlapping oligonucleotide probes.

In still further embodiments, RNA (or corresponding cDNA) is detected by hybridization to an oligonucleotide probe. A variety of hybridization assays using a variety of technologies for hybridization and detection are available. For example, in some embodiments, TaqMan assay (PE Biosystems, Foster City, Calif.; See e.g., U.S. Pat. Nos. 5,962,233 and 5,538,848, each of which is herein incorporated by reference) is utilized. The assay is performed during a PCR reaction. The TaqMan assay exploits the 5'-3' exonuclease activity of the AMPLITAQ GOLD DNA polymerase. A probe consisting of an oligonucleotide with a 5'-reporter dye (e.g., a fluorescent dye) and a 3'-quencher dye is included in the PCR reaction. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each PCR cycle and can be monitored with a fluorimeter.

In yet other embodiments, reverse-transcriptase PCR (RT-PCR) is used to detect the expression of RNA. In RT-PCR, RNA is enzymatically converted to complementary DNA or "cDNA" using a reverse transcriptase enzyme. The cDNA is then used as a template for a PCR reaction. PCR products can be detected by any suitable method, including but not limited to, gel electrophoresis and staining with a DNA specific stain or hybridization to a labeled probe. In some embodiments, the quantitative reverse transcriptase PCR with standardized mixtures of competitive templates method described in U.S. Pat. Nos. 5,639,606, 5,643,765, and 5,876,978 (each of which is herein incorporated by reference) is utilized.

B. Sequencing of Nucleic Acids

The method most commonly used as the basis for nucleic acid sequencing, or for identifying a target base, is the Sanger chain-termination method. Traditionally, such methods relied on gel electrophoresis to resolve nucleic acid fragments generated from a larger nucleic acid template at single nucleotide resolution. However, in recent years various sequencing technologies have evolved which rely on a range of different separation and detection strategies, such as capillary electrophoresis with fluorescence detection, which remains the most common method used during aptamer development and characterization, as well as for routinely verifying genetically encoded constructs generated in the laboratory.

One class of sequencing methods assuming importance in the art are those which rely upon the detection of PPi release as the detection strategy. It has been found that such methods lend themselves admirably to large scale genomic projects, where relatively cost-effective units with high throughput are needed.

Methods of sequencing based on the concept of detecting inorganic pyrophosphate (PPi), which is released during a polymerase reaction, have been described in the literature for example (WO 93/23564, WO 89/09283, W098/13523 and WO 98/28440). As each nucleotide is added to a growing nucleic acid strand during a polymerase reaction, a pyrophosphate molecule is released. It has been found that pyrophosphate released under these conditions can readily be detected, for example enzymatically e.g. by the generation of light in the luciferase-luciferin reaction. Such methods enable a base to be identified in a target position and DNA to be sequenced simply and rapidly whilst avoiding the need for electrophoresis and the use of labels.

At its most basic, a PPi-based sequencing reaction involves simply carrying out a primer-directed polymerase extension reaction, and detecting whether or not that nucleotide has been incorporated by detecting whether or not PPi has been released. Conveniently, this detection of PPi-release may be achieved enzymatically, and most conveniently by means of a luciferase-based light detection reaction termed ELIDA (see further below).

It has been found that dATP added as a nucleotide for incorporation, interferes with the luciferase reaction used for PPi detection. Accordingly, a major improvement to the basic PPi-based sequencing method has been to use, in place of dATP, a dATP analogue (specifically dATPα's) which is incapable of acting as a substrate for luciferase, but which is nonetheless capable of being incorporated into a nucleotide chain by a polymerase enzyme (W098/13523).

Further improvements to the basic PPi-based sequencing technique include the use of a nucleotide degrading enzyme such as apyrase during the polymerase step, so that unincorporated nucleotides are degraded, as described in WO 98/28440, and the use of a single-stranded nucleic acid binding protein in the reaction mixture after annealing of the primers to the template, which has been found to have a beneficial effect in reducing the number of false signals, as described in W000/43540.

C. Protein Detection

In other embodiments, gene expression may be detected by measuring the expression of a protein or polypeptide. Protein expression may be detected by any suitable method. In some embodiments, proteins are detected by immunohistochemistry. In other embodiments, proteins are detected by their binding to an antibody raised against the target protein.

Antibody binding may be detected by many different techniques including, but not limited to, (e.g., radioimmunoassay, ELISA (enzyme-linked immunosorbant assay), "sandwich" immunoassays, gel diffusion precipitation reactions, immunodiffusion assays, in situ immunoassays (e.g., using colloidal gold, enzyme or radioisotope labels, for example), Western blots, immunoprecipitation reactions, agglutination assays (e.g., gel agglutination assays, hemagglutination assays, etc.), immunofluorescence assays, protein A assays, and immunoelectrophoresis assays, etc.

In one embodiment, antibody binding is detected via a label on the primary antibody. In another embodiment, the primary antibody is detected via binding of a labeled secondary antibody or reagent to the primary antibody.

In some embodiments, an automated detection assay is utilized. Methods for the automation of immunoassays include those described in U.S. Pat. Nos. 5,885,530, 4,981,785, 6,159,750, and 5,358,691, each of which is herein incorporated by reference. In some embodiments, the analysis and presentation of results is also automated. For example, in some embodiments, software that generates a prognosis based on the presence or absence of a series of proteins corresponding to cancer markers is utilized.

In other embodiments, the immunoassay described in U.S. Pat. Nos. 5,599,677 and 5,672,480 are used, both herein incorporated by reference.

E. Detection Kits

In other embodiments, the present invention provides kits for the detection and characterization of proteins and/or nucleic acids. In some embodiments, the kits contain antibodies specific for a protein expressed from a gene of interest, in addition to detection reagents and buffers. In other embodiments, the kits contain reagents specific for the detection of mRNA or cDNA (e.g., oligonucleotide probes, primers, plasmids). In preferred embodiments, the kits contain all of the components necessary to perform a detection assay, including all controls, directions for performing assays, and any necessary software for analysis and presentation of results.

VIII. Pharmaceutical Compositions and Formulations

The present invention further provides pharmaceutical compositions (e.g., comprising the plasmid or nucleic acid compositions described above). The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

Agents that enhance uptake of oligonucleotides at the cellular level may also be added to the pharmaceutical and other compositions of the present invention. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on $EC_{50}$s found to be effective in vitro and in animal models or based on the examples described herein. In general, dosage is from 0.01 µg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the oligonucleotide is administered in maintenance doses, ranging from 0.01 µg to 100 g per kg of body weight, once or more daily, to once every 20 years.

EXPERIMENTAL

All oligonucleotides were purchased from Integrated DNA Technologies. Fluorescein-5 thiosemicarbazide for fluorescently labeling RNA was from Marker Gene Technologies. All chemicals used were analytical or molecular biology grade.

Example I

Recombinant Tetracycline Repressor Protein Expression and Purification

The tetracycline repressor protein (TetR) gene was cloned into pET24a(+) (EMD Chemicals) vector between the EcoRI and HindIII sites, and this construct used to produce recombinant TetR-His$_6$ with an N-terminal T7 tag. Briefly, BL21 (DE3) cells harboring the pET24a-TetR-His$_6$ plasmid were grown to an OD$_{600}$=0.5-0.7 in Terrific Broth® media containing 50 µg/mL kanamycin before induction with 1 mM IPTG and further grown at 37° C. for 5 hours. Cells were harvested by centrifugation, resuspended in lysis buffer (50 mM Tris-HCl, 100 mM NaCl, 5% glycerol, 5 mM β-mercaptoethanol, 1 mM imidazole, pH 8 and Protease Inhibitor Cocktail VII (Research Products International Corp.)) and lysed using sonication. The lysate was cleared by centrifugation and the supernatant loaded onto a Ni-NTA column pre-equilibrated in lysis buffer. The column was washed with 20 column volumes of washing buffer (10 mM imidazole in lysis buffer) before eluting TetR with 500 mM imidazole in lysis buffer. Suitably pure fractions (>90%) TetR, as determined by SDS-PAGE analysis, were pooled, concentrated and buffer exchanged using 10,000 MWCO Amicon Ultra® spin concentrators (Millipore) into 20 mM Tris-HCl (pH 8), 200 mM NaCl, 5 mM DTT and 50% glycerol prior to storage at −20° C.

Example II

Systematic Evolution of Ligands by Exponential Enrichment (SELEX)

A single stranded DNA library was used having the sequence:

```
                                              (SEQ ID NO: 1)
CCGAAGCTTAATACGACTCACTATAGGGAGCTCAGAATAAACGCTCAA

[N50]TTCGACATGAGGCCCGGATCCGGC,
``` wherein N=a randomized base. The library was amplified using PCR or reverse transcriptase (RT) PCR as necessary using the primer pair:

```
5' Primer:
                                              (SEQ ID NO: 2)
CCGAAGCTTAATACGACTCACTATAGGGAGCTCAGAATAAACGCTCAA;
And 3' Primer:
                                              (SEQ ID NO: 3)
GCCGGATCCGGGCCTCATGTCGAA.
```

This dsDNA library was made using PCR and, after agarose gel purification, used as template for RNA synthesis using the AmpliScribe® T7-Flash Transcription Kit (Epicentre Biotechnologies).

RNA (i.e., for example, approximately 500-700 pmol) in diethyl pyrocarbonate (DEPC)-treated water was denatured (70° C.×5 min), allowed to cool to room temperature, and refolded in binding buffer (BB): 50 mM Tris-HCl pH 8.0, 50 mM KCl, 5 mM MgCl$_2$, 5 mM β-mercaptoethanol, 5% glycerol, and 0.05% Tween-20. For negative selection, RNA in 500 µL BB was added to ~15 µL pre-washed Ni-NTA magnetic beads (QIAGEN) and incubated at ambient temperature with gentle mixing for 30 min. The supernatant was added to Ni-NTA magnetic beads pre-bound with TetR (i.e., for example, approximately 19-25 pmol) for positive selection, and incubated for 1 hr at ambient temperature with gentle agitation. These beads were washed 5 times with 500 µL BB.

During the first four SELEX rounds, RNA was eluted with 500 mM imidazole in 20 µL BB incubated with the selection beads for 5 minutes. For the fifth and final SELEX round, 100 µM tetracycline in 20 µL BB for 10 minutes was used for elution. RNA was amplified using 4×50 µL Ready-To-Go RT PCR tubes (Amersham) and ~300 pmol each of the 5'- and 3'-primers. RT was carried out at 42° C. for 40 min. The reverse transcriptase was inactivated at 95° C.×15 min, followed by 18 PCR cycles (94° C.×30 s, 57° C.×60 s, 72° C.× 60 s) and a 7 min final extension at 72° C. The RT-PCR products were pooled, concentrated, and purified using 4% agarose gel electrophoresis, and the desired length product was extracted and ethanol precipitated. DNA was resuspended in DEPC-treated H$_2$O for the next round of in vitro transcription. After the fifth round of SELEX, the evolved library was cloned into the pCR2.1-TOPO vector (Invitrogen) and transformed into DH5α *E. coli*. Single colonies were used for mini-prep cultures from which plasmid encoding a single aptamer was isolated for sequencing and archiving.

Example III

Initial Aptamer Binding and Tetracycline Induction

Tetracycline repressor protein (TetR; ~200 pmol) was immobilized on Ni-NTA magnetic beads (QIAGEN) in binding buffer (BB; supra). Refolded RNA (~100 pmol) was added to the protein-bead mixture to a final volume of 500 µL and incubated for 1 h. Supernatant aliquots (~20 µL), removed both before and after tetracycline addition (100 µM for 15 minutes), was mixed with 200 µL of a diluted SYBR Gold® solution (i.e., for example, 1:10,000 dilution SYBR Gold® (Invitrogen) in 10 mM Tris-HCl, pH 8.0). Fluorescence signal was measured (excitation wavelength=490 nm, emission wavelength=537 nm) on a Fluoromax®-2 fluorometer. Binding to TetR is indicated by a decrease in RNA levels in the supernatant.

Example IV

Cytometric Bead-Binding Affinity Assays

Aptamers were transcribed in vitro, and fluorescently labeled at the 3' end as described previously. Pokrovskaya et al., "In vitro transcription: preparative RNA yields in analytical scale reactions" *Anal Biochem* 220:420-423 (1994); and Willkomm D, Hartmann R (2005), eds. Hartmann R, Bindereif A, Schon A, Westhof E (WILEY-VCH Verlag GmbH & Co. KGaA, Weinheim), pp. 86-94, respectively.

Labeled RNA was purified by LiCl/isopropanol precipitation and desalted with a Micro Bio-Spin® P-30 column (Bio-Rad). RNA integrity and purity were verified by denaturing Urea-PAGE analysis. Labeling efficiency and RNA concentration were determined from A$_{260}$ and A$_{492}$ measurements.

Quantitative affinity measurements of aptamer interactions with TetR were performed as described previously. Brodsky et al, "A microbead-based system for identifying and characterizing RNA-protein interactions by flow cytometry" *Mol Cell Proteomics* 1:922-929 (2002); and Warren et al, "A novel binding assay to assess specificity of monoclonal antibodies" *J Immunol Methods* 305:33-38 (2005). Dynabeads TALON® (Invitrogen) (1 μL) were washed with Affinity Binding Buffer (ABB) (BB+10 μg/mL BSA) and centrifuged at 250×g for 2 mins. Beads were resuspended in ABB and incubated with 60 μg of purified His$_6$-tagged TetR for 1 h at room temperature. TetR-coated beads were washed twice and resuspended in ABB. Beads were counted by microscopy, and 70,000 beads were placed per well in a 96-well microplate. Fluorescein-labeled RNA in ABB was added to the beads. Nonspecific RNA interactions were reduced by adding 10 μg/mL yeast tRNA. The binding reaction proceeded with moderate shaking for 4 h at room temperature. Beads were washed once, centrifuged, and resuspended in ABB. Cytometric analysis was performed on an Accuri C6® flow cytometer (Accuri Cytometers Inc.). The median fluorescence intensities of the samples were plotted against RNA or DNA concentration using GraphPad Prism® 5 (GraphPad Software, Inc.).

Dissociation constants were determined by fitting these data using nonlinear regression to Equation 1.

$$Y = B_{max} \cdot \frac{K_d + [L]_0 + [P]_0 - \sqrt{(K_d + [L]_0 + [P]_0)^3 - A[P]_0[L]_0}}{2[P]_0} + NS*[L]_0 + A \quad [1]$$

where $B_{max}$ is the upper limit of the specific binding signal; $K_d$ is the dissociation constant between TetR and the oligonucleotide; $[L]_0$ is the initial oligonucleotide concentration; $[P]_0$ is the initial TetR concentration; NS is the nonspecific binding constant; and A is the background signal intensity of the beads.

Example V

Tetracycline Repressor Protein (TetR) Expression and CAT Reporter Vector Construction The pET24a-TetR vector was modified by replacing the T7 promoter-lacO fragment between the BglII and XbaI sites with a P$_{LlacO}$ promoter fragment. Lutz et al., "Independent and tight regulation of transcriptional units in *Escherichia coli* via the LacR/O, the TetR/O and AraC/I1-I2 regulatory elements" *Nucleic Acids Res* 25:1203-1210 (1997). This permits IPTG-regulated TetR synthesis driven by native *E. coli* RNA polymerase.

The reporter construct was assembled in the pBAD30 vector by inserting the aptamer constructs and CAT gene between the NheI/PstI and PstI/HindIII sites, respectively. The 5-1t aptamer has sequence:

(SEQ ID NO: 4)
GGGCTCCTCTAGTGAAGGCAGAGAAAGGTCGATACGGACGGAATGTGA

TGGCCGGATCC.

The AraC on the vector was truncated at C280 to minimize crosstalk with IPTG. Lee et al., "Directed evolution of AraC for improved compatibility of arabinose-and lactose-inducible promoters" *Appl Environ Microbiol* 73:5711-5715 (2007). All vectors were sequence verified (Massachusetts General Hospital DNA Sequencing Core).

Example VI

*E. coli* Growth Assays

*E. coli* HB101 cells harboring both the tetracycline repressor and CAT reporter vector were grown to saturation. These cells were diluted 1:400 and grown for four hours at 37° C. in Luria Broth (LB) supplemented with 100 μg/mL ampicillin and 50 μg/mL kanamycin for plasmid selection, 0.2% arabinose, and 1 mM IPTG to induce TetR expression and/or 300 nM aTc where appropriate. OD$_{600}$ readings were taken for each culture, and all were diluted 1:500-1:1000 in LB, keeping cell number the same across all inoculations. This LB was supplemented with antibiotics for plasmid selection, 0.2% arabinose, 10 μg/mL Chloramphenicol or 5 μg/mL chloramphenicol with 5-1t mutant #1 to preserve comparable growth rates, and 1 mM IPTG and/or 300 nM aTc where appropriate.

Growth rate was measured by taking OD$_{600}$ readings over time. For CAT activity assays and quantitative PCR experiments, cells were grown overnight and diluted 1:1000 into LB containing 100 μg/mL ampicillin and 50 μg/mL kanamycin for plasmid selection, 0.2% arabinose, and either 1 mM IPTG and/or 300 nM aTc where appropriate. Cultures were incubated at 37° C. for 6 h until harvesting.

Example VII

CAT Activity Assays

Cells were grown to mid-log phase as described above. CAT activity was assayed using the fluorescent FAST-CAT® substrate (Invitrogen). After extraction, products were separated on silica thin layer chromatography plates which were imaged using a Gel Logic® 2200 (Kodak) and quantitated and the Kodak Molecular Imaging Software.

Example VIII cDNA Preparation and Quantitative PCR

Cells were grown to mid-log phase as described above, and RNA stabilized by adding RNA stabilizing solution (i.e., for example, 13 mM EDTA, 10 mM sodium citrate, 3.5 M ammonium sulfate). RNA was extracted using RNeasy® Mini Kits (QIAGEN). Contaminating genomic and plasmid DNA were removed using 10 U TURBO® DNase (Ambion) (2 h at 37° C.), followed by phenol/chloroform extraction and LiCl precipitation.

RNA (2 μg) was reverse transcribed to cDNA using RevertAid® M-MuLV reverse transcriptase (Fermentas). All qPCR reactions were performed using a PTC-200 Peltier Thermal Cycler (MJ Research/BioRad) equipped with a Chromo4 Detector (BioRad).

```
CAT primer pairs were:
                                    (SEQ ID NO: 5)
    5'-ATTCGCAAGATGTGGCGTGTTACG,
    and (SEQ ID NO: 6)
    5'-ACTGGTGAAACTCACCCAGGGATT.

GapA primer pairs were:
                                    (SEQ ID NO: 7)
    5'-TGCTGCTGAAGGCGAAATGAAAGG,
    and (SEQ ID NO: 8)
    5'-AGCATCGAACACGGAAGTGCAAAC.
```

The qPCR reactions were performed in 20 μL and contained: 1× Taq buffer, 2.5 mM MgCl$_2$, 200 μM dNTPs, 100 nM primers, 0.4× SYBR Green®, 0.4 U Taq® polymerase and 10 μL of a 1:100 dilution of the cDNA reaction template solution. The thermocycling program was: 95° C.×2 minutes, followed by 40 cycles of: 95° C.×30 s, 60° C.×30 s, and 72° C.×30 s. SYBR Green® fluorescence was measured, and relative quantitation performed as previously described. Pfaffl M. W., "A new mathematical model for relative quantification in realtime RT-PCR" *Nucleic Acids Res* 29: e45 (2001).

Example XI

Construct Expression Summary

This example presents a data summary of the various constructs tested for TetR-aptamer binding, cell-free translation, and yeast in vivo expression experiments. Translational repression is reported as the luminescence intensity of the uninduced condition relative to the induced condition. The binding of RNA aptamers to TetR was measured by flow cytometry. As can be observed not all the constructs were capable of regulating translation. See, Table 1.

not inducibly repress translation of reporter constructs containing a TetR-binding-aptamer.

Example 10

Flow Cytometry

A flow-cytometry-based technique is used to measure the binding of RNA aptamers to their cognate proteins.

Briefly, a target protein (i.e., for example, TetR) is His-tagged and immobilized on 1-μm Talon (His-tag binding) beads. RNA is then oxidized on its 3' end and the resulting aldehydes are reacted with a fluorescein derivative to yield covalently fluorescently labeled RNA. After mixing the bead-protein complexes with the labeled RNA, flow cytometry is used to quantitate the bead-associated fluorescence, providing equilibrium binding data.

This method may be used to measure the affinity of candidate aptamers for their cognate protein, and to thereby assess

TABLE 1

Summary Of Various TetR-Aptamer Expression Constructs

| Aptamer | Aptamer Sequence | Binding $K_d$ (nM) | Cell-Free Translation (% repression) | Yeast Endpoint (% repression) |
|---|---|---|---|---|
| 5-1.13 SEQ ID NO: 9 | GGGAGCUCAGAAUAAACGCUCAACUCCUGUAGUGAAGGCAGAGAAAGG UCGAUACGGACGGAAUGUGAUGGCCUUCGACAUCAGGCCCGGAUCCGGC | 0.37 | 56 | 75 |
| 5-1.2 SEQ ID NO: 10 | GGAUCCAGGCAGAGAAAGGUCGAUACGGACGGAAUGUGAUGGCCUGGAUCC | 1.6 | 91 | 81 |
| 5-1.2m2 SEQ ID NO: 11 | GGAUCCAGGCAGUGUAAGGUCGAUACGGACGGAAUGUGAUGGCCUGGAUCC | NS | NS | NS |
| 5-11.13 SEQ ID NO: 12 | GGGAGCUCAGAAUAAACGCUCAACUCCUGUAGUGAAGGCAGAGAAAGGUC GAUACGGACGGAAUGUGAUGGCCUUCGACAUCAGGCCCGGAUCCGGC | 1.8 | 21 | 68 |
| 5-14.7b SEQ ID NO: 13 | GGGAGCUGAGAAUAAACGCUCAACAGGAAACAGCAAGACAAACGAUGG GGAGCGUAAGACUGCGAGUGUCGGAUUCGACAUCAGGCCCGGAUCCGGC | 1.44 | NS | NS |
| 5-18.13 SEQ ID NO: 14 | GGGAGCUGAGAAUAAACGCUCAAUAGGGAGAGAACUGUGUCAGAAUGUA GUGAACCAGACACGGAGUGGAGUAUUCGACAUCAGGCCCGGAUCCGGC | 0.45 | NS | 9 |
| 5-29.13a SEQ ID NO: 15 | GGGAGCUCAGAAUAAACGCUCAACUUGCUGCAGAGGGUCGAGAAUAUGU GUGACACUGCGUCGACGGGUUAAGUUCGACAUCAGGCCCGGAUCCGGC | 2.77 | NS | NS |
| Iron Responsive Element (IRE) SEQ ID NO: 16 | CUUAAGCUUCAACAGUGCUUGAACUUAAG | | NS | NS |
| Control (Aptamer-free) | | | | NS |
| IRP/5-1.2 | | | | NS |

NS = not significant (P > 0.05 in an unpaired two-tailed T-test).

Several aptamers, but not the iron-responsive element, bind TetR with high affinity. Aptamers were then inserted into the 5' UTR of mRNA transcripts encoding the firefly luciferase reporter. Reporter expression was measured in a rabbit reticulocyte cell-free system or in *S. cerevisiae* in the presence and absence of the inducer aTc. The iron-responsive protein does the effect of manipulating particular features (i.e., for example, conserved sequences, or sequences predicted to form a stable stem structure) on aptamer-protein interaction. This is important because translation-modulating protein-RNA interactions display high affinity (Kd<50 nM) and destabilization of the aptamer protein interaction will likely decrease regulatory activity. A major technical challenge with this method is the contribution of nonspecific RNA-protein interactions in vitro to observed binding.

Example 11

Rabbit Reticulocyte Lysate (RRL) In Vitro Assay

A commercially prepared RRL (Promega) can be used for the measurement of translation in vitro. A known amount of aptamer-containing reporter mRNA is mixed with a known amount of protein, and then added to the RRL for reporter translation. A reporter comprising a firefly *Photinus pyralis* luciferase (FLuc) gene is advantageous because it is a highly sensitive reporter that has been used previously for in vitro translation repression studies. Ashizuka et al., "Novel Translational Control through an Iron-Responsive Element by Interaction of Multifunctional Protein YB-1 and IRP2" *Mol. Cell. Biol.* 22:6375-6383 (2002). Alternatively, the assay may comprise a control reporter (i.e., for example, *Renilla reniformis* luciferase (RLuc)). Rifo et al., "Back to basics: the untreated rabbit reticulocyte lysate as a competitive system to recapitulate cap/poly(A) synergy and the selective advantage of IRES-driven translation" *Nucl. Acids Res.* 35:e121 (2007). Using this system, inducible protein expression can be measured by adding a known concentration of a ligand (i.e., for example, anhydrotetracycline) to the binding or translation reactions. mRNAs can be constructed by generating template DNA by PCR-based, one-step assembly of oligonucleotides and the template FLuc coding sequence, followed by in vitro transcription with T7 RNA polymerase and addition of a 5' 7Me-Gppp cap with vaccinia capping enzyme. Myette et al., "Domain Structure of the Vaccinia Virus mRNA Capping Enzyme" *J Biol Chem* 271:11936-11944 (1996).

We claim:

1. A method comprising:
   a) providing:
   i) a biological cell comprising a ribonucleic acid sequence encoding an open reading frame for a protein of interest;
   ii) an aptamer sequence ligated within one hundred bases of a 5' cap of said ribonucleic acid sequence, wherein said aptamer sequence comprises a tetracycline inducible protein binding site and a stem loop, wherein said binding site is in a loop portion of said stem loop, wherein said binding site comprises a first nucleotide sequence comprising the 5'-C/U-A/G/U-G/A-A/C/G-A-U/A-G/A-U/A-3' consensus sequence and a second nucleotide sequence comprising the 5'-C/G/U-A/U/G-G-A-G-A-A-3' consensus sequence;
   iii) a tetracycline repressor protein comprising a tetracycline binding site; and
   iv) a tetracycline-based compound, wherein said compound is capable of binding to said tetracycline binding site;
   b) binding said tetracycline repressor protein to said protein binding site wherein translation of said protein of interest is reduced; and
   c) contacting said tetracycline binding site with said tetracycline-based compound under conditions that relieves the translation reduction of said protein of interest.

2. The method of claim 1, wherein said ribonucleic acid sequence further comprises a 5' untranslated region.

3. The method of claim 1, wherein said ribonucleic acid sequence further comprises a 3' untranslated region.

4. The method of claim 1, wherein said tetracycline-based compound is tetracycline.

5. The method of claim 1, wherein said tetracycline-based compound is anhydrotetracycline.

6. The method of claim 1, wherein said biological cell further comprises a plasmid configured to express said protein of interest.

7. The method of claim 1, wherein said tetracycline repressor protein is a fusion protein.

8. The method of claim 7, wherein said fusion protein comprises a translation initiation repressor protein.

9. The method of claim 7, wherein said fusion protein comprises a polyadenylyl polymerase inhibitor protein domain.

* * * * *

UNITED STATES PATENT AND TRADEMARK OFFICE
CERTIFICATE OF CORRECTION

PATENT NO. : 9,125,931 B2
APPLICATION NO. : 12/755121
DATED : September 8, 2015
INVENTOR(S) : Belmont et al.

Page 1 of 1

It is certified that error appears in the above-identified patent and that said Letters Patent is hereby corrected as shown below:

IN THE SPECIFICATION

Column 1 Lines 8-11 Please insert the following to be of record in this Patent:

--This invention was made with Government support under Grant No. OD007124 awarded by the National Institutes of Health. The Government has certain rights in the invention.--

Signed and Sealed this
First Day of March, 2016

Michelle K. Lee
*Director of the United States Patent and Trademark Office*